US009327009B2

(12) United States Patent
Tripathi et al.

(10) Patent No.: US 9,327,009 B2
(45) Date of Patent: May 3, 2016

(54) PEPTIDE INHIBITORS AS NOVEL ANTI-HIV THERAPEUTICS

(71) Applicant: Council of Scientific & Industrial Research, New Dehli (IN)

(72) Inventors: Raj Kamal Tripathi, Uttar Pardesh (IN); Balawant Kumar, Utter Pardesh (IN); Ravishankar Ramachandran, Utter Pardesh (IN); Jitendra Kumar Tripathi, Utter Pardesh (IN); Smriti Bhadauria, Utter Pardesh (IN); Jimut Kanti Ghosh, Utter Pardesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 14/382,428

(22) PCT Filed: Mar. 1, 2013

(86) PCT No.: PCT/IB2013/051641
§ 371 (c)(1),
(2) Date: Sep. 2, 2014

(87) PCT Pub. No.: WO2013/128418
PCT Pub. Date: Sep. 6, 2013

(65) Prior Publication Data

US 2015/0182581 A1 Jul. 2, 2015

(30) Foreign Application Priority Data

Mar. 2, 2012 (IN) .......................... 0594/DEL/2012

(51) Int. Cl.

| | |
|---|---|
| ***A01N 37/18*** | (2006.01) |
| ***A61K 38/00*** | (2006.01) |
| ***A61P 31/18*** | (2006.01) |
| ***A61K 38/04*** | (2006.01) |
| ***G01N 33/50*** | (2006.01) |
| ***G01N 33/569*** | (2006.01) |
| ***C07K 14/005*** | (2006.01) |
| ***C07K 2/00*** | (2006.01) |
| ***C12Q 1/18*** | (2006.01) |

(52) U.S. Cl.
CPC . *A61K 38/04* (2013.01); *C07K 2/00* (2013.01); *C07K 14/005* (2013.01); *C12Q 1/18* (2013.01); *G01N 33/5041* (2013.01); *G01N 33/56988* (2013.01); *A61K 38/00* (2013.01); *C12N 2740/16322* (2013.01); *G01N 2500/10* (2013.01)

(58) Field of Classification Search
None
See application file for complete search history.

(56) References Cited

U.S. PATENT DOCUMENTS 6,358,511 B1 * 3/2002 Klotman et al. ........... 424/185.1
6,982,086 B2 * 1/2006 Haynes et al. ............. 424/192.1

OTHER PUBLICATIONS

Geleziunas et al. HIV-1 Nef inhibits ASK1-dependent death signaling providing a potential mechanism for protecting the infected host cell. Nature, Apr. 2001. vol. 410, pp. 834-838.*
Chang et al; Activation of Apoptosis Signal-Regulating Kinase 1(ASK1) by the Adapter Protein DAXX; Science Mag; Sep. 19, 1998; pp. 1860-1863.
Stevenson; HIV-1 Pathogenesis; Nature Medince, vol. 9, No. 7, Jul. 2003; pp. 853-860.
Colas et al; "The Impact of Two-Hybrid and Related Methods on Biotechnology"; Tibtech, vol. 16; Aug. 1998; pp. 355-363.
Fackler et al; "Functional Characterization of HIV-1 Nef Mutants in the Context of Viral Infection"; Elsevier, Virology; May 8, 2006; pp. 322-339.
Geleziunas et al; "HIV-1 Inhibits ASK1-Dependent Death Signalling Providing a Potential Mechanism for Protecting the Infected Host Cell"; Nature, vol. 410; Apr. 12, 2001; pp. 834-838.
Geyer et al; "Structure-Function Relationships in HIV-1 Nef"; EMBO, vol. 2, No. 7; May 28, 2001; pp. 580-585.
Greene et al; "Charting HIV's Remarkable Voyage Through the Cell: Basic Science as a Passport to Future Therapy"; Nature Medicine, vol. 8, No. 7; Jul. 2002' pp. 673-680.
Hanna et al; "Nef Harbors a Major Determinant of Pathogenicity for an AIDS-Like Disease Induced by HIV-1 in Transgenic Mice"; Cell, vol. 95; Oct. 16, 1998; pp. 163-175.

(Continued)

*Primary Examiner* — Marcela M Cordero Garcia
(74) *Attorney, Agent, or Firm* — Ohlandt, Greeley, Ruggiero & Perle, L.L.P.

(57) ABSTRACT

The present invention relates to synthetic peptide inhibitors (Seq ID No. 67-71) useful as anti-HIV therapeutics. The invention also relates to a novel screening method for screening anti-HIV molecules. The present invention relates to a synthetic peptide useful as anti-HIV therapeutic. The invention also relates to a novel screening method for screening of anti-HIV therapeutics. In particular, the present invention relates to reporter gene constructs for the detection of the HIV Nef and host ASK1 protein interaction. Furthermore, the invention relates to a functional interaction for Nef-ASK1 proteins prepared in a recombinant manner, a method for identifying of Nef-ASK1 interaction which causes activation of pathway to activate apoptosis presumably causing immune evasion for HIV in infected cells. The reporter gene construct according to the present invention, after it had been introduced into cells, in the presence of HIV Nef and host ASK1 proteins result in the expression of reporter luciferase protein which may be used for quantitative/qualitative interaction of HIV Nef and host ASK1 protein. The both interacting construct cloned in fluorescence expression vector when transfected in eukaryotic cells inhibits ASK1 mediated apoptosis and were reversed by the inhibitors. Furthermore, the invention was used to identify the inhibitor for the interaction of Nef-ASK1 in the cell.

12 Claims, 7 Drawing Sheets

(56) References Cited

OTHER PUBLICATIONS

Figure 1A:
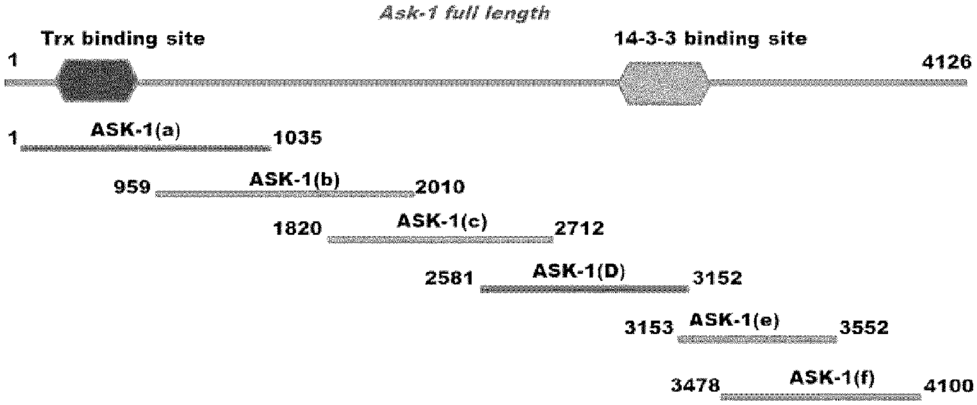

Hayakawa et al; "The ASKI-MAP Kinase Pathways in Immune and Stress Responses"; Elsevier: Microbes and Infection; Jan. 6, 2006; pp. 1098-1107.

Hodge et al; Induction of FAS Ligand Expression by an Acutely Lethal Simian Immunodeficiency Virus, SIV; Virology 252; Oct. 21, 1998; pp. 354-363.

Ichijo et al; "Induction of Apoptosis by ASK-1, A Mammalian MAPKKK That Activates SAPK/JNK and p38 Signaling Pathways"; Science, vol. 275; Jan. 3, 1997; pp. 90-94.

Katsikis et al; "FAS Antigen Stimulation Induces Marked Apoptosis of T Lymphocytes in Human Immunodeficiency Virus-Infected Individuals"; J. Exp. Med, vol. 181; Jun. 1995; pp. 2029-2036.

Kestler III et al; "Importance of the Nef Gene for Maintenance of High Virus Loads and for Development of AIDS"; Cell, vol. 65; pp. 651-662.

Kirchhoff et al; "Breif Report: Absence of Intact Nef Sequences in a Long-Term Survivor With Nonprogressive HIV-1 Infection"; New England Journal of Medicine; Jan. 26, 1995; pp. 228-232.

Murakami et al; "A Mammalian Two-Hybrid Screening System for Inhibitors of Interaction Between HIV Nef and the Cellular Tyrosine Kinase HCK"; Elsevier: Antiviral Resarch; Feb. 8, 2002; pp. 161-168.

Nishitoh et al; "ASK1 is Essential for JNK/SAPK Activation by TRAF2"; Cell, vol. 2; Sep. 1998; pp. 389-395.

Xu et al; "Evasion of Cytotoxic T Lymphocyte (CTL) Responses by Nef-Dependent Induction of FAS Ligand (CD95L) Expression on Simian Immunodefiency Virus-Infected Cells"; J. Exp. Med, vol. 186, No. 1; Jul. 7, 1997; pp. 7-16.

* cited by examiner

PEPTIDE INHIBITORS AS NOVEL ANTI-HIV THERAPEUTICS

The following specification describes the invention and the manner in which it is to be perform

FIELD OF THE INVENTION

The present invention relates to synthetic peptide inhibitors (Seq ID No. 67-71) useful as anti-HIV therapeutics. The invention also relates to a novel screening method for screening anti-HIV molecules. In particular, the invention relates to mammalian two hybrid system and cell based model for physiological response for screening of anti-HIV therapeutics. The present invention further relates to a reporter gene construct for the detection of the Negative factor (Nef)—Apoptosis signal regulating kinasel (ASK1) interaction that is essential for inhibiting apoptosis, resulting immune evasion. The physiological response of Nef-ASK1 constructs that showed interaction in mammalian-two hybrid system said to inhibit apoptosis that is activated by ASK1 was detected in ATCC CRL-1573™ cells. The peptide inhibitor identified, manages to switch from anti-apoptotic signaling to pro-apoptotic signaling in Nef transfected ATCC CRL-1573™ cells. Furthermore, the invention relates to a screening model based on Nef and ASK1 interaction in ATCC CRL-1573™ cells using a mammalian two-hybrid system and cell based model for physiological response to analyze apoptotic activity maintaining this interaction in ATCC CRL-1573™ cells, a method of screening for those inhibitors related to Nef-ASK1 interaction, a method of screening for inhibiting a pathway initiated with Nef-ASK1 interaction which inhibits apoptosis in HIV-1 infected cells causing immune evasion.

BACKGROUND OF THE INVENTION

HIV-I is the most prevalent infectious agent worldwide and a leading causative agent of acquired immuno deficiency syndrome (AIDS). HIV is a retrovirus, which is transmitted through human fluids either through natural interactions like sexual intercourse or through artificial methods like blood transfusions, infected needles used in injections. The 9-10 Kb of HIV-1 genome express viral proteins (categorized in structural, enzymatic and accessory proteins functions), whose function ranges from the successful viral infection in the cell to the complete life cycle for new virions, has been extensively studied. Every viral protein is considered to be a potential target for developing anti-HIV-1 therapy (Greene and Peterlin, 2002; Stevenson 2003).

Further, it was characterized that accessory protein Nef is responsible for HIV-1 pathogenesis (Mellors et. al., 1996) by the experiment where, Nef deleted SIVmac 239 infection in rhesus monkey showed low viral load with normal CD4 counts. These monkeys were found healthy with delayed progression to AIDS (Kestler et. al., 1991). Also, the HIV-1 patients who were long-term non-progressor, with no clinical sign of disease progression and normal CD4 counts, upon characterization of virus revealed that majority of them had Nef gene deleted from their genome (Deacon et. al., 1995, Kirchhoff et. al., 1995,). Interestingly, only expression of Nef gene in mice led to the development of AIDS like phenotype suggesting that it harbors major disease determinant (Hanna et. al., 1998). Nef is deludged with functions involving interaction with different host proteins; however, the individual function required for pathogenesis has not been identified till date.

Nef is a 27 kDa protein, expressed in HIV-1 infected cells even before the formation of provirus suggesting that it initiate functions soon after entry of virus in cell. In vitro and in vivo studies show that Nef protein enhances viral infectivity and replication respectively in infected cells. Nef downregulates the MHC classI from cell surface, which primarily presents viral proteins to activate cytotoxic T lymphocytes. Moreover, Nef functions include activation of Pak kinase, activates cascade of events leading to the activation of T cells without engaging T-cell receptor [TCR] and upregulation of Fas/FasL ligand for killing bystander cells, as well as activates anti-apoptotic pathways for the survival of infected cells. All these functions of Nef are carried out in cell after interaction with host proteins.

The one of the possible mechanism of immune evasion by HIV-1 is increase of expression of both Fas and FasL on virally infected cells (1-3). The expression of FasL is induced by the presence of Nef in virally infected cells (Xu, X. N. et al., 1997. Hodge, S. et al., 1998.). Interestingly, both Fas and FasL presence on infected cells, through cis-ligation, also undergo apoptosis in virally infected cells. The Fas and TNFα-R is known as death receptor signaling pathway which converge to a common signaling molecule known as apoptosis signaling Kinase-1(ASK1). Therefore, ASK1 appears to participate as a key signaling intermediate in both as Fas and TNFα-R pathways, that activated two different subgroup of MAP kinases kinases, SEK1 or (MKK4) and MKK3/MAPKK6(MKK5) which inturn activate JNK; c-Jun amino-terminal kinase and p38 subgroup of MAP kinase, respectively (Chang, H. Y et al., 1998). Ichijo, H. et al., 1997. Nishitoh, H. et al. 1998).

The unique cis-ligated mediated apoptosis in HIV-1 infected cell is inhibited by the presence of Nef. This protein interacts with ASK1 and inhibits the downstream signaling pathways that induce apoptosis. The molecular mechanism studied is Nef interaction with ASK1 appears by specifically preventing stimulus-coupled release of thioredoxin from ASK1 (Geleziunas. R, Xu et al., 2001). possibly, inhibition of thioredoxin release could not activate autophosphorylation of ASK1 kinase by phosphorylating 838 threonine in kinase domain. This cannot activate ASK1 mediated phosphorylation of MEKK-SEK1 kinase which activate JNK pathway (Geleziunas. R, Xu et al., 2001.Hayakawa, T. et al., 2006). The death receptor signaling—ASK1-MEKK-SEK1-JNK axis is involved in activating apoptosis in virally infected cells.

Arguably, if Nef-ASK1 interaction is inhibited then the outcome in the virally infected cells would be falling in the line of apoptosis that helps selectively clearance of HIV-1 infected cell.

Understanding the molecular Nef pathways responsible for functions involved with viral persistence, replication and infectivity can be used as target for anti HIV-1 therapy. This can enable us to focus on future therapies where the task of interrupting key interaction between viral and host proteins will serve as potential target. Nef-ASK1 interaction represents a potential target for this approach.

Recent approaches towards the development of an alternative model for characterizing specific interactions of Nef with host proteins are either yeast (Rossi et. al., 1996) or mammalian-two-hybrid system (Murakami et. al., 2002). Nef is structurally conserved and the structure function analysis revealed that with maintaining the structure, the accessible Nef conserved domain to host proteins is responsible for the function interaction in the cell (Geyer et. al., 2001).

In the present study, we developed a mammalian-two hybrid model and studied Nef-ASK1 interaction in ATCC CRL-1573™ cells, an early event which inhibits death receptor mediated apoptosis in virally infected cells (Geleziunas et al., 2001). Further, the expression of ASK1 fragments showed induction of apoptosis in ATCC TIB-152™/ATCC CRL-1573™. The ASK1 fragment that can induce apoptosis in ATCC TIB-152™/ATCC CRL-1573™ can inhibit apoptosis by the expression of Nef. The molecular mechanism studied showed that the apoptosis was induced by phosphorylation of JNK kinase which was inhibited by the presence of Nef. This model will help to screen the inhibitors designed for this interaction and perhaps, which could be used to develop an alternative therapy.

Mammalian two hybrid models have been used in scientific research in a routine manner (Colas and Brent et al., 1998). The present invention uses this technique to enable the user to establish the Nef-ASK1 interactions in ATCC CRL-1573™ cells. No other group has developed such a model for the evaluation of Nef-ASK1 interactions earlier and the present invention is the first of it's kind. The present invention serves as a novel tool to identify inhibitors of the aforesaid interactions. Inhibitors, which are so identified, will have property to activate apoptosis in cell based system and virally infected cells. There are no known drawbacks to the technique and it is amenable to high-throughput screening. The invention will efficiently allow for the screening of a large number of compounds in a relatively short time period of upto 48 hours. This will also allow for the search of structural analogs of inhibitors identified using the method of the present invention. Inhibitors, which are identified using the present invention, will act through a novel mechanism of inhibiting Nef-ASK1 interaction. This will be an alternate approach for anti-retroviral therapies including but not restricted to the Human immuno deficiency virus (HIV), which causes AIDS.

OBJECTS OF THE INVENTION

The main objective of the present invention is to provide synthetic peptide inhibitor useful as anti-HIV therapeutic.

Another object of the invention provides a novel screening method for screening anti-HIV molecules.

Yet another object of the invention is to develop mammalian two-hybrid model for assessing Nef-ASK1 interaction in ATCC CRL-1573™ cells similar to HIV-I infected cells.

The cell based assay for physiological response of Nef-ASK1 interaction said to inhibit apoptosis that is activated by ASK1 was detected in ATCC CRL-1573™ cells and ATCC TIB-152™

Another object of the invention is to provide a novel screening method to identify the molecules useful for inhibition of Nef-ASK1 interaction in eukaryotic cells.

Figures 1B, 1C:
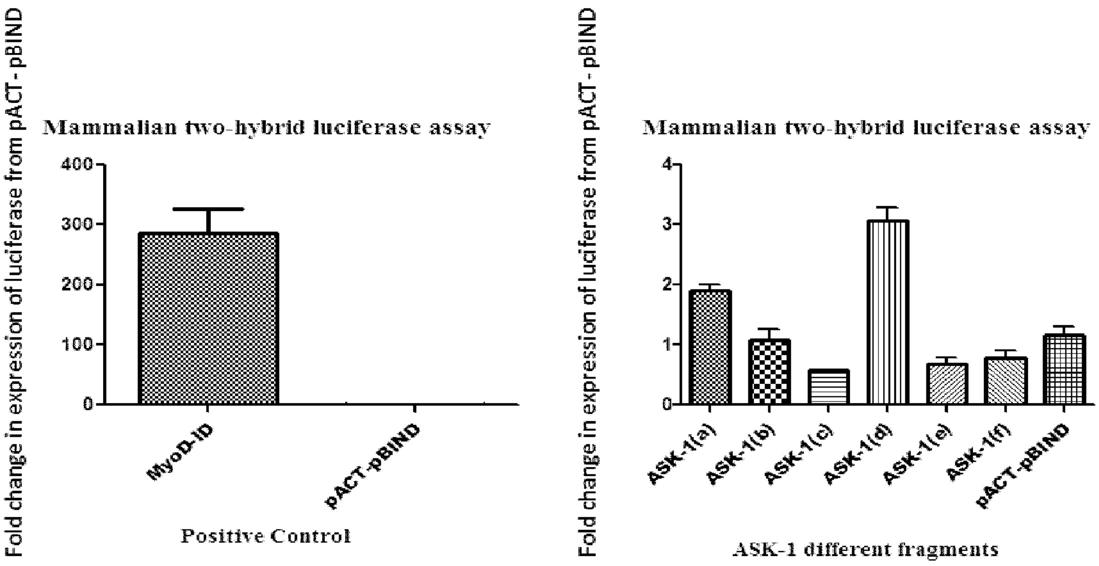

We have made ASK1 overlapping fragment (FIG. 1A) cloned in pBIND vector of mammalian two hybrid system which make recombinant protein with GAL4 binding domain. HIV-1 Nef gene was cloned in pACT vector of mammalian two hybrid vector which make recombinant protein with activation domain. In the mammalian-based system, reconstituted transcription factor activity comes from two different protein domains that are expressed from two separate vectors. The DNA binding domain of GAL4 protein and the activation domain of herpes simplex virus type 1 VP16 protein provide functional transcriptional activation from RNA polymerase II basal promoters with upstream GAL4 binding sites. In the CheckMate System, five GAL4 binding sites are positioned upstream of the firefly luciferase gene (luc+) providing a sensitive and quantitative reporter system for functional assessment of reconstituted GAL4:VP16 activity. For a positive control reaction, the pBIND-Id and the pACT-MyoD Control Vectors are co-transfected into ATCC CRL-1573™ cells along with the pG5luc (Seq ID No. 3) Vector (FIG. 1B). Vectors are transfected by Exgen 500 (farmentas).

Yet another object of the invention is to define the specific interaction of Nef and ASK1 by scanning of entire ASK1 gene by designing small ASK1 fragments.

Yet another object of invention is to define the minimal region of ASK1 gene which interacts with Nef.

Yet another object of the invention is to define the molecular mechanism of apoptosis induced by ASK1 fragment which is inhibited by interacting with Nef.

Yet another object of the invention is to define the molecular mechanism of inhibiting apoptosis by Nef-ASK1 interaction in ATCC TIB-152™/ATCC CRL-1573™ cells. Still another object of the invention is to provide the mammalian two hybrid model as a novel screening/assay system to identify novel molecules for inhibiting viral-host protein interaction.

Still another object of the invention is to provide the cell based model as a novel screening/assay system to identify novel molecules for inhibiting viral-host protein function.

SUMMARY OF THE INVENTION

Accordingly, the present invention provides a synthetic peptide useful as anti-HIV therapeutic having sequence selected from the group consisting of Seq Id No.67-71. The present invention also relates to a method for screening anti-HIV molecules comprising the steps of:

a. transfecting constructs of SEQ ID No.1, 3 and 16 respectively into a mammalian cell using 5 μl of a transfection reagent to obtain a transfected cell;
b. analyzing the transfected cell as obtained in step (a) for luciferase activity after incubating for a period of 48 hours for demonstrating Nef-ASK1 interaction using dual luciferase kit and luminometer;
c. adding the molecule to be screened in the transfected cell of step [a] and incubating for 6 to 24 hours followed by repeating step [b] to assess its inhibitory activity on the Nef-ASK1 interaction; and
d. Selecting the molecules which are inhibiting the Nef-ASK1 interaction resulting in no additional luciferase activity with respect to the control as a potential anti-HIV therapeutic.

In an embodiment of the present invention, the construct of SEQ ID No. 1 represents Nefwt gene cloned in VP16pCDNA+pACT vector.

In another embodiment of the present invention, the construct of SEQ ID No. 16 represents ASK1 gene cloned in pBIND vector.

In still another embodiment of the present invention, the construct of SEQ ID No.3 represents the reporter constructs pG5Luc.

In yet another embodiment of the present invention, the mammalian cell is selected from the group consisting of ATCC CRL-1573™ cells, T cell lines, monocytic cell lines and fibroblast cells wherein Nef-ASK1 interaction is established.

In still another embodiment of the present invention, the molecule to be screened is added at a concentration of 5 to 1.25 μm.

In yet another embodiment of the present invention, the molecule screened as a potential anti-HIV therapeutic is a DEVGEANN.

In still another embodiment of the present invention, Use of peptide is for screening Anti-HIV therapeutics.

In yet another embodiment of the present invention, compound comprising peptide or variant or a derivative or pharmaceutically acceptable salt thereof and the compound inhibits the binding of HIV-Nef to human Ask1.

In still another embodiment of the present invention, a pharmaceutical composition comprising a therapeutically effective amount of compound variant or a derivative or pharmaceutically acceptable salt thereof and the compound inhibits the fusion of HIV Nef to human ASK 1, in admixture with a pharmaceutically acceptable excipient.

In yet another embodiment of the present invention, a method of treating HIV infection that comprises providing to a recipient a therapeutically effective or a prophylactically effective amount of a pharmaceutical composition comprising a therapeutically effective amount of peptide which inhibits the fusion of HIV-Nef to human ASK1, in admixture with a pharmaceutically acceptable excipient.

In still another embodiment of the present invention, the peptide inhibits binding of HIV-Nef to human ASK1.

BRIEF DESCRIPTION OF THE ACCOMPANYING DRAWINGS

FIG. 1: Identification of ASK1 region interacting with Nef: ASK1 fragments interaction with Nef in ATCC CRL-1573™ cells. A) Designing of ASK1 fragments from N to C termination of ASK1 gene, B) MyoD-Id interaction for positive protein-protein interaction, C) ASK1a,b,c,d,e,f, fragments were transfected with Nef wt and showed luciferase activity in ATCC CRL-1573™ cells FIG. 2: Characterization of minimal ASK1 region interaction with Nef Minimal ASK1 fragments interaction with Nef: A) Designing of ASK1 fragments adding sequence upstream of ASK1a and downstream of ASK1d and adding both ASK1a and ASK1d and deleting both ASK1a and ASK1d, B) ASK1 h,l,j fragments were transfected with Nef wt and showed luciferase activity in ATCC CRL-1573™ cells. C) ASK1g fragment was transfected with Nef wt and showed luciferase activity in ATCC CRL-1573™ cells and MyoD-Id interaction for positive protein-protein interaction.

Figure 3:
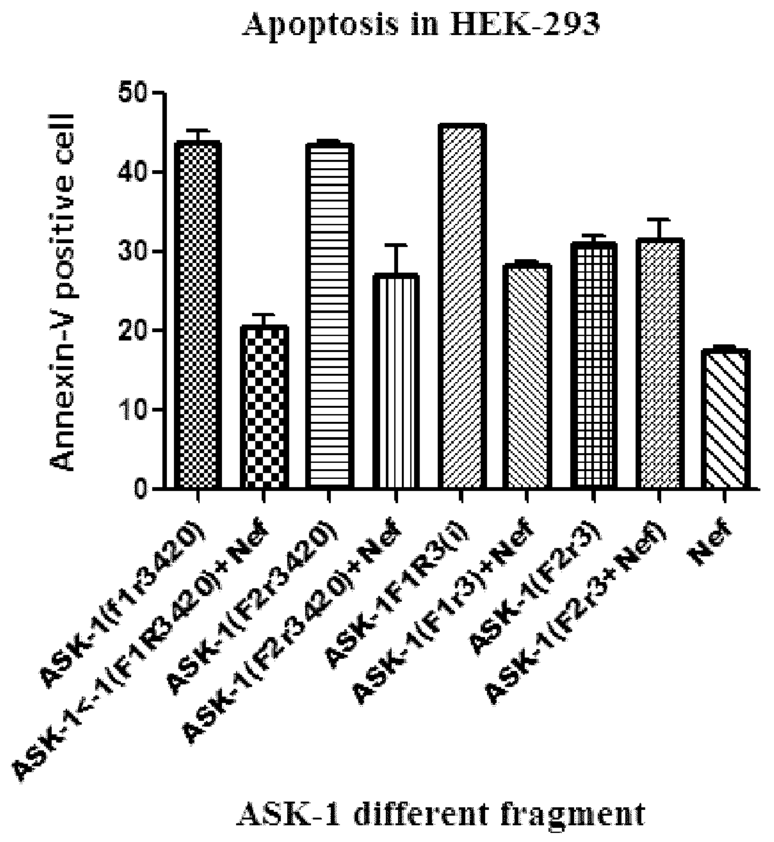

FIG. 3: To study the biochemical activity of ASK1 fragments: ASK1 fragments were analysed for activating apoptosis: ASK1 g, h,l and j fragments were transfected with and without Nef in ATCC CRL-1573™ cells and after 48 hrs apoptosis was assayed.

Figure 4A:
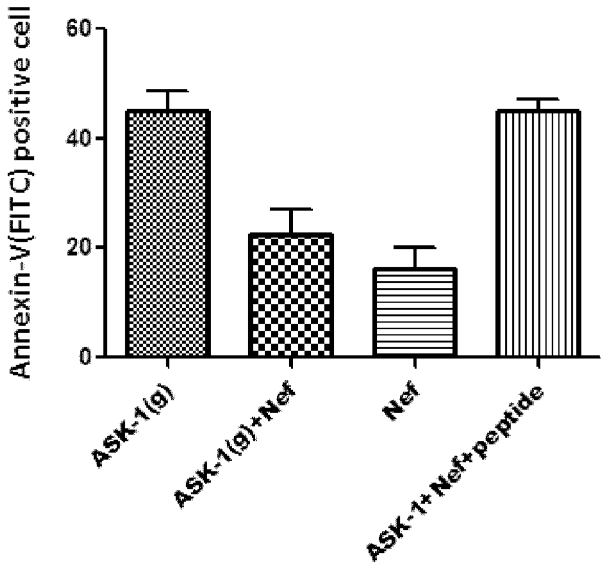
Figure 4B:
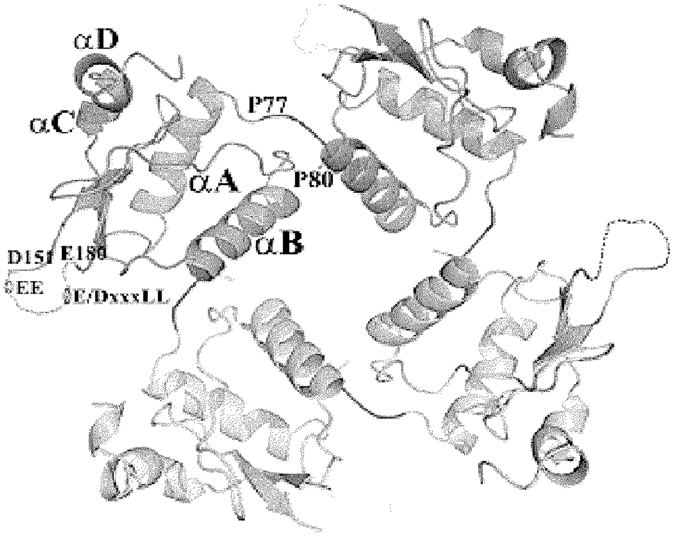

FIG. 4: Inhibition of apoptosis by Nef-ASK1g is switched to pro-apoptosis by inhibitors in ATCC CRL-1573™ cells:

Inhibition of apoptosis by Nef is reversed by inhibitors: a) Cells transfected with ASK1, ASK1 and Nef, Nef alone and Nef-ASK1 with peptides in ATCC CRL-1573™ cells were cultured for 48 hrs and analysed for apoptosis; b) crystal structure of Nef depicting tetramer structure.

Figures 5A, 5B:
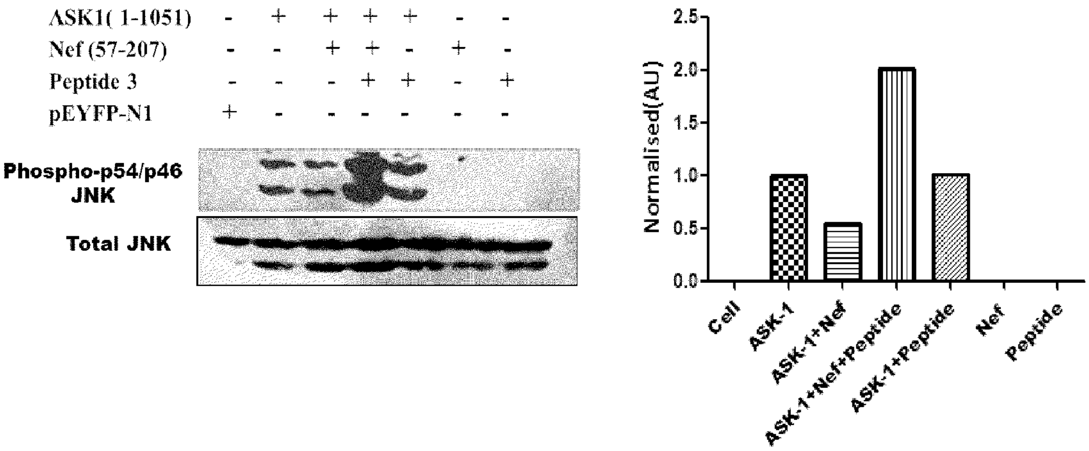

FIG. 5: Inhibitors reverse JNK phosphorylation inhibited by Nef-ASK1g interaction:

a) ASK1 induced apoptosis by JNK phosphorylation is restored by inhibitors in presence of Nef: Western blot of cell transfected with pACT vector, ASK1g, Nef and ASK1g-Nef together in and ATCC CRL-1573™ cells with or without inhibitors. The blot was probed with phosphorylated JNK antibodies and total antibody. b) Densitometric analysis of the blot was done.

Figure 6:
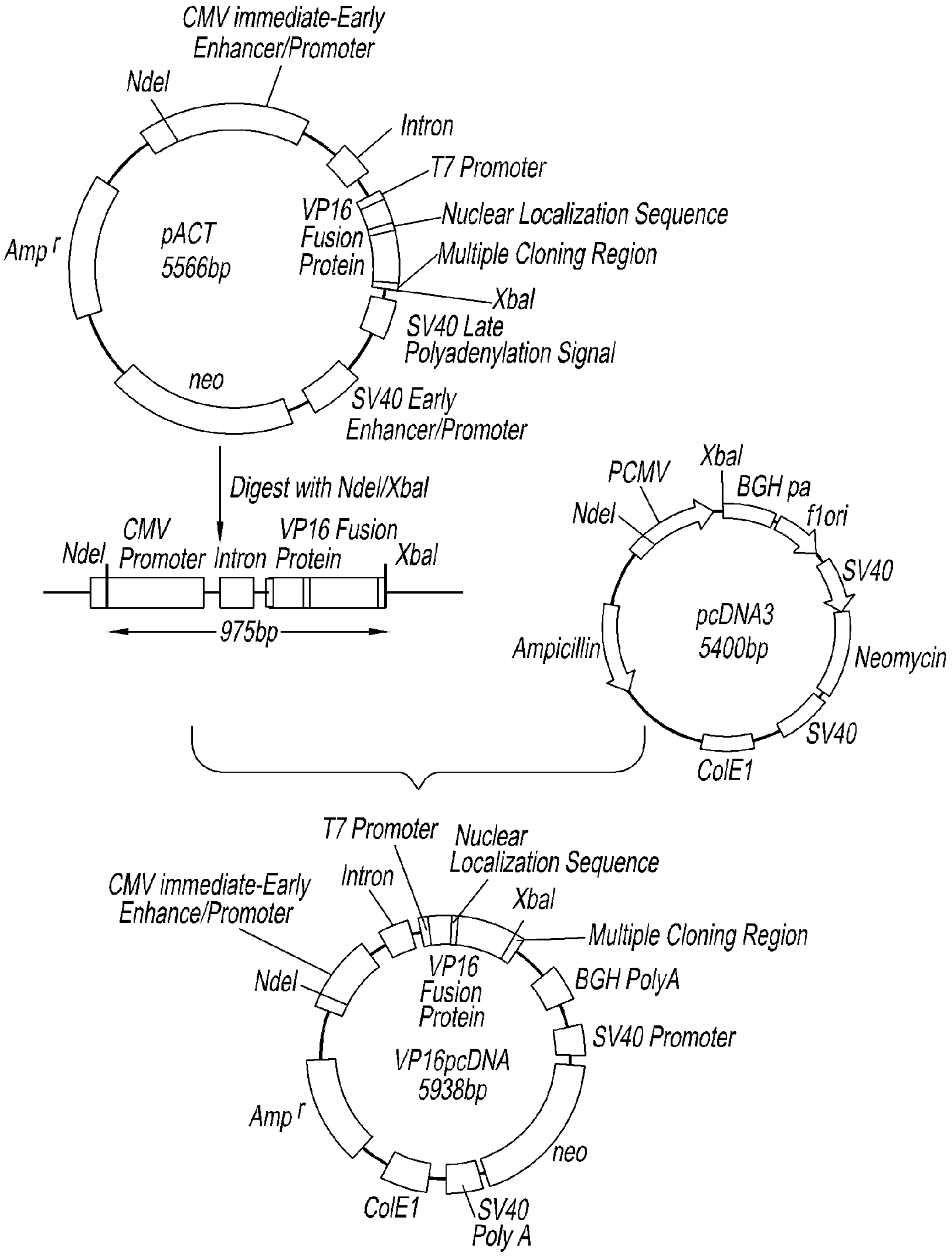

FIG. 6: Schematic representation of construction of mammalian expression vector VP16pcDNA.

Figure 7A:
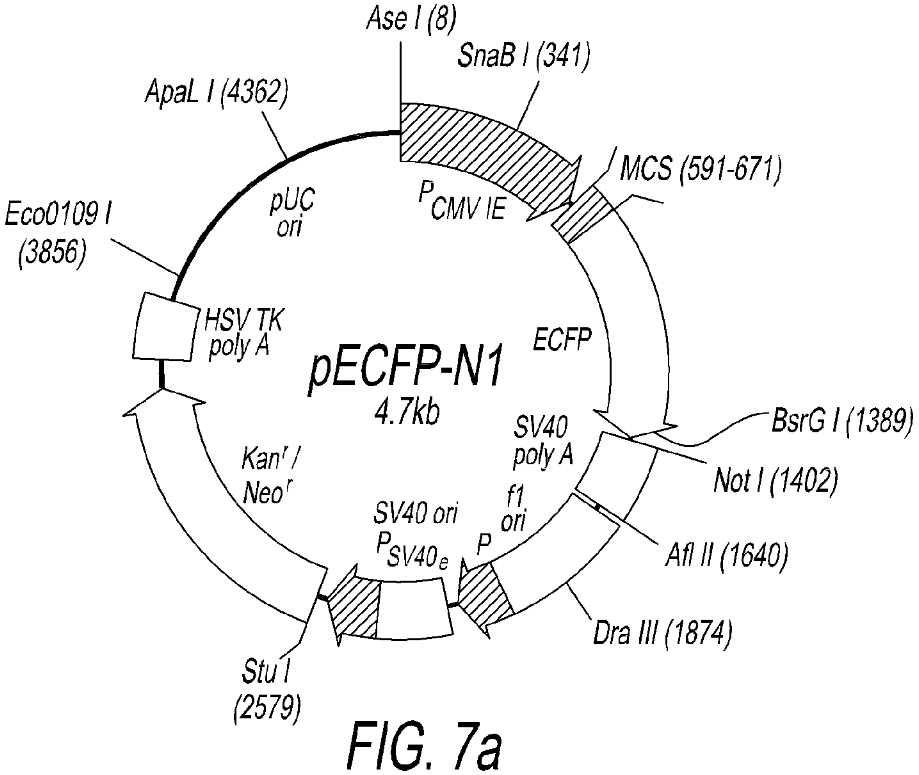
Figure 7B:
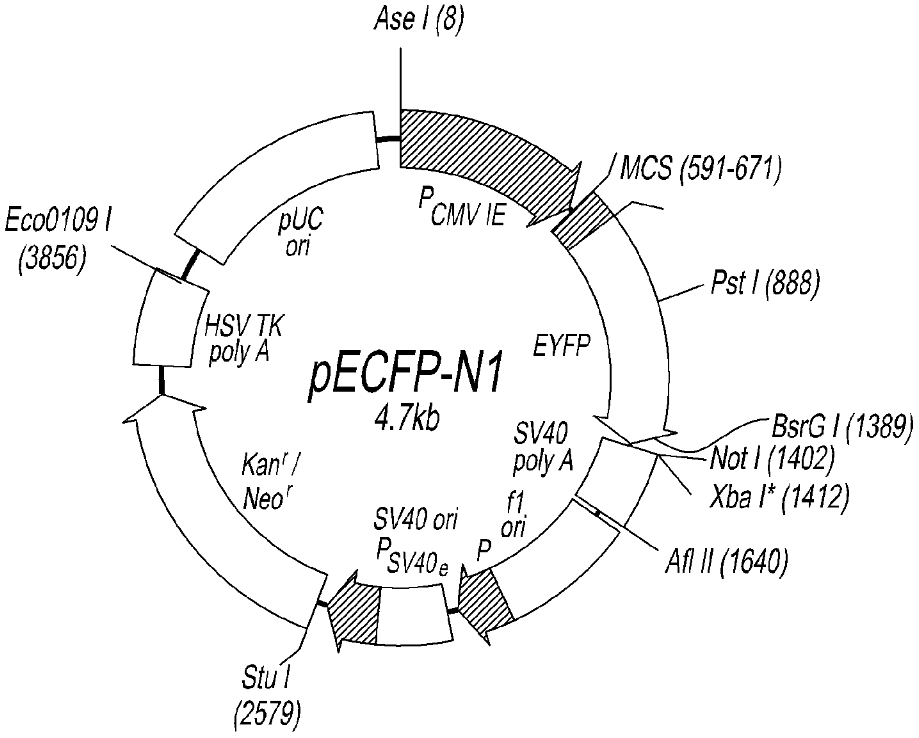

FIG. 7: Vector map of fluorescent protein gene (GFP) variants a) pEYFP-N1 and b) pECFP-N1.

DETAILED DESCRIPTION OF THE INVENTION

Definitions

A “fusion protein” refers to a polypeptide formed by the joining of two or more polypeptides through a peptide bond formed between the amino terminus of one polypeptide and the carboxyl terminus of another polypeptide. The fusion protein may be formed by the chemical coupling of the constituent polypeptides or it may be expressed as a single polypeptide from nucleic acid sequence encoding the single contiguous fusion protein. A single chain fusion protein is a fusion protein halving a single contiguous polypeptide backbone.

The term “two-hybrid system” refers to a system comprising two chimeric molecules one of which bears a nucleic acid binding region, the other of which bears an expression control element (e.g. a transactivation or repressor domain). The molecules further a cognate binding pair such that one chimeric molecule is capable of specifically binding to the other chimeric molecule. The two-hybrid system further comprises a nucleic acid encoding a protein binding site that is specifically bound by the protein binding domain on the chimeric molecule thereby anchoring the chimeric molecule to the nucleic acid. The domain of the chimeric molecule recognizes and binds to its cognate binding partner on the second chimeric molecule thereby recruiting that molecule to the nucleic acid whereby the expression control element alters (e.g. activates) expression of a gene or cDNA comprising the underlying nucleic acid.

“Transfection” is used herein to mean the delivery of expressible nucleic acid to a target cell, such that the target cell is rendered capable of expressing said nucleic acid. It will be understood that the term “nucleic acid” includes both DNA and RNA without regard to molecular weight, and the term “expression” means any manifestation of the functional presence of the nucleic acid within the cell, including without limitation, both transient expression and stable expression.

The term “transactivator” refers to a molecule that induces transcription and/or upregulates transcription of a gene or cDNA. The transactivator may be a complete “native” molecule or a domain of a molecule that is capable of inducing and/or upregulating transcription of a gene or cDNA.

“Reporter genes” are genes or cDNAs that express an easily assayable (detectable and/or quantifiable) product. Detection of the assayable product indicates the expression and/or level of expression of the reporter gene. Reporter genes are well known to those of skill in the art. They include, but are not limited to, genes expressing bacterial chloramphenicol acetyl transferase (CAT), beta-galactosidase (.beta.-gal), green fluorescent protein (GFP) and other fluorescent protein, various bacterial luciferase genes, e.g., the luciferase genes encoded by Vibrio harveyi, Vibrio fischeri, and Xenorhabdus luminescens, the firefly luciferase gene Flux, and the like.

The term “transcriptional activators” refers to proteins, which activate transcription in yeast, plant, insect and mammalian cells. These proteins contain two parts: one directs DNA binding and the other, called the activating region, presumably interacts with some component of the transcriptional machinery. Activating regions are typically acidic and require some poorly-understood aspect of structure, probably at least in part an alpha-helix.

Here in the present invention, the “transcriptional activator system” utilized is the one, which is formed by fusing a DNA-binding fragment of the yeast activator GAL4 to a highly acidic portion of the herpes simplex virus protein VP16. VP16 activates transcription of immediate early viral genes by using its amino-terminal sequences to attach to one or more host-encoded proteins that recognize DNA sequences in their promoters.

Amplification of ASK1 Gene Fragments:

The full length ASK1 cDNA cloned in pCMVsport6 vector (BC054503) was purchased from SAF labs. We designed the ASK1 (a-f) overlapping fragments of approximately one 1 kb covering the entire ASK1 gene (FIG. 1). The forward and reverse primers are designed for amplifying ASK1 fragments as shown in table 1.

Plasmid Constructs—

Nef gene was cloned in VP16pcDNA plasmid constructed in lab using pcDNA 3 (Invitrogen) as vector backbone, while the fragment containing the CMV promoter, intron, T7 promoter, nuclear localization signal and multiple cloning region was taken from the mammalian two-hybrid assay vector pACT. The resulting construct thus containing the cloned Nef gene was called VP16pCDNA+pACT (Seq ID No. 1).

Two sets of constructs were generated from the two vectors, pBIND and VP16pCDNA+pACT:

ASK1 fragments ASK1a (Seq ID No. 4), ASK1b (Seq ID No. 6), ASK1c (Seq ID No. 8), ASK1d (Seq ID No. 10), ASK1e (Seq ID No. 12), ASK1f (Seq ID No. 14), ASK1g (Seq ID No. 16), ASK1h (Seq ID No. 18), ASK1i (Seq ID No. 20) and ASK1j (Seq ID No. 22) were cloned in pBIND vector.

HIV-1 Nef gene was cloned in VP16pCDNA+pACT

PCR was performed for each gene using the appropriate 5' and 3' primers (as given in Table 1). For cloning of ASK1 fragment in pBIND vector of mammalian two vectors all primer contains BamH1 restriction site in forward primer and Xbal restriction site in reverse primer. All constructs were verified by Sanger sequencing in an ABI Automatic Sequencing System (PerkinElmer Applied Biosystems Inc, Foster City, Calif.). The primers were custom-synthesized by Sigma, Operon and IDT.

TABLE 1

Primers used for Nef cloning and ASK1 for mammalian two hybrid system

| Gene | primer | Primer Sequence (5' . . . 3') | Seq. ID No. |
|---|---|---|---|
| HIV-1nef Gene of accession no. GQ184335 cloned in VP16pCDNA + pACT | FPN1<br>RPN1 | 5' CATGGATCCGTGGAGCACTTACAAGCAGCA 3'<br>5' CATGGATCCTCAGCAGTCTTTGTAATACTCC 3' | Seq ID No 35, 36 |
| ASK1 gene of accession no. BC054503 for 1035 bp ASK1(a) length from N-terminal gene cloned in pBIND | FP1<br>RP1 | 5'AGCGGATCCGTACGGAGGCGGACGAGGGCATCA3'<br>5'AGCGTCTAGACAAATCAAAGGTTGGCAG3' | Seq ID No 37, 38 |
| ASK1 gene of accession no. BC054503 for 1051 bp ASK1(b) length gene cloned in pBIND | FP2<br>RP2 | 5'AGCGGATCCGTTCCTACAGAGATATCCAGGAC3'<br>5'AGCGTCTAGACAAGTCACTTTCACAGTCTC3 | Seq ID No 39, 40 |
| ASK1 gene of accession no. BC054503 for 892 bp ASK1(c)length gene cloned in pBIND | FP3<br>RP3 | 5'AGCGGATCCGTTCTTCTGTCAGGGGAGTGA3'<br>5'AGCGTCTAGATGGGATCTCAGGGTGGAC3 | Seq ID No 41, 42 |
| ASK1 gene of accession no. BC054503 for 571 bp ASK1(d)length gene cloned in pBIND | FP4<br>RP3420 | 5'AGCGGATCCGTGCAGCAGACATCTGGTCTC3'<br>5'AGCGTCTAGAACTCTCAGATGCAAGGCTG3' | Seq ID No 43, 44 |
| ASK1 gene of accession no. BC054503 for 399 bp ASK1(e) length gene cloned in pBIND | FP4<br>RP4 | 5'AGCGGATCCGTGACAGTATCATTCGGAAGGCGG3'<br>5'AGCGTCTAGAGTCAATGATAGCCTTCCACAG3' | Seq ID No 45, 46 |
| ASK1 gene of accession no. BC054503 for ASK1(f)length cloned in pBIND | FP5<br>RP5 | 5'AGCGGATCCGTACGGAGGCGGACGAGGGCATCA3'<br>5'AGCGTCTAGATCGCCTCTCACTGTCCTTCC3' | Seq ID No 47, 48 |

TABLE 1-continued

Primers used for Nef cloning and ASK1 for mammalian two hybrid system

| Gene | primer | Primer Sequence (5' . . . 3') | Seq. ID No. |
|---|---|---|---|
| ASK1 gene of accession no. BC054503 for ASK1(g) length from N-terminal gene cloned in pBIND | FP1<br>RP3420 | 5'AGCGGATCCGTACGGAGGCGGACGAGGGCATCA3'<br>5'AGCGTCTAGAACTCTCAGATGCAAGGCTG3' | Seq ID No 49, 50 |
| ASK1 gene of accession no. BC054503 for ASK1(h) length from N-terminal gene cloned in pBIND | FP2<br>RP3420 | 5'AGCGGATCCGTTCCTACAGAGATATCCAGGAC3'<br>5'AGCGTCTAGAACTCTCAGATGCAAGGCTG3' | Seq ID No 51, 52 |
| ASK1 gene of accession no. BC054503 for ASK1(i) length from N-terminal gene cloned in pBIND | FP1<br>RP3 | 5'AGCGGATCCGTACGGAGGCGGACGAGGGCATCA3'<br>5'AGCGTCTAGATGGGATCTCAGGGTGGAC3' | Seq ID No 53, 54 |
| ASK1 gene of accession no. BC054503 for ASK1(j) length from N-terminal gene cloned in pBIND | FP2<br>RP3 | 5'AGCGGATCCGTTCCTACAGAGATATCCAGGAC3'<br>5'AGCGTCTAGATGGGATCTCAGGGTGGAC3' | Seq ID No 55, 56 |

Cloning of ASK1 in pEYFP-N1 Vector

ASK1and HIV-1 Nef (Seq ID No. 25) clones were cloned in pEYFP-N1 (Seq ID No. 24) (clontech #6006-1) vector for detection of apoptosis and c-jun, $p^{38}$ phosphorylation analysis. Plasmid was constructed by using primer containing SalI and BamHI restriction site in forward and reverse primer respectively for ASK1 clone and HindIII, SalI in forward and reverse primer respectively for HIV-1 Nef clone. Primer sequence are given below in table-2

TABLE-2 primer sequence for cloning of ASK1 fragment in pEYFP-N1 vector

| Gene | primer | Primer Sequence (5' . . . 3') | Sequence ID No. |
|---|---|---|---|
| HIV-1 Nef Gene of accession no. GQ184335 Cloned in pEYFP-N1 | FP1<br>RP1 | 5'AGCAAGCTTATGGGGGGCAAGTGGTCAAAA3'<br>5AGCGTCGACGCGCAGTCTTTGTAAACTCC G 3' | Seq ID No 57, 58 |
| ASK1 gene of accession no. BC054503 for ASK1(g) Cloned in pEYFP-N1 | FP2<br>RP2 | 5'GTCGA ATGAGCACGGAGGCGACGAGGGCAT3'<br>5'GGATCCCGCCTCTCACTGTCCTTCCTCAGCATG3' | Seq ID No 59, 60 |
| ASK1 gene of accession no. BC054503 for ASK1(h) Cloned in pEYFP-N1 | FP3<br>RP3 | 5' CGAGCGTCGACATGTCCTAC AGA GAT ATC CAG GAC TAT GA 3'<br>5'GGATCCCGCCTCTCACTGTCCTTCCTCAGCATG3' | Seq ID No 61, 62 |
| ASK1 gene of accession no. BC054503 for ASK1(h) Cloned in pEYFP-N1 | FP4<br>RP4 | 5'GTCGA ATGAGCACGGAGGCGGACGAGGGCAT3'<br>5'AGCGGATCC TCTGGGATCTCAGGGTGGACT T3' | Seq ID No 63, 64 |

TABLE-2-continued

| primer sequence for cloning of ASK1 fragment in pEYFP-N1 vector | | | |
|---|---|---|---|
| Gene | primer | Primer Sequence (5' . . . 3') | Sequence ID No. |
| ASK1 gene of accession no. BC054503 for ASK1(j) Cloned in pEYFP-N1 | FP5 RP5 | 5' CGAGCGTCGACATGTCCTACAGAGATATCCAG GAC TAT GA 3' 5' AGCGGATCCTCTGGGATCTCAGGGTGGACTT 3' | Seq ID No 65, 66 |

Tissue Culture and Transfections—

HEK 293 cells were grown in Minimal Essential medium (low glucose, Sigma) supplemented with 10% fetal bovine serum, penicillin (100 units/ml), streptomycin (100 μg/ml) and Gentamycin (50 μg/ml) at 37° C. with 5% $CO_2$. $1\times10^5$ cells were seeded per well in twenty four well plates, one day before transfection. Using commercially available ExGen 500 (fermentas) transfection reagent, all the required endotoxin free plasmid constructs were co-transfected into HEK 293 cells. 0.75 microgram of each plasmid and 5.0 micro liters per well ExGen 500 reagent were used. 48 h post transfection the cells were harvested and Luciferase activity was monitored using the Dual-Luciferase® Reporter assay kit (Promega). The data for basal control were used for the conversion of Luciferase activity to fold activation. As a positive control, the protein-protein interaction vectors pACTMyoD and pBIND-ID encoding the MyoD and ID control proteins, provided with the kit were used.

Luciferase Assay—

The transfected cells were lysed in 1× Passive Lysis Buffer (PLB) provided with the kit, and the cell extracts (containing Luciferase enzyme) were added to the luminometer tubes and the Luciferase and Renilla RLU were measured on Berthold luminometer using the respective substrates for 10s along with 2s delay time.

EXAMPLE

The following examples are given by way of illustration and therefore should not be construed to limit the scope of the invention.

Example 1

To Identify the Region(s) in ASK1 Interacting with Nef Using Mammalian Two-Hybrid Model The ASK1 interacts with Nef and inhibits apoptosis (Geleziunas et al 2001), however, the region of ASK1 that is interacting with Nef is not known. To identify which region it is interacting, the ASK1 gene approximately 4.1 Kb, was divided in overlapping fragments of approximately 1 Kb from N-terminal to cover entire ASK1 gene. These fragments were cloned in pBIND mammalian two-hybrid vector, which has GAL4 DNA binding domain. The ASK1 fragment cloned in pBIND were; ASK1a (1-1035), ASK1b (959-2010), ASK1c (1820-2712), ASK1d (2581-3152), ASK1e (3153-3552) and ASK1 f (3478-4100), as shown in FIG. (1*a*). The full length Nef gene was cloned in pACT mammalian two hybrid vector, which has all the interacting domains (Accession no.GQ184335). The mammalian two-hybrid vectors cloned with or without Nef and ASK1 fragments were co-transfected along with G5Luc (luciferase) vector in ATCC CRL-1573™ cells. The reporter luciferase expression was measured after 48 hours of transfection. Among the ASK1 fragments, ASK1a, ASK1b and ASK1d showed 2.28, 1.10 and 2.89 fold, respectively, luciferase activity compared to negative control pACT-pBIND. ASK1c, ASK1d and ASK1f showed no luciferase activity compared to control, as shown in FIG. 1(*b*). The MyoD-Id protein was taken as positive control for showing interaction of proteins in mammalian-teo hybrid model, as shown in FIG. 1*c*). In this model the set of vectors which is expressing luciferase gene in cells are considered to be interacting with each other. Our results show that ASK1a, ASK1b and ASK1d fragment in presence of Nef express luciferase gene which shows that they interact with Nef where as other fragments of ASK1 does not show any tendency for interaction with Nef.

Example-2

Characterization of Minimal ASK1 Region Interacting with Nef

In mammalian two-hybrid model, ASK1a, ASK1b and ASK1d fragments showed interaction with Nef which indicate that these fragments may have tendency in ASK1 for its interaction ability. We characterized the ASK1a downstream sequence and ASK1d upstream sequence in context to Nef interaction.

Figure 2A:
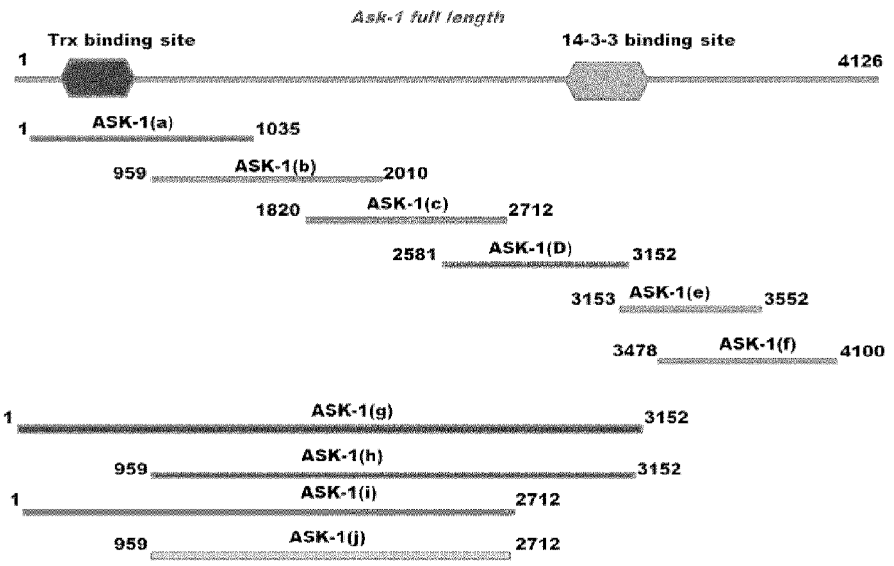

Constructs were made based by adding upstream and downstream sequences of ASK1a and ASK1d respectively. Larger constructs which were made are ASK1g (contain both ASK1a, ASK1d and in between sequence), ASK1h (Contain ASK1d and upstream sequence), ASK1i (contain ASK1a and downstream sequence) and ASK1j (contain in between ASK1a and ASK1d fragment), as shown in FIG. 2*a*. All the ASK1 constructs were cloned in pBIND mammalian two-hybrid vectors. The ASK1 fragments and Nef were co-transfected along with G5Luc vector, in ATCC CRL-1573™ cells and luciferase activity was measured 48 hrs post transfection.

Figure 2B:
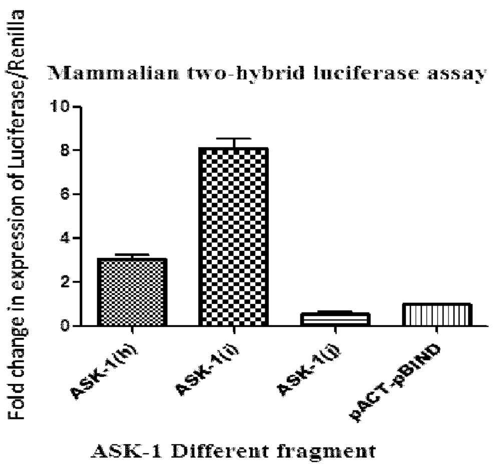
Figure 2C:
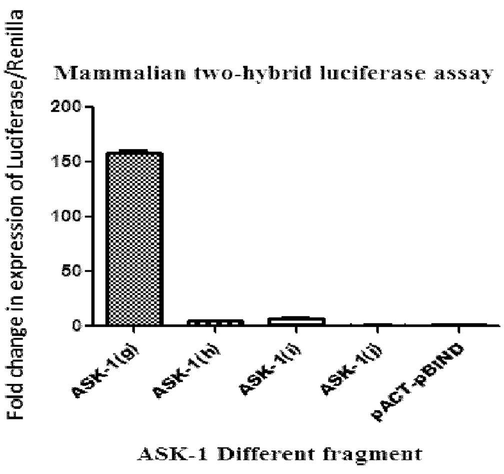

The ASK1g fragment showed maximum luciferase activity 154 fold times compared to negative control pACT-pBIND, as shown in FIG. 2*c*. The ASK1i and ASK1h showed luciferase activity 2.72 and 8.41 fold respectively as compared to negative control, as shown in FIG. 2*b*. In ASK1h having both ASK1a and ASK1b fragments showed synergistic effect. The ASK1j showed no luciferase activity 0.5 fold same as negative control was found (FIG. 2*b*).

These results showed that ASK1g is the minimal region of ASK1 required for interaction with Nef, deletion of either ASK1a or ASK1d reduced substantially interaction with Nef and loss of both fragments from ASK1g leads to complete loss of interaction. These results indicate that ASK1g fragment interacts with Nef through ASK1a and ASK1d regions.

Example-3

To Study the Effect of ASK1g,h,l,j Fragments in Inducing Apoptosis and its Inhibition by Nef ASK1 expression either by external stress stimuli or over expression of ASK1 gene activates apoptosis in cells. ASK1 is active in oligomeric state. The N and C region have oligomerization sequence. ASK1 is oligomerized with C region coiled coil region and at N-region after release of thioredoxin protein. ASK1 catalytic domain (670-940) forms a tight dimmer interacting in a head-to-tail fashion (Bunkoczi. et al 2007, Structure 15, 1215-1226). The oligomerization activates self phosphorylation of 838 Threonine residue in the kinase domain. Nef inhibits apoptosis by interacting with ASK1.

The ASK1g, h, i, j fragments showing interactions in mammalian two-hybrid model were studied for its function to induce apoptosis in ATCC CRL-1573™ cells and its inhibition by Nef.

The ASK1g, h, i,j fragments alone and with Nef were transfected in ATCC CRL-1573™ cells. The transfected cells were cultured for 48 hours and were labeled with AnnexinV and PI staining for analyzing aspoptosis.

The ASK1g,h,l, fragments induces apoptosis in ATCC CRL-1573™ cells and percentage positive cells for annexinV staining were 42, 42 and 45% respectively compared to control cells. The Nef co-transfected with ASK1g, ASK1h and ASK1i showed 20%, 38% and 26% respectively annexin V stained cells that show inhibition of apoptosis by 52%, 10% and 42% respectively. The ASK1j has 28% annexin V stained cells compared to Nef control 20% and after Nef co-transfection there is no reduction in apoptosis compared to ASK1j, as shown in (FIG. 3).

These results showed that all fragments of ASK1g, h,i,j induces apoptosis in ATCC CRL-1573™ cells but the apoptosis is inhibited substantially by Nef with the ASK1g and ASK1i fragment.

Example-4

Inhibitor Reversing Nef-ASK1 Effect in ATCC CRL-1573™ Cells

Inhibitors were designed from the crystal structure of Nef solved in our laboratory (Pankaj et al., 2011) The inhibitors were cultured with cells transfected will Nef, ASK1g and co-transfected with Nef-ASK1g. The cells after 48 hours were analysed for apoptosis using annexin V and PI staining. The results show that the Nef-ASK1 expression in ATCC CRL-1573™ cells inhibited apoptosis by 50% compared to ASK1 alone. The inhibitors reversed the effect of Nef-ASK1 interaction that is inhibition of apoptosis by increasing annexin V stained cells same to ASK1 cells FIG. 4.

This result suggests that Nef-ASK1 co-transfected in cells show inhibition of apoptosis and is reversed by inhibitors.

| S. No | Peptide seq. | Peptide No | Seq ID No. | % of Annexin V cells means apoptotic cells | Remarks |
|---|---|---|---|---|---|
| 1 | TPGPGVRYP | Peptide-1 | 57 | 22.45 | Same as background |
| 2 | GENNCLLH | Peptide-2 | 58 | 24.96 | Same as background |
| 3 | DEVGEANN | Peptide-3 | 59 | 40.37 | Active Reversing interaction |

-continued

| S. No | Peptide seq. | Peptide No | Seq ID No. | % of Annexin V cells means apoptotic cells | Remarks |
|---|---|---|---|---|---|
| 4 | LHGMEDPE | Peptide-4 | 60 | 23.0 | Same as background |
| 5 | PVRPQVPLRP | Peptide-5 | 61 | 22.45 | Same as background |
| 6 | ASK-1 | | | 43.15 | ASK-1 protein affect |
| 7 | ASK-1 + Nef | | | 22.15 | Interaction (Background) |
| 8 | Control | | | 11.0 | |

Example-5

Effect of Inhibitors in Restoring Apoptosis by Reversing JNK Phosphorylation Inhibited by Nef-ASK1g Interaction in ATCC CRL-1573™ Cells ASK1 MAPKKK induces apoptosis by JNK and p38 pathway. To identify that the minimal ASK1g fragment can activate JNK and p38 pathway to induce apoptosis and the presence of Nef can affect this pathway.

The ASK1 g and Nef were transfected alone and co-transfected in ATCC CRL-1573™ cells. The JNK and p38 pathways were detected by analyzing phosphorylation of JNK or p38 kinases by using phosphorylated antibodies. The results showed that ASK1g fragment activated JNK pathway by phosphorylated JNK kinase where as late effect was seen in p38 kinase (data not shown). Further in co-transfected cell with Nef, inhibits the phosphorylation of JNK kinase whereas In presence of peptide the JNK phosphorylation is reversed, same as ASK-1, inhibited by Nef-ASK-1 interaction (FIG. 5). Densitometry analysis showed that Nef decrease phosphorylation of JNK kinase 2 fold compare to ASK1g transfected cells (FIG. 5). Nef alone transfected cell show no phosphorylation of JNK kinase compared to control. These results suggest that ASK1g activates apoptosis by JNK pathway and this pathway is inhibited with the presence of Nef in ATCC CRL-1573™ cells and is reversed in presence of inhibitor.

Advantages of the Invention

The reporter gene construct is simple to use and does not involve human or animal models of testing.

This method is amenable to screening a large number of compounds in a relatively short time when coupled with high-throughput technologies or as a stand-alone assay procedure.

Rapid inhibitor optimization is facilitated by quick screening procedure.

The present inhibitor(s) will be a novel therapeutic and will overcome HIV-I resistance issues.

REFERENCES

Chang, H. Y., Nishitoh, H., Yang, X., Ichijo, H. & Baltimore, D. Activation of apoptosis signalregulating kinase 1 (ASK1) by the adapter protein Daxx. Science 281, 1860-1863(1998).

Colas, P and Brent, R. The impact of two-hybrid and related methods on biotechnology. TIBTECH 16, 355-363.1998.

Deacon, N. J., Tsykin, A., Solomon, A., Smith, K., Ludford, M. M., Hooker, D. J., McPhee, D. A., Greenway, A. L., Ellett, A., Chatfield, C., and et, a. I. (1995). Genomic structure of an attenuated quasi species of HIV-1 from a blood transfusion donor and recipients [see comments]. Science 270,988-91.

Fackler, O., Moris, A., Tibroni, N., Giese, S., Glass, B., Schwartz, O. and Kräusslich, H. G. Functional characterization of HIV-1 Nef mutants in the context of viral infection. Virology 351:332-339. (2006).

Geleziunas. R, Xu. W, Takeda. K, Ichijo. H & Greene. W. C. HIV-1 Nef inhibits ASK1-dependent death signalling providing a potential mechanism for protecting the infected host cell. Nature, VOL 410, 834. (2001).

Greene, W. C and Peterlin, B. M. Charting HIV's remarkable voyage through the cell: Basic science as a passport for future therapy. Nature medicine 8, 673-680. (2002).

Geyer M, Fackler O T, Peterlin B M 2001 Structure—function relationships in HIV-1 Nef.

Hanna Z, Kay D G, Rebai N, Guimond A, Jothy S and Jolicoeur P 1998 Nef harbors a major determinant of pathogenicity for an AIDS-like disease induced by HIV-1 in transgenic mice; Cell 95 163-175

Hayakawa, T., Matsuzawa, A., Noguchi, T., Takeda, K., and Ichijo, H.

(2006). The ASK1-MAP kinase pathways in immune and stress responses. Microbes Infect. 8, 1098-1107.

Hodge, S., Novembre, F. J., Whetter, L., Gelbard, H. A. & Dewhurst, S. Induction of fas ligand expression by an acutely lethal simian immunodeficiency virus, SIVsmmPBj14. Virology 252, 354-363 (1998).

Ichijo, H. et al. Induction of apoptosis by ASK1, a mammalian MAPKKK that activates SAPK/JNK and p38 signaling pathways. Science 275, 90-94 (1997).

Kirchhoff F, Greenough T C, Brettler D B, Sullivan J L and Desrosiers R C 1995 Brief report: absence of intact nef sequences in a long-term survivor with nonprogressive HIV-1 infection [see comments]; N. Engl. J. Med. 332 228-232

Katsikis, P. D., Wunderlich, E. S., Smith, C. A. & Herzenberg, L. A. Fas antigen stimulation induces marked apoptosis of T lymphocytes in human Immunode®ciency virus-infected individuals. J. Exp. Med. 181, 2029-2036 (1995).

Kestier, H. W., Ringler, D. J., Mori, K., Panicali, D. L., Sehgal, P. K., Daniel, M. D. and Desrosiers, R. C. Importance of the nef gene for maintenance of high virus loads and for development of AIDS. Cell 65:651-662 (1991).

Nishitoh, H. et al. ASK1 is essential for JNK/SAPK activation by TRAF2. Mol. Cell biology 2, 389-395 (1998).

Singh P, Yadav G P, Gupta S, Tripathi A K, Ramachandran R, and Tripathi R K (2011) A novel dimer-tetramer transition captured by the crystal structure of the HIV-1 Nef. PLoS One, 6, e26629.

Rossi, F., Gallina, A., & Milanesi, G. (1996) Virology 217, 397-403.

The invention claimed is:

1. A synthetic peptide useful as anti-Human Immunodeficiency Virus (anti-HIV) therapeutic having the sequence of SEQ ID NO. 69.

2. A method for screening anti-HIV molecules comprising the steps of:

a. transfecting constructs of SEQ ID No. 1, 3 and 16 into a mammalian cell using 5 μl of a transfection reagent to obtain a transfected cell;

b. analyzing the transfected cell as obtained in step (a) for luciferase activity after incubating for a period of 48 hours for demonstrating Negative factor (Nef)-Apoptosis signal regulating kinase 1 (ASK1) interaction;

c. adding the molecule to be screened in the transfected cell of step [a] and incubating for 6 to 24 hours followed by repeating step [b] to assess its inhibitory activity on the Nef-ASK1 interaction;

d. selecting the molecules which are inhibiting the Nef-ASK1 interaction resulting in no additional luciferase activity with respect to the control as a potential anti-HIV therapeutic.

3. The method as claimed in claim 2 wherein the construct of SEQ ID NO. 1 represents Nefwt gene cloned in VP16pCDNA+pACT vector.

4. The method as claimed in claim 2 wherein the construct of SEQ ID NO. 16 represents ASK1 gene cloned in pBIND vector.

5. The method as claimed in claim 2 wherein the construct of SEQ ID NO. 3 represents the reporter constructs pG5Luc.

6. The method as claimed in claim 2 wherein the mammalian cell is selected from the group consisting of T cell lines, monocytic cell lines and fibroblast cells wherein Nef-ASK1 interaction is established.

7. The method as claimed in claim 2 wherein the molecule to be screened is added at a concentration of 5 to 1.25 μm.

8. The method as claimed in claim 2 wherein the molecule screened as a potential anti-HIV therapeutic is a synthetic peptide having a sequence of SEQ ID NO. 69 (DEVGEANN).

9. A pharmaceutical composition comprising a therapeutically effective amount of a synthetic peptide selected from the group consisting of: a synthetic peptide having the sequence of SEQ ID NO. 69, a functional variant of the synthetic peptide having the sequence of SEQ ID NO. 69, functional derivative of the synthetic peptide having the sequence of SEQ ID NO. 69, a pharmaceutically acceptable salt of any of the foregoing, along with a pharmaceutically acceptable excipient, wherein said peptide or pharmaceutically acceptable salt thereof inhibits the fusion of HIV Nef to human ASK 1.

10. A method of treating HIV infection that comprises providing to a recipient a therapeutically effective or a prophylactically effective amount of a pharmaceutical composition comprising a therapeutically effective amount of a peptide selected from the group consisting of: a synthetic peptide having the sequence of SEQ ID NO. 69, a functional variant of the synthetic peptide having the sequence of SEQ ID NO. 69, a functional derivative of the synthetic peptide having the sequence of SEQ ID NO. 69 and a functional pharmaceutically acceptable salt of any of the foregoing, wherein said peptide or pharmaceutically acceptable salt thereof inhibits the fusion of HIV-Nef to human ASK1 along with a pharmaceutically acceptable excipient.

11. The method as claimed in claim 2, wherein the molecule to be screened comprises the synthetic peptide of claim 1.

12. A method of inhibiting the binding effect of HIV-Nef to human ASK1 by reversing the c-Jun N-terminal kinases (JNK) phosphorylation, the method comprising providing to a recipient a therapeutically effective amount of a synthetic peptide having SEQ. ID NO. 69.

* * * * *

SEQUENCE LISTING

```
<160> NUMBER OF SEQ ID NOS: 71

<210> SEQ ID NO 1
<211> LENGTH: 6234
<212> TYPE: DNA
<213> ORGANISM: Artificial Sequence
<220> FEATURE:
<223> OTHER INFORMATION: nefwt sequence cloned in VP16pCDNA+pACT vector

<400> SEQUENCE: 1

gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgac gtattagtca tcgctattac catggtgatg cggttttggc agtacaccaa    540

tgggcgtgga tagcggtttg actcacgggg atttccaagt ctccacccca ttgacgtcaa    600

tgggagtttg ttttggcacc aaaatcaacg ggactttcca aaatgtcgta acaactgcga    660

tcgcccgccc cgttgacgca aatgggcggt aggcgtgtac ggtgggaggt ctatataagc    720

agagctcgtt tagtgaaccg tcagatcact agaagcttta ttgcggtagt ttatcacagt    780

taaattgcta acgcagtcag tgcttctgac acaacagtct cgaacttaag ctgcagtgac    840

tctcttaagg tagccttgca gaagttggtc gtgaggcact gggcaggtaa gtatcaaggt    900

tacaagacag gtttaaggag accaatagaa actgggcttg tcgagacaga gaagactctt    960

gcgtttctga taggcaccta ttggtcttac tgacatccac tttgcctttc tctccacagg   1020
```

-continued

```
tgtccactcc cagttcaatt acagctctta aggctagagt acttaatacg actcactata   1080
ggctagccag cttgaagcaa gcctcctgaa agatgaagct actgtcttct atcgaacaag   1140
catgcccaaa aaagaagaga aaggtagatg aattcccggg gatctcgacg gcccccccga   1200
ccgatgtcag cctgggggac gagctccact tagacggcga ggacgtggcg atggcgcatg   1260
ccgacgcgct agacgatttc gatctggaca tgttgggga cggggattcc ccgggtccgg   1320
gatcgccagg gatccgtgga gcacttacaa gcagcaacac agcccaaact aatgctgatt   1380
gtgcctggct ggaagcacaa gaggaggaag aggaagtagg gtttccagtc agacctcagg   1440
tgccgctcag accaatgact tataaggggg cagtagatct cagcttcttt ttaaaagaaa   1500
aggggggact ggaagggtta acttactcta agaaaagaca agaaatcctt gatttgtggg   1560
tctatcacac acaaggctac ttccctgatt ggcaatgcta cacaccggga ccaggggtca   1620
gatacccact gacttttgga tggtgcttca agctagtgcc agttgaccca gatgaagtag   1680
gagaagccaa caatggagag aataactgtt tgctacaccc tataagcctg catggaatgg   1740
aggatccgtc gacttgacgc gttgatatca tctagagggc cctattctat agtgtcacct   1800
aaatgctaga gctcgctgat cagcctcgac tgtgccttct agttgccagc catctgttgt   1860
ttgcccctcc cccgtgcctt ccttgaccct ggaaggtgcc actcccactg tcctttccta   1920
ataaaatgag gaaattgcat cgcattgtct gagtaggtgt cattctattc tggggggtgg   1980
ggtggggcag gacagcaagg gggaggattg ggaagacaat agcaggcatg ctggggatgc   2040
ggtgggctct atggcttctg aggcggaaag aaccagctgg ggctctaggg ggtatcccca   2100
cgcgccctgt agcggcgcat taagcgcggc gggtgtggtg gttacgcgca gcgtgaccgc   2160
tacacttgcc agcgccctag cgcccgctcc tttcgctttc ttcccttcct ttctcgccac   2220
gttcgccggc tttccccgtc aagctctaaa tcggggcatc cctttagggt tccgatttag   2280
tgctttacgg cacctcgacc ccaaaaaact tgattagggt gatggttcac gtagtgggcc   2340
atcgccctga tagacggttt ttcgcccttt gacgttggag tccacgttct ttaatagtgg   2400
actcttgttc caaactggaa caacactcaa ccctatctcg gtctattctt ttgatttata   2460
agggattttg gggatttcgg cctattggtt aaaaaatgag ctgatttaac aaaaatttaa   2520
cgcgaattaa ttctgtggaa tgtgtgtcag ttagggtgtg gaaagtcccc aggctcccca   2580
ggcaggcaga agtatgcaaa gcatgcatct caattagtca gcaaccaggt gtggaaagtc   2640
cccaggctcc ccagcaggca gaagtatgca aagcatgcat ctcaattagt cagcaaccat   2700
agtcccgccc ctaactccgc ccatcccgcc cctaactccg cccagttccg cccattctcc   2760
gccccatggc tgactaattt tttttattta tgcagaggcc gaggccgcct ctgcctctga   2820
gctattccag aagtagtgag gaggcttttt tggaggccta ggcttttgca aaaagctccc   2880
gggagcttgt atatccattt tcggatctga tcaagagaca ggatgaggat cgtttcgcat   2940
gattgaacaa gatggattgc acgcaggttc tccggccgct tgggtggaga ggctattcgg   3000
ctatgactgg gcacaacaga caatcggctg ctctgatgcc gccgtgttcc ggctgtcagc   3060
gcaggggcgc ccggttcttt ttgtcaagac cgacctgtcc ggtgccctga atgaactgca   3120
ggacgaggca gcgcggctat cgtggctggc cacgacgggc gttccttgcg cagctgtgct   3180
cgacgttgtc actgaagcgg gaagggactg gctgctattg ggcgaagtgc cggggcagga   3240
tctcctgtca tctcaccttg ctcctgccga gaaagtatcc atcatggctg atgcaatgcg   3300
gcggctgcat acgcttgatc cggctacctg cccattcgac caccaagcga aacatcgcat   3360
cgagcgagca cgtactcgga tggaagccgg tcttgtcgat caggatgatc tggacgaaga   3420
```

-continued

```
gcatcagggg ctcgcgccag ccgaactgtt cgccaggctc aaggcgcgca tgcccgacgg   3480
cgaggatctc gtcgtgaccc atggcgatgc ctgcttgccg aatatcatgg tggaaaatgg   3540
ccgcttttct ggattcatcg actgtggccg gctgggtgtg gcggaccgct atcaggacat   3600
agcgttggct acccgtgata ttgctgaaga gcttggcggc gaatgggctg accgcttcct   3660
cgtgctttac ggtatcgccg ctcccgattc gcagcgcatc gccttctatc gccttcttga   3720
cgagttcttc tgagcgggac tctggggttc gaaatgaccg accaagcgac gcccaacctg   3780
ccatcacgag atttcgattc caccgccgcc ttctatgaaa ggttgggctt cggaatcgtt   3840
ttccgggacg ccggctggat gatcctccag cgcggggatc tcatgctgga gttcttcgcc   3900
caccccaact tgtttattgc agcttataat ggttacaaat aaagcaatag catcacaaat   3960
ttcacaaata aagcattttt ttcactgcat tctagttgtg gtttgtccaa actcatcaat   4020
gtatcttatc atgtctgtat accgtcgacc tctagctaga gcttggcgta atcatggtca   4080
tagctgtttc ctgtgtgaaa ttgttatccg ctcacaattc cacacaacat acgagccgga   4140
agcataaagt gtaaagcctg gggtgcctaa tgagtgagct aactcacatt aattgcgttg   4200
cgctcactgc ccgctttcca gtcgggaaac ctgtcgtgcc agctgcatta atgaatcggc   4260
caacgcgcgg ggagaggcgg tttgcgtatt gggcgctctt ccgcttcctc gctcactgac   4320
tcgctgcgct cggtcgttcg gctgcggcga gcggtatcag ctcactcaaa ggcggtaata   4380
cggttatcca cagaatcagg ggataacgca ggaaagaaca tgtgagcaaa aggccagcaa   4440
aaggccagga accgtaaaaa ggccgcgttg ctggcgtttt tccataggct ccgcccccct   4500
gacgagcatc acaaaaatcg acgctcaagt cagaggtggc gaaacccgac aggactataa   4560
agataccagg cgtttccccc tggaagctcc ctcgtgcgct ctcctgttcc gaccctgccg   4620
cttaccggat acctgtccgc ctttctccct tcgggaagcg tggcgctttc tcaatgctca   4680
cgctgtaggt atctcagttc ggtgtaggtc gttcgctcca agctgggctg tgtgcacgaa   4740
ccccccgttc agcccgaccg ctgcgcctta tccggtaact atcgtcttga gtccaacccg   4800
gtaagacacg acttatcgcc actggcagca gccactggta acaggattag cagagcgagg   4860
tatgtaggcg gtgctacaga gttcttgaag tggtggccta actacggcta cactagaagg   4920
acagtatttg gtatctgcgc tctgctgaag ccagttacct tcggaaaaag agttggtagc   4980
tcttgatccg gcaaacaaac caccgctggt agcggtggtt tttttgtttg caagcagcag   5040
attacgcgca gaaaaaaagg atctcaagaa gatcctttga tcttttctac ggggtctgac   5100
gctcagtgga acgaaaactc acgttaaggg attttggtca tgagattatc aaaaaggatc   5160
ttcacctaga tccttttaaa ttaaaaatga agttttaaat caatctaaag tatatatgag   5220
taaacttggt ctgacagtta ccaatgctta atcagtgagg cacctatctc agcgatctgt   5280
ctatttcgtt catccatagt tgcctgactc cccgtcgtgt agataactac gatacgggag   5340
ggcttaccat ctggccccag tgctgcaatg ataccgcgag acccacgctc accggctcca   5400
gatttatcag caataaacca gccagccgga agggccgagc gcagaagtgg tcctgcaact   5460
ttatccgcct ccatccagtc tattaattgt tgccgggaag ctagagtaag tagttcgcca   5520
gttaatagtt tgcgcaacgt tgttgccatt gctacaggca tcgtggtgtc acgctcgtcg   5580
tttggtatgg cttcattcag ctccggttcc caacgatcaa ggcgagttac atgatccccc   5640
atgttgtgca aaaaagcggt tagctccttc ggtcctccga tcgttgtcag aagtaagttg   5700
gccgcagtgt tatcactcat ggttatggca gcactgcata attctcttac tgtcatgcca   5760
```

-continued

```
tccgtaagat gcttttctgt gactggtgag tactcaacca agtcattctg agaatagtgt   5820

atgcggcgac cgagttgctc ttgcccggcg tcaatacggg ataataccgc gccacatagc   5880

agaactttaa aagtgctcat cattggaaaa cgttcttcgg ggcgaaaact ctcaaggatc   5940

ttaccgctgt tgagatccag ttcgatgtaa cccactcgtg cacccaactg atcttcagca   6000

tcttttactt tcaccagcgt ttctgggtga gcaaaaacag gaaggcaaaa tgccgcaaaa   6060

aagggaataa gggcgacacg gaaatgttga atactcatac tcttcctttt tcaatattat   6120

tgaagcattt atcagggtta ttgtctcatg agcggataca tatttgaatg tatttagaaa   6180

aataaacaaa taggggttcc gcgcacattt ccccgaaaag tgccacctga cgtc         6234


<210> SEQ ID NO 2
<211> LENGTH: 214
<212> TYPE: PRT
<213> ORGANISM: Artificial Sequence
<220> FEATURE:
<223> OTHER INFORMATION: Nef RP01

<400> SEQUENCE: 2

Met Lys Leu Leu Ser Ser Ile Glu Gln Ala Cys Pro Lys Lys Lys Arg
1               5                   10                  15

Lys Val Asp Glu Phe Pro Gly Ile Ser Thr Ala Pro Pro Thr Asp Val
            20                  25                  30

Ser Leu Gly Asp Glu Leu His Leu Asp Gly Glu Asp Val Ala Met Ala
        35                  40                  45

His Ala Asp Ala Leu Asp Asp Phe Asp Leu Asp Met Leu Gly Asp Gly
    50                  55                  60

Asp Ser Pro Gly Pro Gly Ser Pro Gly Ile Arg Gly Ala Leu Thr Ser
65                  70                  75                  80

Ser Asn Thr Ala Gln Thr Asn Ala Asp Cys Ala Trp Leu Glu Ala Gln
                85                  90                  95

Glu Glu Glu Glu Glu Val Gly Phe Pro Val Arg Pro Gln Val Pro Leu
            100                 105                 110

Arg Pro Met Thr Tyr Lys Gly Ala Val Asp Leu Ser Phe Phe Leu Lys
        115                 120                 125

Glu Lys Gly Gly Leu Glu Gly Leu Thr Tyr Ser Lys Lys Arg Gln Glu
    130                 135                 140

Ile Leu Asp Leu Trp Val Tyr His Thr Gln Gly Tyr Phe Pro Asp Trp
145                 150                 155                 160

Gln Cys Tyr Thr Pro Gly Pro Gly Val Arg Tyr Pro Leu Thr Phe Gly
                165                 170                 175

Trp Cys Phe Lys Leu Val Pro Val Asp Pro Asp Glu Val Gly Glu Ala
            180                 185                 190

Asn Asn Gly Glu Asn Asn Cys Leu Leu His Pro Ile Ser Leu His Gly
        195                 200                 205

Met Glu Asp Pro Ser Thr
    210


<210> SEQ ID NO 3
<211> LENGTH: 4955
<212> TYPE: DNA
<213> ORGANISM: Artificial Sequence
<220> FEATURE:
<223> OTHER INFORMATION: reporter construct pG5Luc

<400> SEQUENCE: 3

ggtaccgagt ttctagacgg agtactgtcc tccgagcgga gtactgtcct ccgactcgag     60
```

-continued

```
cggagtactg tcctccgatc ggagtactgt cctccgcgaa ttccggagta ctgtcctccg    120
aagacgctag cggggggcta taaaaggggg tgggggcgtt cgtcctcact ctagatctgc    180
gatctaagta agcttggcat tccggtactg ttggtaaagc caccatggaa gacgccaaaa    240
acataaagaa aggcccggcg ccattctatc cgctggaaga tggaaccgct ggagagcaac    300
tgcataaggc tatgaagaga tacgccctgg ttcctggaac aattgctttt acagatgcac    360
atatcgaggt ggacatcact tacgctgagt acttcgaaat gtccgttcgg ttggcagaag    420
ctatgaaacg atatgggctg aatacaaatc acagaatcgt cgtatgcagt gaaaactctc    480
ttcaattctt tatgccggtg ttgggcgcgt tatttatcgg agttgcagtt gcgcccgcga    540
acgacattta taatgaacgt gaattgctca acagtatggg catttcgcag cctaccgtgg    600
tgttcgtttc caaaaagggg ttgcaaaaaa ttttgaacgt gcaaaaaaag ctcccaatca    660
tccaaaaaat tattatcatg gattctaaaa cggattacca gggatttcag tcgatgtaca    720
cgttcgtcac atctcatcta cctcccggtt ttaatgaata cgattttgtg ccagagtcct    780
tcgataggga caagacaatt gcactgatca tgaactcctc tggatctact ggtctgccta    840
aaggtgtcgc tctgcctcat agaactgcct gcgtgagatt ctcgcatgcc agagatccta    900
tttttggcaa tcaaatcatt ccggatactg cgattttaag tgttgttcca ttccatcacg    960
gttttggaat gtttactaca ctcggatatt tgatatgtgg atttcgagtc gtcttaatgt   1020
atagatttga agaagagctg tttctgagga gccttcagga ttacaagatt caaagtgcgc   1080
tgctggtgcc aaccctattc tccttcttcg ccaaaagcac tctgattgac aaatacgatt   1140
tatctaattt acacgaaatt gcttctggtg gcgctcccct ctctaaggaa gtcggggaag   1200
cggttgccaa gaggttccat ctgccaggta tcaggcaagg atatgggctc actgagacta   1260
catcagctat tctgattaca cccgaggggg atgataaacc gggcgcggtc ggtaaagttg   1320
ttccattttt tgaagcgaag gttgtggatc tggataccgg gaaaacgctg ggcgttaatc   1380
aaagaggcga actgtgtgtg agaggtccta tgattatgtc cggttatgta aacaatccgg   1440
aagcgaccaa cgccttgatt gacaaggatg gatggctaca ttctggagac atagcttact   1500
gggacgaaga cgaacacttc ttcatcgttg accgcctgaa gtctctgatt aagtacaaag   1560
gctatcaggt ggctcccgct gaattggaat ccatcttgct ccaacacccc aacatcttcg   1620
acgcaggtgt cgcaggtctt cccgacgatg acgccggtga acttcccgcc gccgttgttg   1680
ttttggagca cggaaagacg atgacggaaa aagagatcgt ggattacgtc gccagtcaag   1740
taacaaccgc gaaaaagttg cgcggaggag ttgtgtttgt ggacgaagta ccgaaaggtc   1800
ttaccggaaa actcgacgca agaaaaatca gagagatcct cataaaggcc aagaagggcg   1860
gaaagatcgc cgtgtaattc tagagtcggg gcggccggcc gcttcgagca gacatgataa   1920
gatacattga tgagtttgga caaaccacaa ctagaatgca gtgaaaaaaa tgctttattt   1980
gtgaaatttg tgatgctatt gctttatttg taaccattat aagctgcaat aaacaagtta   2040
acaacaacaa ttgcattcat tttatgtttc aggttcaggg ggaggtgtgg gaggtttttt   2100
aaagcaagta aaacctctac aaatgtggta aaatcgataa ggatccgtcg accgatgccc   2160
ttgagagcct tcaacccagt cagctccttc cggtgggcgc ggggcatgac tatcgtcgcc   2220
gcacttatga ctgtcttctt tatcatgcaa ctcgtaggac aggtgccggc agcgctcttc   2280
cgcttcctcg ctcactgact cgctgcgctc ggtcgttcgg ctgcggcgag cggtatcagc   2340
tcactcaaag gcggtaatac ggttatccac agaatcaggg gataacgcag gaaagaacat   2400
```

-continued

```
gtgagcaaaa ggccagcaaa aggccaggaa ccgtaaaaag gccgcgttgc tggcgttttt   2460
ccataggctc cgcccccctg acgagcatca caaaaatcga cgctcaagtc agaggtggcg   2520
aaacccgaca ggactataaa gataccaggc gtttccccct ggaagctccc tcgtgcgctc   2580
tcctgttccg accctgccgc ttaccggata cctgtccgcc tttctccctt cgggaagcgt   2640
ggcgctttct caatgctcac gctgtaggta tctcagttcg gtgtaggtcg ttcgctccaa   2700
gctgggctgt gtgcacgaac cccccgttca gcccgaccgc tgcgccttat ccggtaacta   2760
tcgtcttgag tccaacccgg taagacacga cttatcgcca ctggcagcag ccactggtaa   2820
caggattagc agagcgaggt atgtaggcgg tgctacagag ttcttgaagt ggtggcctaa   2880
ctacggctac actagaagga cagtatttgg tatctgcgct ctgctgaagc cagttacctt   2940
cggaaaaaga gttggtagct cttgatccgg caaacaaacc accgctggta gcggtggttt   3000
ttttgtttgc aagcagcaga ttacgcgcag aaaaaaagga tctcaagaag atcctttgat   3060
cttttctacg gggtctgacg ctcagtggaa cgaaaactca cgttaaggga ttttggtcat   3120
gagattatca aaaaggatct tcacctagat ccttttaaat taaaaatgaa gttttaaatc   3180
aatctaaagt atatatgagt aaacttggtc tgacagttac caatgcttaa tcagtgaggc   3240
acctatctca gcgatctgtc tatttcgttc atccatagtt gcctgactcc ccgtcgtgta   3300
gataactacg atacgggagg gcttaccatc tggccccagt gctgcaatga taccgcgaga   3360
cccacgctca ccggctccag atttatcagc aataaaccag ccagccggaa gggccgagcg   3420
cagaagtggt cctgcaactt tatccgcctc catccagtct attaattgtt gccgggaagc   3480
tagagtaagt agttcgccag ttaatagttt gcgcaacgtt gttgccattg ctacaggcat   3540
cgtggtgtca cgctcgtcgt ttggtatggc ttcattcagc tccggttccc aacgatcaag   3600
gcgagttaca tgatccccca tgttgtgcaa aaaagcggtt agctccttcg gtcctccgat   3660
cgttgtcaga agtaagttgg ccgcagtgtt atcactcatg gttatggcag cactgcataa   3720
ttctcttact gtcatgccat ccgtaagatg cttttctgtg actggtgagt actcaaccaa   3780
gtcattctga gaatagtgta tgcggcgacc gagttgctct tgcccggcgt caatacggga   3840
taataccgcg ccacatagca gaactttaaa agtgctcatc attggaaaac gttcttcggg   3900
gcgaaaactc tcaaggatct taccgctgtt gagatccagt tcgatgtaac ccactcgtgc   3960
acccaactga tcttcagcat cttttacttt caccagcgtt tctgggtgag caaaaacagg   4020
aaggcaaaat gccgcaaaaa agggaataag ggcgacacgg aaatgttgaa tactcatact   4080
cttccttttt caatattatt gaagcattta tcagggttat tgtctcatga gcggatacat   4140
atttgaatgt atttagaaaa ataaacaaat aggggttccg cgcacatttc cccgaaaagt   4200
gccacctgac gcgccctgta gcggcgcatt aagcgcggcg ggtgtggtgg ttacgcgcag   4260
cgtgaccgct acacttgcca gcgccctagc gcccgctcct ttcgctttct tcccttcctt   4320
tctcgccacg ttcgccggct ttccccgtca agctctaaat cgggggctcc ctttagggtt   4380
ccgatttagt gctttacggc acctcgaccc caaaaaactt gattagggtg atggttcacg   4440
tagtgggcca tcgccctgat agacggtttt tcgccctttg acgttggagt ccacgttctt   4500
taatagtgga ctcttgttcc aaactggaac aacactcaac cctatctcgg tctattcttt   4560
tgatttataa gggattttgc cgatttcggc ctattggtta aaaaatgagc tgatttaaca   4620
aaaatttaac gcgaatttta acaaaatatt aacgtttaca atttcccatt cgccattcag   4680
gctgcgcaac tgttgggaag ggcgatcggt gcgggcctct tcgctattac gccagcccaa   4740
gctaccatga taagtaagta atattaaggt acgggaggta cttggagcgg ccgcaataaa   4800
```

atatctttat tttcattaca tctgtgtgtt ggttttttgt gtgaatcgat agtactaaca 4860
tacgctctcc atcaaaacaa aacgaaacaa aacaaactag caaaataggc tgtccccagt 4920
gcaagtgcag gtgccagaac atttctctat cgata 4955

<210> SEQ ID NO 4
<211> LENGTH: 7368
<212> TYPE: DNA
<213> ORGANISM: Artificial Sequence
<220> FEATURE:
<223> OTHER INFORMATION: construct sequence containing ASK1(a) cloned in pBIND

<400> SEQUENCE: 4
tcaatattgg ccattagcca tattattcat tggttatata gcataaatca atattggcta 60
ttggccattg catacgttgt atctatatca taatatgtac atttatattg gctcatgtcc 120
aatatgaccg ccatgttggc attgattatt gactagttat taatagtaat caattacggg 180
gtcattagtt catagcccat atatggagtt ccgcgttaca taacttacgg taaatggccc 240
gcctggctga ccgcccaacg acccccgccc attgacgtca ataatgacgt atgttcccat 300
agtaacgcca atagggactt tccattgacg tcaatgggtg gagtatttac ggtaaactgc 360
ccacttggca gtacatcaag tgtatcatat gccaagtccg ccccctattg acgtcaatga 420
cggtaaatgg cccgcctggc attatgccca gtacatgacc ttacgggact ttcctacttg 480
gcagtacatc tacgtattag tcatcgctat taccatggtg atgcggtttt ggcagtacac 540
caatgggcgt ggatagcggt ttgactcacg gggatttcca agtctccacc ccattgacgt 600
caatgggagt ttgttttggc accaaaatca acgggacttt ccaaaatgtc gtaacaactg 660
cgatcgcccg ccccgttgac gcaaatgggc ggtaggcgtg tacggtggga ggtctatata 720
agcagagctc gtttagtgaa ccgtcagatc actagaagct ttattgcggt agtttatcac 780
agttaaattg ctaacgcagt cagtgcttct gacacaacag tctcgaactt aagctgcagt 840
gactctctta aggtagcctt gcagaagttg gtcgtgaggc actgggcagg taagtatcaa 900
ggttacaaga caggtttaag gagaccaata gaaactgggc ttgtcgagac agagaagact 960
cttgcgtttc tgataggcac ctattggtct tactgacatc cactttgcct ttctctccac 1020
aggtgtccac tcccagttca attacagctc ttaaggctag agtacttaat acgactcact 1080
ataggctagc cagcttgaag caagcctcct gaaagatgaa gctactgtct tctatcgaac 1140
aagcatgcga tatttgccga cttaaaaagc tcaagtgctc caaagaaaaa ccgaagtgcg 1200
ccaagtgtct gaagaacaac tgggagtgtc gctactctcc caaaaccaaa aggtctccgc 1260
tgactagggc acatctgaca gaagtggaat caaggctaga aagactggaa cagctatttc 1320
tactgatttt tcctcgagaa gaccttgaca tgattttgaa aatggattct ttacaggata 1380
taaaagcatt gttaacagga ttatttgtac aagataatgt gaataaagat gccgtcacag 1440
atagattggc ttcagtggag actgatatgc ctctaacatt gagacagcat agaataagtg 1500
cgacatcatc atcggaagag agtagtaaca aaggtcaaag acagttgact gtatcgccgg 1560
aattcccggg gatccgtacg gaggcggacg agggcatcac tttctctgtg ccacccttcg 1620
ccccctcggg cttctgcacc atccccgagg gcggcatctg caggagggga ggagcggcgg 1680
cggtgggcga gggcgaggag caccagctgc caccgccgcc gccgggcagt ttctggaacg 1740
tggagagcgc cgctgcccct ggcatcggtt gtccggcggc cacctcctcg agcagtgcca 1800
cccgaggccg gggcagctct gttggcgggg gcagccgacg gaccacggtg gcatatgtga 1860

-continued

```
tcaacgaagc gagccaaggg caactggtgg tggccgagag cgaggccctg cagagcttgc   1920

gggaggcgtg cgagacagtg ggcgccaccc tggaaaccct gcattttggg aaactcgact   1980

ttggagaaac caccgtgctg gaccgctttt acaatgcaga tattgcggtg gtggagatga   2040

gcgatgcctt ccggcagccg tccttgtttt accaccttgg ggtgagagaa agtttcagca   2100

tggccaacaa catcatcctc tactgtgata ctaactcgga ctctctgcag tcactgaagg   2160

aaatcatttg ccagaagaat actatgtgca ctgggaacta cacctttgtt ccttacatga   2220

taactccaca taacaaagtc tactgctgtg acagcagctt catgaagggg ttgacagagc   2280

tcatgcaacc gaacttcgag ctgcttcttg gacccatctg cttacctctt gtggatcgtt   2340

ttattcaact tttgaaggtg gcacaagcaa gttctagcca gtacttccgg gaatctatac   2400

tcaatgacat caggaaagct cgtaatttat acactggtaa agaattggca gctgagttgg   2460

caagaattcg gcagcgagta gataatatcg aagtcttgac agcagatatt gtcataaatc   2520

tgttactttc ctacagagat atccaggact atgattctat tgtgaagctg gtagagactt   2580

tagaaaaact gccaaccttt gatttgtcta gagcggccgc aggtacctga ataactaagg   2640

ccgcttccct ttagtgaggg ttaatgcttc gagcagacat gataagatac attgatgagt   2700

ttggacaaac cacaactaga atgcagtgaa aaaaatgctt tatttgtgaa atttgtgatg   2760

ctattgcttt atttgtaacc attataagct gcaataaaca agttaacaac aacaattgca   2820

ttcattttat gtttcaggtt cagggggaga tgtgggaggt tttttaaagc aagtaaaacc   2880

tctacaaatg tggtaaaatc cgataaggat cgatccgggc tggcgtaata gcgaagaggc   2940

ccgcaccgat cgcccttccc aacagttgcg cagcctgaat ggcgaatgga cgcgccctgt   3000

agcggcgcat taagcgcggc gggtgtggtg gttacgcgca gcgtgaccgc tacacttgcc   3060

agcgccctag cgcccgctcc tttcgctttc ttcccttcct ttcacgccac gttcgccggc   3120

tttccccgtc aagctctaaa tcgggggctc cctttagggt tccgatttag tgctttacgg   3180

cacctcgacc ccaaaaaact tgattagggt gatggttcac gtagtgggcc atcgccctga   3240

tagacggttt ttcgcccttt gacgttggag tccacgttct ttaatagtgg actcttgttc   3300

caaactggaa caacactcaa ccctatctcg gtctattctt ttgatttata agggattttg   3360

ccgatttcgg cctattggtt aaaaaatgag ctgatttaac aaaaatttaa cgcgaatttt   3420

aacaaaatat taacgcttac aatttcctga tgcggtattt tctccttacg catctgtgcg   3480

gtatttcaca ccgcatacgc ggatcttccg taccttctga ggcggaaaga accagctgtg   3540

gaatgtgtgt cagttagggt gtggaaagtc cccaggctcc ccagcaggca gaagtatgca   3600

aagcatgcat ctcaattagt cagcaaccag gtgtggaaag tccccaggct ccccagcagg   3660

cagaagtatg caaagcatgc atctcaatta gtcagcaacc atagtcccgc ccctaactcc   3720

gcccatcccg cccctaactc cgcccagttc cgcccattct ccgccccatg gctgactaat   3780

ttttttttatt tatgcagagg ccgaggccgc ctcggcctct gagctattcc agaagtagtg   3840

aggaggcttt tttggaggcc taggcttttg caaaaagctt gattcttctg acacaacagt   3900

ctcgaactta aggctagaat tctggctaca ggtaagcgcc cctaaaatcc ctttgggcac   3960

aatgtgtcct gaggggagag gcagcgacct gtagatggga cgggggcact aaccctcagg   4020

tttggggctt ctgaatgtga gtatcgccat gtaagcccag tatttggcca atctcagaaa   4080

gctcctggtc cctggaggga tggagagaga aaaacaaaca gctcctggag cagggagagt   4140

gctggcctct tgctctccgg ctccctctgt tgccctctgg tttctcccca ggctcccgga   4200
```

-continued

```
cgtcctctag ccaccatgac ttcgaaagtt tatgatccag aacaaaggaa acggatgata   4260
actggtccgc agtggtgggc cagatgtaaa caaatgaatg ttcttgattc atttattaat   4320
tattatgatt cagaaaaaca tgcagaaaat gctgttattt ttttacatgg taacgcggcc   4380
tcttcttatt tatggcgaca tgttgtgcca catattgagc cagtagcgcg gtgtattata   4440
ccagacctta ttggtatggg caaatcaggc aaatctggta atggttctta taggttactt   4500
gatcattaca aatatcttac tgcatggttt gaacttctta atttaccaaa gaagatcatt   4560
tttgtcggcc atgattgggg tgcttgtttg gcatttcatt atagctatga gcatcaagat   4620
aagatcaaag caatagttca cgctgaaagt gtagtagatg tgattgaatc atgggatgaa   4680
tggcctgata ttgaagaaga tattgcgttg atcaaatctg aagaaggaga aaaaatggtt   4740
ttggagaata acttcttcgt ggaaaccatg ttgccatcaa aaatcatgag aaagttagaa   4800
ccagaagaat ttgcagcata tcttgaacca ttcaaagaga aaggtgaagt tcgtcgtcca   4860
acattatcat ggcctcgtga aatcccgtta gtaaaaggtg gtaaacctga cgttgtacaa   4920
attgttagga attataatgc ttatctacgt gcaagtgatg atttaccaaa aatgtttatt   4980
gaatcggacc caggattctt ttccaatgct attgttgaag gtgccaagaa gtttcctaat   5040
actgaatttg tcaaagtaaa aggtcttcat ttttcgcaag aagatgcacc tgatgaaatg   5100
ggaaaatata tcaaatcgtt cgttgagcga gttctcaaaa atgaacaata attctagccc   5160
tgaataagtg ataataagcg gatgaatggc agaaattcgt cgaagcgcaa taaaatatct   5220
ttattttcat tacatctgtg tgttggtttt ttgtgtgaat cgatagcgat aaggatcgga   5280
agatccgcgt atggtgcact ctcagtacaa tctgctctga tgccgcatag ttaagccagc   5340
cccgacaccc gccaacaccc gctgacgcgc cctgacgggc ttgtctgctc ccggcatccg   5400
cttacagaca agctgtgacc gtctccggga gctgcatgtg tcagaggttt tcaccgtcat   5460
caccgaaacg cgcgagacga aagggcctcg tgatacgcct atttttatag gttaatgtca   5520
tgataataat ggtttcttag acgtcaggtg gcacttttcg gggaaatgtg cgcggaaccc   5580
ctatttgttt atttttctaa atacattcaa atatgtatcc gctcatgaga caataaccct   5640
gataaatgct tcaataatat tgaaaaagga agagtatgag tattcaacat ttccgtgtcg   5700
cccttattcc cttttttgcg gcattttgcc ttcctgtttt tgctcaccca gaaacgctgg   5760
tgaaagtaaa agatgctgaa gatcagttgg gtgcacgagt gggttacatc gaactggatc   5820
tcaacagcgg taagatcctt gagagttttc gccccgaaga acgttttcca atgatgagca   5880
cttttaaagt tctgctatgt ggcgcggtat tatcccgtgt tgacgccggg caagagcaac   5940
tcggtcgccg catacactat tctcagaatg acttggttga gtactcacca gtcacagaaa   6000
agcatcttac ggatggcatg acagtaagag aattatgcag tgctgccata accatgagtg   6060
ataacactgc ggccaactta cttctgacaa cgatcggagg accgaaggag ctaaccgctt   6120
ttttgcacaa catgggggat catgtaactc gccttgatcg ttgggaaccg gagctgaatg   6180
aagccatacc aaacgacgag cgtgacacca cgatgcctgt agcaatggca acaacgttgc   6240
gcaaactatt aactggcgaa ctacttactc tagcttcccg gcaacaatta atagactgga   6300
tggaggcgga taaagttgca ggaccacttc tgcgctcggc ccttccggct ggctggttta   6360
ttgctgataa atctggagcc ggtgagcgtg ggtctcgcgg tatcattgca gcactggggc   6420
cagatggtaa gccctcccgt atcgtagtta tctacacgac ggggagtcag gcaactatgg   6480
atgaacgaaa tagacagatc gctgagatag gtgcctcact gattaagcat tggtaactgt   6540
cagaccaagt ttactcatat atactttaga ttgatttaaa acttcatttt taatttaaaa   6600
```

-continued

```
ggatctaggt gaagatcctt tttgataatc tcatgaccaa aatcccttaa cgtgagtttt   6660

cgttccactg agcgtcagac cccgtagaaa agatcaaagg atcttcttga gatccttttt   6720

ttctgcgcgt aatctgctgc ttgcaaacaa aaaaaccacc gctaccagcg gtggtttgtt   6780

tgccggatca agagctacca actctttttc cgaaggtaac tggcttcagc agagcgcaga   6840

taccaaatac tgttcttcta gtgtagccgt agttaggcca ccacttcaag aactctgtag   6900

caccgcctac atacctcgct ctgctaatcc tgttaccagt ggctgctgcc agtggcgata   6960

agtcgtgtct taccgggttg gactcaagac gatagttacc ggataaggcg cagcggtcgg   7020

gctgaacggg gggttcgtgc acacagccca gcttggagcg aacgacctac accgaactga   7080

gatacctaca gcgtgagcta tgagaaagcg ccacgcttcc cgaagggaga aaggcggaca   7140

ggtatccggt aagcggcagg gtcggaacag gagagcgcac gagggagctt ccagggggaa   7200

acgcctggta tctttatagt cctgtcgggt ttcgccacct ctgacttgag cgtcgatttt   7260

tgtgatgctc gtcagggggg cggagcctat ggaaaaacgc cagcaacgcg gcctttttac   7320

ggttcctggc cttttgctgg ccttttgctc acatggctcg acagatct                 7368


<210> SEQ ID NO 5
<211> LENGTH: 499
<212> TYPE: PRT
<213> ORGANISM: Artificial Sequence
<220> FEATURE:
<223> OTHER INFORMATION: Gal4 ASK1 (a) fusion protein sequence

<400> SEQUENCE: 5

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Pro Glu Phe Pro Gly Ile Arg Thr Glu Ala Asp Glu Gly
145                 150                 155                 160

Ile Thr Phe Ser Val Pro Pro Phe Ala Pro Ser Gly Phe Cys Thr Ile
                165                 170                 175

Pro Glu Gly Gly Ile Cys Arg Arg Gly Gly Ala Ala Ala Val Gly Glu
            180                 185                 190

Gly Glu Glu His Gln Leu Pro Pro Pro Pro Pro Gly Ser Phe Trp Asn
        195                 200                 205

Val Glu Ser Ala Ala Ala Pro Gly Ile Gly Cys Pro Ala Ala Thr Ser
    210                 215                 220
```

-continued

```
Ser Ser Ser Ala Thr Arg Gly Arg Gly Ser Ser Val Gly Gly Gly Ser
225                 230                 235                 240

Arg Arg Thr Thr Val Ala Tyr Val Ile Asn Glu Ala Ser Gln Gly Gln
                245                 250                 255

Leu Val Val Ala Glu Ser Glu Ala Leu Gln Ser Leu Arg Glu Ala Cys
            260                 265                 270

Glu Thr Val Gly Ala Thr Leu Glu Thr Leu His Phe Gly Lys Leu Asp
        275                 280                 285

Phe Gly Glu Thr Thr Val Leu Asp Arg Phe Tyr Asn Ala Asp Ile Ala
    290                 295                 300

Val Val Glu Met Ser Asp Ala Phe Arg Gln Pro Ser Leu Phe Tyr His
305                 310                 315                 320

Leu Gly Val Arg Glu Ser Phe Ser Met Ala Asn Asn Ile Ile Leu Tyr
                325                 330                 335

Cys Asp Thr Asn Ser Asp Ser Leu Gln Ser Leu Lys Glu Ile Ile Cys
            340                 345                 350

Gln Lys Asn Thr Met Cys Thr Gly Asn Tyr Thr Phe Val Pro Tyr Met
        355                 360                 365

Ile Thr Pro His Asn Lys Val Tyr Cys Cys Asp Ser Ser Phe Met Lys
    370                 375                 380

Gly Leu Thr Glu Leu Met Gln Pro Asn Phe Glu Leu Leu Leu Gly Pro
385                 390                 395                 400

Ile Cys Leu Pro Leu Val Asp Arg Phe Ile Gln Leu Leu Lys Val Ala
                405                 410                 415

Gln Ala Ser Ser Ser Gln Tyr Phe Arg Glu Ser Ile Leu Asn Asp Ile
            420                 425                 430

Arg Lys Ala Arg Asn Leu Tyr Thr Gly Lys Glu Leu Ala Ala Glu Leu
        435                 440                 445

Ala Arg Ile Arg Gln Arg Val Asp Asn Ile Glu Val Leu Thr Ala Asp
    450                 455                 460

Ile Val Ile Asn Leu Leu Leu Ser Tyr Arg Asp Ile Gln Asp Tyr Asp
465                 470                 475                 480

Ser Ile Val Lys Leu Val Glu Thr Leu Glu Lys Leu Pro Thr Phe Asp
                485                 490                 495

Leu Ser Arg
```

<210> SEQ ID NO 6
<211> LENGTH: 7368
<212> TYPE: DNA
<213> ORGANISM: Artificial Sequence
<220> FEATURE:
<223> OTHER INFORMATION: construct sequence containing ASK1(b) cloned in pBIND

<400> SEQUENCE: 6

```
tcaatattgg ccattagcca tattattcat tggttatata gcataaatca atattggcta     60

ttggccattg catacgttgt atctatatca taatatgtac atttatattg gctcatgtcc    120

aatatgaccg ccatgttggc attgattatt gactagttat taatagtaat caattacggg    180

gtcattagtt catagcccat atatggagtt ccgcgttaca taacttacgg taaatggccc    240

gcctggctga ccgcccaacg acccccgccc attgacgtca ataatgacgt atgttcccat    300

agtaacgcca atagggactt tccattgacg tcaatgggtg gagtatttac ggtaaactgc    360

ccacttggca gtacatcaag tgtatcatat gccaagtccg ccccctattg acgtcaatga    420

cggtaaatgg cccgcctggc attatgccca gtacatgacc ttacgggact ttcctacttg    480
```

-continued

```
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt ttgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaggctag agtacttaat acgactcact   1080
ataggctagc cagcttgaag caagcctcct gaaagatgaa gctactgtct tctatcgaac   1140
aagcatgcga tatttgccga cttaaaaagc tcaagtgctc caaagaaaaa ccgaagtgcg   1200
ccaagtgtct gaagaacaac tgggagtgtc gctactctcc caaaaccaaa aggtctccgc   1260
tgactagggc acatctgaca gaagtggaat caaggctaga aagactggaa cagctatttc   1320
tactgatttt tcctcgagaa gaccttgaca tgattttgaa aatggattct ttacaggata   1380
taaaagcatt gttaacagga ttatttgtac aagataatgt gaataaagat gccgtcacag   1440
atagattggc ttcagtggag actgatatgc ctctaacatt gagacagcat agaataagtg   1500
cgacatcatc atcggaagag agtagtaaca aaggtcaaag acagttgact gtatcgccgg   1560
aattcccggg gatccgtacg gaggcggacg agggcatcac tttctctgtg ccacccttcg   1620
cccccctcggg cttctgcacc atccccgagg gcggcatctg caggagggga ggagcggcgg   1680
cggtgggcga gggcgaggag caccagctgc caccgccgcc gccgggcagt ttctggaacg   1740
tggagagcgc cgctgcccct ggcatcggtt gtccggcggc cacctcctcg agcagtgcca   1800
cccgaggccg gggcagctct gttggcgggg gcagccgacg gaccacggtg gcatatgtga   1860
tcaacgaagc gagccaaggg caactggtgg tggccgagag cgaggccctg cagagcttgc   1920
gggaggcgtg cgagacagtg ggcgccaccc tggaaaccct gcattttggg aaactcgact   1980
ttggagaaac caccgtgctg gaccgctttt acaatgcaga tattgcggtg gtggagatga   2040
gcgatgcctt ccggcagccg tccttgtttt accaccttgg ggtgagagaa agtttcagca   2100
tggccaacaa catcatcctc tactgtgata ctaactcgga ctctctgcag tcactgaagg   2160
aaatcatttg ccagaagaat actatgtgca ctgggaacta cacctttgtt ccttacatga   2220
taactccaca taacaaagtc tactgctgtg acagcagctt catgaagggg ttgacagagc   2280
tcatgcaacc gaacttcgag ctgcttcttg gacccatctg cttacctctt gtggatcgtt   2340
ttattcaact tttgaaggtg gcacaagcaa gttctagcca gtacttccgg gaatctatac   2400
tcaatgacat caggaaagct cgtaatttat acactggtaa agaattggca gctgagttgg   2460
caagaattcg gcagcgagta gataatatcg aagtcttgac agcagatatt gtcataaatc   2520
tgttactttc ctacagagat atccaggact atgattctat tgtgaagctg gtagagactt   2580
tagaaaaact gccaaccttt gatttgtcta gagcggccgc aggtacctga ataactaagg   2640
ccgcttccct ttagtgaggg ttaatgcttc gagcagacat gataagatac attgatgagt   2700
ttggacaaac cacaactaga atgcagtgaa aaaaatgctt tatttgtgaa atttgtgatg   2760
ctattgcttt atttgtaacc attataagct gcaataaaca agttaacaac aacaattgca   2820
```

-continued

```
ttcattttat gtttcaggtt cagggggaga tgtgggaggt tttttaaagc aagtaaaacc   2880
tctacaaatg tggtaaaatc cgataaggat cgatccgggc tggcgtaata gcgaagaggc   2940
ccgcaccgat cgcccttccc aacagttgcg cagcctgaat ggcgaatgga cgcgccctgt   3000
agcggcgcat taagcgcggc gggtgtggtg gttacgcgca gcgtgaccgc tacacttgcc   3060
agcgccctag cgcccgctcc tttcgctttc ttcccttcct ttcacgccac gttcgccggc   3120
tttccccgtc aagctctaaa tcgggggctc cctttagggt tccgatttag tgctttacgg   3180
cacctcgacc ccaaaaaact tgattagggt gatggttcac gtagtgggcc atcgccctga   3240
tagacggttt ttcgcccttt gacgttggag tccacgttct ttaatagtgg actcttgttc   3300
caaactggaa caacactcaa ccctatctcg gtctattctt ttgatttata agggattttg   3360
ccgatttcgg cctattggtt aaaaaatgag ctgatttaac aaaaatttaa cgcgaatttt   3420
aacaaaatat taacgcttac aatttcctga tgcggtattt tctccttacg catctgtgcg   3480
gtatttcaca ccgcatacgc ggatcttccg taccttctga ggcggaaaga accagctgtg   3540
gaatgtgtgt cagttagggt gtggaaagtc cccaggctcc ccagcaggca gaagtatgca   3600
aagcatgcat ctcaattagt cagcaaccag gtgtggaaag tccccaggct ccccagcagg   3660
cagaagtatg caaagcatgc atctcaatta gtcagcaacc atagtcccgc ccctaactcc   3720
gcccatcccg cccctaactc cgcccagttc cgcccattct ccgccccatg gctgactaat   3780
ttttttttatt tatgcagagg ccgaggccgc ctcggcctct gagctattcc agaagtagtg   3840
aggaggcttt tttggaggcc taggcttttg caaaaagctt gattcttctg acacaacagt   3900
ctcgaactta aggctagaat tctggctaca ggtaagcgcc cctaaaatcc ctttgggcac   3960
aatgtgtcct gaggggagag gcagcgacct gtagatggga cgggggcact aaccctcagg   4020
tttggggctt ctgaatgtga gtatcgccat gtaagcccag tatttggcca atctcagaaa   4080
gctcctggtc cctggaggga tggagagaga aaaacaaaca gctcctggag cagggagagt   4140
gctggcctct tgctctccgg ctccctctgt tgccctctgg tttctcccca ggctcccgga   4200
cgtcctctag ccaccatgac ttcgaaagtt tatgatccag aacaaaggaa acggatgata   4260
actggtccgc agtggtgggc cagatgtaaa caaatgaatg ttcttgattc atttattaat   4320
tattatgatt cagaaaaaca tgcagaaaat gctgttattt ttttacatgg taacgcggcc   4380
tcttcttatt tatggcgaca tgttgtgcca catattgagc cagtagcgcg gtgtattata   4440
ccagacctta ttggtatggg caaatcaggc aaatctggta atggttctta taggttactt   4500
gatcattaca aatatcttac tgcatggttt gaacttctta atttaccaaa gaagatcatt   4560
tttgtcggcc atgattgggg tgcttgtttg gcatttcatt atagctatga gcatcaagat   4620
aagatcaaag caatagttca cgctgaaagt gtagtagatg tgattgaatc atgggatgaa   4680
tggcctgata ttgaagaaga tattgcgttg atcaaatctg aagaaggaga aaaaatggtt   4740
ttggagaata acttcttcgt ggaaaccatg ttgccatcaa aaatcatgag aaagttagaa   4800
ccagaagaat ttgcagcata tcttgaacca ttcaaagaga aaggtgaagt tcgtcgtcca   4860
acattatcat ggcctcgtga aatcccgtta gtaaaaggtg gtaaacctga cgttgtacaa   4920
attgttagga attataatgc ttatctacgt gcaagtgatg atttaccaaa aatgtttatt   4980
gaatcggacc caggattctt ttccaatgct attgttgaag gtgccaagaa gtttcctaat   5040
actgaatttg tcaaagtaaa aggtcttcat ttttcgcaag aagatgcacc tgatgaaatg   5100
ggaaaatata tcaaatcgtt cgttgagcga gttctcaaaa atgaacaata attctagccc   5160
tgaataagtg ataataagcg gatgaatggc agaaattcgt cgaagcgcaa taaaatatct   5220
```

-continued

```
ttattttcat tacatctgtg tgttggtttt ttgtgtgaat cgatagcgat aaggatcgga   5280

agatccgcgt atggtgcact ctcagtacaa tctgctctga tgccgcatag ttaagccagc   5340

cccgacaccc gccaacaccc gctgacgcgc cctgacgggc ttgtctgctc ccggcatccg   5400

cttacagaca agctgtgacc gtctccggga gctgcatgtg tcagaggttt tcaccgtcat   5460

caccgaaacg cgcgagacga aagggcctcg tgatacgcct atttttatag gttaatgtca   5520

tgataataat ggtttcttag acgtcaggtg gcacttttcg gggaaatgtg cgcggaaccc   5580

ctatttgttt atttttctaa atacattcaa atatgtatcc gctcatgaga caataaccct   5640

gataaatgct tcaataatat tgaaaaagga agagtatgag tattcaacat ttccgtgtcg   5700

cccttattcc cttttttgcg gcattttgcc ttcctgtttt tgctcaccca gaaacgctgg   5760

tgaaagtaaa agatgctgaa gatcagttgg gtgcacgagt gggttacatc gaactggatc   5820

tcaacagcgg taagatcctt gagagttttc gccccgaaga acgttttcca atgatgagca   5880

cttttaaagt tctgctatgt ggcgcggtat tatcccgtgt tgacgccggg caagagcaac   5940

tcggtcgccg catacactat tctcagaatg acttggttga gtactcacca gtcacagaaa   6000

agcatcttac ggatggcatg acagtaagag aattatgcag tgctgccata accatgagtg   6060

ataacactgc ggccaactta cttctgacaa cgatcggagg accgaaggag ctaaccgctt   6120

ttttgcacaa catgggggat catgtaactc gccttgatcg ttgggaaccg gagctgaatg   6180

aagccatacc aaacgacgag cgtgacacca cgatgcctgt agcaatggca acaacgttgc   6240

gcaaactatt aactggcgaa ctacttactc tagcttcccg gcaacaatta atagactgga   6300

tggaggcgga taaagttgca ggaccacttc tgcgctcggc ccttccggct ggctggttta   6360

ttgctgataa atctggagcc ggtgagcgtg ggtctcgcgg tatcattgca gcactggggc   6420

cagatggtaa gccctcccgt atcgtagtta tctacacgac ggggagtcag gcaactatgg   6480

atgaacgaaa tagacagatc gctgagatag gtgcctcact gattaagcat tggtaactgt   6540

cagaccaagt ttactcatat atactttaga ttgatttaaa acttcatttt taatttaaaa   6600

ggatctaggt gaagatcctt tttgataatc tcatgaccaa aatcccttaa cgtgagtttt   6660

cgttccactg agcgtcagac cccgtagaaa agatcaaagg atcttcttga gatccttttt   6720

ttctgcgcgt aatctgctgc ttgcaaacaa aaaaaccacc gctaccagcg gtggtttgtt   6780

tgccggatca agagctacca actctttttc cgaaggtaac tggcttcagc agagcgcaga   6840

taccaaatac tgttcttcta gtgtagccgt agttaggcca ccacttcaag aactctgtag   6900

caccgcctac atacctcgct ctgctaatcc tgttaccagt ggctgctgcc agtggcgata   6960

agtcgtgtct taccgggttg gactcaagac gatagttacc ggataaggcg cagcggtcgg   7020

gctgaacggg gggttcgtgc acacagccca gcttggagcg aacgacctac accgaactga   7080

gatacctaca gcgtgagcta tgagaaagcg ccacgcttcc cgaagggaga aaggcggaca   7140

ggtatccggt aagcggcagg gtcggaacag gagagcgcac gagggagctt ccagggggaa   7200

acgcctggta tctttatagt cctgtcgggt ttcgccacct ctgacttgag cgtcgatttt   7260

tgtgatgctc gtcagggggg cggagcctat ggaaaaacgc cagcaacgcg gcctttttac   7320

ggttcctggc cttttgctgg ccttttgctc acatggctcg acagatct                7368
```

<210> SEQ ID NO 7
<211> LENGTH: 505
<212> TYPE: PRT
<213> ORGANISM: Artificial Sequence
<220> FEATURE:

<223> OTHER INFORMATION: Gal4 ASK1(b) fusion protein sequence

<400> SEQUENCE: 7

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Pro Glu Phe Pro Gly Ile Arg Ser Tyr Arg Asp Ile Gln
145                 150                 155                 160

Asp Tyr Asp Ser Ile Val Lys Leu Val Glu Thr Leu Glu Lys Leu Pro
                165                 170                 175

Thr Phe Asp Leu Ala Ser His His His Val Lys Phe His Tyr Ala Phe
            180                 185                 190

Ala Leu Asn Arg Arg Asn Leu Pro Gly Asp Arg Ala Lys Ala Leu Asp
        195                 200                 205

Ile Met Ile Pro Met Val Gln Ser Glu Gly Gln Val Ala Ser Asp Met
    210                 215                 220

Tyr Cys Leu Val Gly Arg Ile Tyr Lys Asp Met Phe Leu Asp Ser Asn
225                 230                 235                 240

Phe Thr Asp Thr Glu Ser Arg Asp His Gly Ala Ser Trp Phe Lys Lys
                245                 250                 255

Ala Phe Glu Ser Glu Pro Thr Leu Gln Ser Gly Ile Asn Tyr Ala Val
            260                 265                 270

Leu Leu Leu Ala Ala Gly His Gln Phe Glu Ser Ser Phe Glu Leu Arg
        275                 280                 285

Lys Val Gly Val Lys Leu Ser Ser Leu Leu Gly Lys Lys Gly Asn Leu
    290                 295                 300

Glu Lys Leu Gln Ser Tyr Trp Glu Val Gly Phe Phe Leu Gly Ala Ser
305                 310                 315                 320

Val Leu Ala Asn Asp His Met Arg Val Ile Gln Ala Ser Glu Lys Leu
                325                 330                 335

Phe Lys Leu Lys Thr Pro Ala Trp Tyr Leu Lys Ser Ile Val Glu Thr
            340                 345                 350

Ile Leu Ile Tyr Lys His Phe Val Lys Leu Thr Thr Glu Gln Pro Val
        355                 360                 365

Ala Lys Gln Glu Leu Val Asp Phe Trp Met Asp Phe Leu Val Glu Ala
    370                 375                 380

Thr Lys Thr Asp Val Thr Val Val Arg Phe Pro Val Leu Ile Leu Glu
385                 390                 395                 400
```

-continued

```
Pro Thr Lys Ile Tyr Gln Pro Ser Tyr Leu Ser Ile Asn Asn Glu Val
                405                 410                 415

Glu Glu Lys Thr Ile Ser Ile Trp His Val Leu Pro Asp Asp Lys Lys
            420                 425                 430

Gly Ile His Glu Trp Asn Phe Ser Ala Ser Ser Val Arg Gly Val Ser
        435                 440                 445

Ile Ser Lys Phe Glu Glu Arg Cys Cys Phe Leu Tyr Val Leu His Asn
    450                 455                 460

Ser Asp Asp Phe Gln Ile Tyr Phe Cys Thr Glu Leu His Cys Lys Lys
465                 470                 475                 480

Phe Phe Glu Met Val Asn Thr Ile Thr Glu Glu Lys Gly Arg Ser Thr
                485                 490                 495

Glu Glu Gly Asp Cys Glu Ser Asp Leu
            500                 505


<210> SEQ ID NO 8
<211> LENGTH: 7239
<212> TYPE: DNA
<213> ORGANISM: Artificial Sequence
<220> FEATURE:
<223> OTHER INFORMATION: construct sequence containing ASK1(c) cloned in
      pBIND

<400> SEQUENCE: 8

tcaatattgg ccattagcca tattattcat tggttatata gcataaatca atattggcta     60

ttggccattg catacgttgt atctatatca taatatgtac atttatattg gctcatgtcc    120

aatatgaccg ccatgttggc attgattatt gactagttat taatagtaat caattacggg    180

gtcattagtt catagcccat atatggagtt ccgcgttaca taacttacgg taaatggccc    240

gcctggctga ccgcccaacg acccccgccc attgacgtca ataatgacgt atgttcccat    300

agtaacgcca atagggactt tccattgacg tcaatgggtg gagtatttac ggtaaactgc    360

ccacttggca gtacatcaag tgtatcatat gccaagtccg ccccctattg acgtcaatga    420

cggtaaatgg cccgcctggc attatgccca gtacatgacc ttacgggact ttcctacttg    480

gcagtacatc tacgtattag tcatcgctat taccatggtg atgcggtttt ggcagtacac    540

caatgggcgt ggatagcggt ttgactcacg gggatttcca agtctccacc ccattgacgt    600

caatgggagt ttgttttggc accaaaatca acgggacttt ccaaaatgtc gtaacaactg    660

cgatcgcccg ccccgttgac gcaaatgggc ggtaggcgtg tacggtggga ggtctatata    720

agcagagctc gtttagtgaa ccgtcagatc actagaagct ttattgcggt agtttatcac    780

agttaaattg ctaacgcagt cagtgcttct gacacaacag tctcgaactt aagctgcagt    840

gactctctta aggtagcctt gcagaagttg gtcgtgaggc actgggcagg taagtatcaa    900

ggttacaaga caggtttaag gagaccaata gaaactgggc ttgtcgagac agagaagact    960

cttgcgtttc tgataggcac ctattggtct tactgacatc cactttgcct ttctctccac   1020

aggtgtccac tcccagttca attacagctc ttaaggctag agtacttaat acgactcact   1080

ataggctagc cagcttgaag caagcctcct gaaagatgaa gctactgtct tctatcgaac   1140

aagcatgcga tatttgccga cttaaaaagc tcaagtgctc caaagaaaaa ccgaagtgcg   1200

ccaagtgtct gaagaacaac tgggagtgtc gctactctcc caaaaccaaa aggtctccgc   1260

tgactagggc acatctgaca gaagtggaat caaggctaga aagactggaa cagctatttc   1320

tactgatttt tcctcgagaa gaccttgaca tgattttgaa aatggattct ttacaggata   1380

taaaagcatt gttaacagga ttatttgtac aagataatgt gaataaagat gccgtcacag   1440
```

-continued

```
atagattggc ttcagtggag actgatatgc ctctaacatt gagacagcat agaataagtg   1500
cgacatcatc atcggaagag agtagtaaca aaggtcaaag acagttgact gtatcgccgg   1560
aattcccggg gatccgttct tctgtcaggg gagtgagtat ttctaaattt gaagaaagat   1620
gctgctttct ttatgtgctt cacaattctg atgatttcca aatctatttc tgtacagaac   1680
ttcattgtaa aaagtttttt gagatggtga acaccattac cgaagagaag gggagaagca   1740
cagaggaagg agactgtgaa agtgacttgc tggagtatga ctatgaatat gatgaaaatg   1800
gtgacagagt cgttttagga aaaggcactt atgggatagt ctacgcaggt cgggacttga   1860
gcaaccaagt cagaattgct attaaggaaa tcccagagag agacagcaga tactctcagc   1920
ccctgcatga agaaatagca ttgcataaac acctgaagca caaaaatatt gtccagtatc   1980
tgggctcttt cagtgagaat ggtttcatta aaatcttcat ggagcaggtc cctggaggaa   2040
gtctttctgc tctccttcgt tccaaatggg gtccattaaa agacaatgag caaacaattg   2100
gcttttatac aaagcaaata ctggaaggat taaaatatct ccatgacaat cagatagttc   2160
accgggacat aaagggtgac aatgtgttga ttaataccta cagtggtgtt ctcaagatct   2220
ctgacttcgg aacatcaaag aggcttgctg gcataaaccc ctgtactgaa acttttactg   2280
gtaccctcca gtatatggca ccagaaataa tagataaagg accaagaggc tacggaaaag   2340
cagcagacat ctggtctctg ggctgtacaa tcattgaaat ggccacagga aaacccccat   2400
tttatgaact gggagaacca caagcagcta tgttcaaggt gggaatgttt aaagtccacc   2460
ctgagatccc atctagatct agagcggccg caggtacctg aataactaag gccgcttccc   2520
tttagtgagg gttaatgctt cgagcagaca tgataagata cattgatgag tttggacaaa   2580
ccacaactag aatgcagtga aaaaaatgct ttatttgtga aatttgtgat gctattgctt   2640
tatttgtaac cattataagc tgcaataaac aagttaacaa caacaattgc attcatttta   2700
tgtttcaggt tcagggggag atgtgggagg ttttttaaag caagtaaaac ctctacaaat   2760
gtggtaaaat ccgataagga tcgatccggg ctggcgtaat agcgaagagg cccgcaccga   2820
tcgcccttcc caacagttgc gcagcctgaa tggcgaatgg acgcgccctg tagcggcgca   2880
ttaagcgcgg cgggtgtggt ggttacgcgc agcgtgaccg ctacacttgc cagcgcccta   2940
gcgcccgctc ctttcgcttt cttcccttcc tttcacgcca cgttcgccgg ctttccccgt   3000
caagctctaa atcgggggct ccctttaggg ttccgattta gtgctttacg gcacctcgac   3060
cccaaaaaac ttgattaggg tgatggttca cgtagtgggc catcgccctg atagacggtt   3120
tttcgccctt tgacgttgga gtccacgttc tttaatagtg gactcttgtt ccaaactgga   3180
acaacactca accctatctc ggtctattct tttgatttat aagggatttt gccgatttcg   3240
gcctattggt taaaaaatga gctgatttaa caaaaattta acgcgaattt taacaaaata   3300
ttaacgctta caatttcctg atgcggtatt ttctccttac gcatctgtgc ggtatttcac   3360
accgcatacg cggatcttcc gtaccttctg aggcggaaag aaccagctgt ggaatgtgtg   3420
tcagttaggg tgtggaaagt ccccaggctc cccagcaggc agaagtatgc aaagcatgca   3480
tctcaattag tcagcaacca ggtgtggaaa gtccccaggc tccccagcag gcagaagtat   3540
gcaaagcatg catctcaatt agtcagcaac catagtcccg cccctaactc cgcccatccc   3600
gcccctaact ccgcccagtt ccgcccattc tccgccccat ggctgactaa ttttttttat   3660
ttatgcagag gccgaggccg cctcggcctc tgagctattc cagaagtagt gaggaggctt   3720
ttttggaggc ctaggctttt gcaaaaagct tgattcttct gacacaacag tctcgaactt   3780
```

-continued

```
aaggctagaa ttctggctac aggtaagcgc ccctaaaatc cctttgggca caatgtgtcc   3840
tgaggggaga ggcagcgacc tgtagatggg acgggggcac taaccctcag gtttggggct   3900
tctgaatgtg agtatcgcca tgtaagccca gtatttggcc aatctcagaa agctcctggt   3960
ccctggaggg atggagagag aaaaacaaac agctcctgga gcagggagag tgctggcctc   4020
ttgctctccg gctccctctg ttgccctctg gtttctcccc aggctcccgg acgtcctcta   4080
gccaccatga cttcgaaagt ttatgatcca gaacaaagga aacggatgat aactggtccg   4140
cagtggtggg ccagatgtaa acaaatgaat gttcttgatt catttattaa ttattatgat   4200
tcagaaaaac atgcagaaaa tgctgttatt tttttacatg gtaacgcggc ctcttcttat   4260
ttatggcgac atgttgtgcc acatattgag ccagtagcgc ggtgtattat accagacctt   4320
attggtatgg gcaaatcagg caaatctggt aatggttctt ataggttact tgatcattac   4380
aaatatctta ctgcatggtt tgaacttctt aatttaccaa agaagatcat tttgtcggc    4440
catgattggg gtgcttgttt ggcatttcat tatagctatg agcatcaaga taagatcaaa   4500
gcaatagttc acgctgaaag tgtagtagat gtgattgaat catgggatga atggcctgat   4560
attgaagaag atattgcgtt gatcaaatct gaagaaggag aaaaaatggt tttggagaat   4620
aacttcttcg tggaaaccat gttgccatca aaaatcatga gaaagttaga accagaagaa   4680
tttgcagcat atcttgaacc attcaaagag aaaggtgaag ttcgtcgtcc aacattatca   4740
tggcctcgtg aaatcccgtt agtaaaaggt ggtaaacctg acgttgtaca aattgttagg   4800
aattataatg cttatctacg tgcaagtgat gatttaccaa aaatgtttat tgaatcggac   4860
ccaggattct tttccaatgc tattgttgaa ggtgccaaga agtttcctaa tactgaattt   4920
gtcaaagtaa aaggtcttca tttttcgcaa gaagatgcac ctgatgaaat gggaaaatat   4980
atcaaatcgt tcgttgagcg agttctcaaa aatgaacaat aattctagcc ctgaataagt   5040
gataataagc ggatgaatgg cagaaattcg tcgaagcgca ataaaatatc tttattttca   5100
ttacatctgt gtgttggttt tttgtgtgaa tcgatagcga taaggatcgg aagatccgcg   5160
tatggtgcac tctcagtaca atctgctctg atgccgcata gttaagccag ccccgacacc   5220
cgccaacacc cgctgacgcg ccctgacggg cttgtctgct cccggcatcc gcttacagac   5280
aagctgtgac cgtctccggg agctgcatgt gtcagaggtt ttcaccgtca tcaccgaaac   5340
gcgcgagacg aaagggcctc gtgatacgcc tatttttata ggttaatgtc atgataataa   5400
tggtttctta gacgtcaggt ggcacttttc ggggaaatgt gcgcggaacc cctatttgtt   5460
tatttttcta aatacattca aatatgtatc cgctcatgag acaataaccc tgataaatgc   5520
ttcaataata ttgaaaaagg aagagtatga gtattcaaca tttccgtgtc gcccttattc   5580
ccttttttgc ggcattttgc cttcctgttt ttgctcaccc agaaacgctg gtgaaagtaa   5640
aagatgctga agatcagttg ggtgcacgag tgggttacat cgaactggat ctcaacagcg   5700
gtaagatcct tgagagtttt cgccccgaag aacgttttcc aatgatgagc acttttaaag   5760
ttctgctatg tggcgcggta ttatcccgtg ttgacgccgg gcaagagcaa ctcggtcgcc   5820
gcatacacta ttctcagaat gacttggttg agtactcacc agtcacagaa aagcatctta   5880
cggatggcat gacagtaaga gaattatgca gtgctgccat aaccatgagt gataacactg   5940
cggccaactt acttctgaca acgatcggag gaccgaagga gctaaccgct tttttgcaca   6000
acatggggga tcatgtaact cgccttgatc gttgggaacc ggagctgaat gaagccatac   6060
caaacgacga gcgtgacacc acgatgcctg tagcaatggc aacaacgttg cgcaaactat   6120
taactggcga actacttact ctagcttccc ggcaacaatt aatagactgg atggaggcgg   6180
```

ataaagttgc aggaccactt ctgcgctcgg cccttccggc tggctggttt attgctgata 6240
aatctggagc cggtgagcgt gggtctcgcg gtatcattgc agcactgggg ccagatggta 6300
agccctcccg tatcgtagtt atctacacga cggggagtca ggcaactatg gatgaacgaa 6360
atagacagat cgctgagata ggtgcctcac tgattaagca ttggtaactg tcagaccaag 6420
tttactcata tatactttag attgatttaa aacttcattt ttaatttaaa aggatctagg 6480
tgaagatcct ttttgataat ctcatgacca aaatccctta acgtgagttt tcgttccact 6540
gagcgtcaga ccccgtagaa aagatcaaag gatcttcttg agatcctttt tttctgcgcg 6600
taatctgctg cttgcaaaca aaaaaaccac cgctaccagc ggtggtttgt ttgccggatc 6660
aagagctacc aactcttttt ccgaaggtaa ctggcttcag cagagcgcag ataccaaata 6720
ctgttcttct agtgtagccg tagttaggcc accacttcaa gaactctgta gcaccgccta 6780
catacctcgc tctgctaatc ctgttaccag tggctgctgc cagtggcgat aagtcgtgtc 6840
ttaccgggtt ggactcaaga cgatagttac cggataaggc gcagcggtcg ggctgaacgg 6900
ggggttcgtg cacacagccc agcttggagc gaacgaccta caccgaactg agatacctac 6960
agcgtgagct atgagaaagc gccacgcttc ccgaagggag aaaggcggac aggtatccgg 7020
taagcggcag ggtcggaaca ggagagcgca cgagggagct tccaggggga aacgcctggt 7080
atctttatag tcctgtcggg tttcgccacc tctgacttga gcgtcgattt ttgtgatgct 7140
cgtcaggggg gcggagccta tggaaaaacg ccagcaacgc ggccttttta cggttcctgg 7200
ccttttgctg gccttttgct cacatggctc gacagatct 7239

<210> SEQ ID NO 9
<211> LENGTH: 454
<212> TYPE: PRT
<213> ORGANISM: Artificial Sequence
<220> FEATURE:
<223> OTHER INFORMATION: Gal4 ASK1(c) fusion protein sequence

<400> SEQUENCE: 9

Met Lys Leu Leu Ser Ser Ile Glu Gln Ala Cys Asp Ile Cys Arg Leu
1 5 10 15

Lys Lys Leu Lys Cys Ser Lys Glu Lys Pro Lys Cys Ala Lys Cys Leu
20 25 30

Lys Asn Asn Trp Glu Cys Arg Tyr Ser Pro Lys Thr Lys Arg Ser Pro
35 40 45

Leu Thr Arg Ala His Leu Thr Glu Val Glu Ser Arg Leu Glu Arg Leu
50 55 60

Glu Gln Leu Phe Leu Leu Ile Phe Pro Arg Glu Asp Leu Asp Met Ile
65 70 75 80

Leu Lys Met Asp Ser Leu Gln Asp Ile Lys Ala Leu Leu Thr Gly Leu
85 90 95

Phe Val Gln Asp Asn Val Asn Lys Asp Ala Val Thr Asp Arg Leu Ala
100 105 110

Ser Val Glu Thr Asp Met Pro Leu Thr Leu Arg Gln His Arg Ile Ser
115 120 125

Ala Thr Ser Ser Ser Glu Glu Ser Ser Asn Lys Gly Gln Arg Gln Leu
130 135 140

Thr Val Ser Pro Glu Phe Pro Gly Ile Arg Ser Ser Val Arg Gly Val
145 150 155 160

Ser Ile Ser Lys Phe Glu Glu Arg Cys Cys Phe Leu Tyr Val Leu His
165 170 175

```
Asn Ser Asp Asp Phe Gln Ile Tyr Phe Cys Thr Glu Leu His Cys Lys
            180                 185                 190

Lys Phe Phe Glu Met Val Asn Thr Ile Thr Glu Glu Lys Gly Arg Ser
        195                 200                 205

Thr Glu Glu Gly Asp Cys Glu Ser Asp Leu Leu Glu Tyr Asp Tyr Glu
    210                 215                 220

Tyr Asp Glu Asn Gly Asp Arg Val Val Leu Gly Lys Gly Thr Tyr Gly
225                 230                 235                 240

Ile Val Tyr Ala Gly Arg Asp Leu Ser Asn Gln Val Arg Ile Ala Ile
                245                 250                 255

Lys Glu Ile Pro Glu Arg Asp Ser Arg Tyr Ser Gln Pro Leu His Glu
            260                 265                 270

Glu Ile Ala Leu His Lys His Leu Lys His Lys Asn Ile Val Gln Tyr
        275                 280                 285

Leu Gly Ser Phe Ser Glu Asn Gly Phe Ile Lys Ile Phe Met Glu Gln
    290                 295                 300

Val Pro Gly Gly Ser Leu Ser Ala Leu Leu Arg Ser Lys Trp Gly Pro
305                 310                 315                 320

Leu Lys Asp Asn Glu Gln Thr Ile Gly Phe Tyr Thr Lys Gln Ile Leu
                325                 330                 335

Glu Gly Leu Lys Tyr Leu His Asp Asn Gln Ile Val His Arg Asp Ile
            340                 345                 350

Lys Gly Asp Asn Val Leu Ile Asn Thr Tyr Ser Gly Val Leu Lys Ile
        355                 360                 365

Ser Asp Phe Gly Thr Ser Lys Arg Leu Ala Gly Ile Asn Pro Cys Thr
    370                 375                 380

Glu Thr Phe Thr Gly Thr Leu Gln Tyr Met Ala Pro Glu Ile Ile Asp
385                 390                 395                 400

Lys Gly Pro Arg Gly Tyr Gly Lys Ala Ala Asp Ile Trp Ser Leu Gly
                405                 410                 415

Cys Thr Ile Ile Glu Met Ala Thr Gly Lys Pro Pro Phe Tyr Glu Leu
            420                 425                 430

Gly Glu Pro Gln Ala Ala Met Phe Lys Val Gly Met Phe Lys Val His
        435                 440                 445

Pro Glu Ile Pro Ser Arg
    450


<210> SEQ ID NO 10
<211> LENGTH: 6918
<212> TYPE: DNA
<213> ORGANISM: Artificial Sequence
<220> FEATURE:
<223> OTHER INFORMATION: construct sequence containing ASK1(d) cloned in
      pBIND

<400> SEQUENCE: 10

tcaatattgg ccattagcca tattattcat tggttatata gcataaatca atattggcta      60

ttggccattg catacgttgt atctatatca taatatgtac atttatattg gctcatgtcc     120

aatatgaccg ccatgttggc attgattatt gactagttat taatagtaat caattacggg     180

gtcattagtt catagcccat atatggagtt ccgcgttaca taacttacgg taaatggccc     240

gcctggctga ccgcccaacg acccccgccc attgacgtca ataatgacgt atgttcccat     300

agtaacgcca atagggactt tccattgacg tcaatgggtg gagtatttac ggtaaactgc     360

ccacttggca gtacatcaag tgtatcatat gccaagtccg ccccctattg acgtcaatga     420
```

-continued

```
cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt ttgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaggctag agtacttaat acgactcact   1080
ataggctagc cagcttgaag caagcctcct gaaagatgaa gctactgtct tctatcgaac   1140
aagcatgcga tatttgccga cttaaaaagc tcaagtgctc caaagaaaaa ccgaagtgcg   1200
ccaagtgtct gaagaacaac tgggagtgtc gctactctcc caaaaccaaa aggtctccgc   1260
tgactagggc acatctgaca gaagtggaat caaggctaga aagactggaa cagctatttc   1320
tactgatttt tcctcgagaa gaccttgaca tgattttgaa aatggattct ttacaggata   1380
taaaagcatt gttaacagga ttatttgtac aagataatgt gaataaagat gccgtcacag   1440
atagattggc ttcagtggag actgatatgc ctctaacatt gagacagcat agaataagtg   1500
cgacatcatc atcggaagag agtagtaaca aaggtcaaag acagttgact gtatcgccgg   1560
aattcccggg gatccgtgca gcagacatct ggtctctggg ctgtacaatc attgaaatgg   1620
ccacaggaaa acccccattt tatgaactgg gagaaccaca agcagctatg ttcaaggtgg   1680
gaatgtttaa agtccaccct gagatcccag agtccatgtc tgcagaggcc aaggcattca   1740
tactgaaatg ttttgaacca gatcctgaca agagagcctg tgctaacgac ttgcttgttg   1800
atgagttttt aaaagtttca agcaaaaaga aaaagacaca acctaagctt tcagctcttt   1860
cagctggatc aaatgaatat ctcaggagta tatccttgcc ggtacctgtg ctggtggagg   1920
acaccagcag cagcagtgag tacggctcag tttcacccga cacggagttg aaagtggacc   1980
ccttctcttt caaaacaaga gccaagtcct gcggagaaag agatgtcaag ggaattcgga   2040
cactcttttt gggcattcca gatgagaatt ttgaagatca cagtgctcct ccttcccctg   2100
aagaaaaaga ttctggattc ttcatgctga ggaaggacag tgagaggcga tctagatcta   2160
gagcggccgc aggtacctga ataactaagg ccgcttccct ttagtgaggg ttaatgcttc   2220
gagcagacat gataagatac attgatgagt ttggacaaac cacaactaga atgcagtgaa   2280
aaaaatgctt tatttgtgaa atttgtgatg ctattgcttt atttgtaacc attataagct   2340
gcaataaaca agttaacaac aacaattgca ttcattttat gtttcaggtt cagggggaga   2400
tgtgggaggt tttttaaagc aagtaaaacc tctacaaatg tggtaaaatc cgataaggat   2460
cgatccgggc tggcgtaata gcgaagaggc ccgcaccgat cgcccttccc aacagttgcg   2520
cagcctgaat ggcgaatgga cgcgccctgt agcggcgcat taagcgcggc gggtgtggtg   2580
gttacgcgca gcgtgaccgc tacacttgcc agcgccctag cgcccgctcc tttcgctttc   2640
ttcccttcct ttcacgccac gttcgccggc tttccccgtc aagctctaaa tcgggggctc   2700
cctttagggt tccgatttag tgctttacgg cacctcgacc ccaaaaaact tgattagggt   2760
```

-continued

```
gatggttcac gtagtgggcc atcgccctga tagacggttt ttcgcccttt gacgttggag   2820
tccacgttct ttaatagtgg actcttgttc caaactggaa caacactcaa ccctatctcg   2880
gtctattctt ttgatttata agggattttg ccgatttcgg cctattggtt aaaaaatgag   2940
ctgatttaac aaaaatttaa cgcgaatttt aacaaaatat taacgcttac aatttcctga   3000
tgcggtattt tctccttacg catctgtgcg gtatttcaca ccgcatacgc ggatcttccg   3060
taccttctga ggcggaaaga accagctgtg gaatgtgtgt cagttagggt gtggaaagtc   3120
cccaggctcc ccagcaggca gaagtatgca aagcatgcat ctcaattagt cagcaaccag   3180
gtgtggaaag tccccaggct ccccagcagg cagaagtatg caaagcatgc atctcaatta   3240
gtcagcaacc atagtcccgc ccctaactcc gcccatcccg cccctaactc cgcccagttc   3300
cgcccattct ccgccccatg gctgactaat tttttttatt tatgcagagg ccgaggccgc   3360
ctcggcctct gagctattcc agaagtagtg aggaggcttt tttggaggcc taggcttttg   3420
caaaaagctt gattcttctg acacaacagt ctcgaactta aggctagaat tctggctaca   3480
ggtaagcgcc cctaaaatcc ctttgggcac aatgtgtcct gaggggagag gcagcgacct   3540
gtagatggga cgggggcact aaccctcagg tttggggctt ctgaatgtga gtatcgccat   3600
gtaagcccag tatttggcca atctcagaaa gctcctggtc cctggaggga tggagagaga   3660
aaaacaaaca gctcctggag cagggagagt gctggcctct tgctctccgg ctccctctgt   3720
tgccctctgg tttctcccca ggctcccgga cgtcctctag ccaccatgac ttcgaaagtt   3780
tatgatccag aacaaaggaa acggatgata actggtccgc agtggtgggc cagatgtaaa   3840
caaatgaatg ttcttgattc atttattaat tattatgatt cagaaaaaca tgcagaaaat   3900
gctgttattt ttttacatgg taacgcggcc tcttcttatt tatggcgaca tgttgtgcca   3960
catattgagc cagtagcgcg gtgtattata ccagacctta ttggtatggg caaatcaggc   4020
aaatctggta atggttctta taggttactt gatcattaca aatatcttac tgcatggttt   4080
gaacttctta atttaccaaa gaagatcatt tttgtcggcc atgattgggg tgcttgtttg   4140
gcatttcatt atagctatga gcatcaagat aagatcaaag caatagttca cgctgaaagt   4200
gtagtagatg tgattgaatc atgggatgaa tggcctgata ttgaagaaga tattgcgttg   4260
atcaaatctg aagaaggaga aaaaatggtt ttggagaata acttcttcgt ggaaaccatg   4320
ttgccatcaa aaatcatgag aaagttagaa ccagaagaat ttgcagcata tcttgaacca   4380
ttcaaagaga aaggtgaagt tcgtcgtcca acattatcat ggcctcgtga aatcccgtta   4440
gtaaaaggtg gtaaacctga cgttgtacaa attgttagga attataatgc ttatctacgt   4500
gcaagtgatg atttaccaaa aatgtttatt gaatcggacc caggattctt ttccaatgct   4560
attgttgaag gtgccaagaa gtttcctaat actgaatttg tcaaagtaaa aggtcttcat   4620
ttttcgcaag aagatgcacc tgatgaaatg ggaaaatata tcaaatcgtt cgttgagcga   4680
gttctcaaaa atgaacaata attctagccc tgaataagtg ataataagcg gatgaatggc   4740
agaaattcgt cgaagcgcaa taaaatatct ttattttcat tacatctgtg tgttggtttt   4800
ttgtgtgaat cgatagcgat aaggatcgga agatccgcgt atggtgcact ctcagtacaa   4860
tctgctctga tgccgcatag ttaagccagc cccgacaccc gccaacaccc gctgacgcgc   4920
cctgacgggc ttgtctgctc ccggcatccg cttacagaca agctgtgacc gtctccggga   4980
gctgcatgtg tcagaggttt tcaccgtcat caccgaaacg cgcgagacga aagggcctcg   5040
tgatacgcct atttttatag gttaatgtca tgataataat ggtttcttag acgtcaggtg   5100
gcacttttcg gggaaatgtg cgcggaaccc ctatttgttt atttttctaa atacattcaa   5160
```

```
atatgtatcc gctcatgaga caataaccct gataaatgct tcaataatat tgaaaaagga   5220
agagtatgag tattcaacat ttccgtgtcg cccttattcc cttttttgcg gcattttgcc   5280
ttcctgtttt tgctcaccca gaaacgctgg tgaaagtaaa agatgctgaa gatcagttgg   5340
gtgcacgagt gggttacatc gaactggatc tcaacagcgg taagatcctt gagagttttc   5400
gccccgaaga acgttttcca atgatgagca cttttaaagt tctgctatgt ggcgcggtat   5460
tatcccgtgt tgacgccggg caagagcaac tcggtcgccg catacactat tctcagaatg   5520
acttggttga gtactcacca gtcacagaaa agcatcttac ggatggcatg acagtaagag   5580
aattatgcag tgctgccata accatgagtg ataacactgc ggccaactta cttctgacaa   5640
cgatcggagg accgaaggag ctaaccgctt ttttgcacaa catgggggat catgtaactc   5700
gccttgatcg ttgggaaccg gagctgaatg aagccatacc aaacgacgag cgtgacacca   5760
cgatgcctgt agcaatggca acaacgttgc gcaaactatt aactggcgaa ctacttactc   5820
tagcttcccg gcaacaatta atagactgga tggaggcgga taaagttgca ggaccacttc   5880
tgcgctcggc ccttccggct ggctggttta ttgctgataa atctggagcc ggtgagcgtg   5940
ggtctcgcgg tatcattgca gcactggggc cagatggtaa gccctcccgt atcgtagtta   6000
tctacacgac ggggagtcag gcaactatgg atgaacgaaa tagacagatc gctgagatag   6060
gtgcctcact gattaagcat tggtaactgt cagaccaagt ttactcatat atactttaga   6120
ttgatttaaa acttcatttt taatttaaaa ggatctaggt gaagatcctt tttgataatc   6180
tcatgaccaa aatcccttaa cgtgagtttt cgttccactg agcgtcagac cccgtagaaa   6240
agatcaaagg atcttcttga gatccttttt ttctgcgcgt aatctgctgc ttgcaaacaa   6300
aaaaaccacc gctaccagcg gtggtttgtt tgccggatca agagctacca actctttttc   6360
cgaaggtaac tggcttcagc agagcgcaga taccaaatac tgttcttcta gtgtagccgt   6420
agttaggcca ccacttcaag aactctgtag caccgcctac atacctcgct ctgctaatcc   6480
tgttaccagt ggctgctgcc agtggcgata agtcgtgtct taccgggttg gactcaagac   6540
gatagttacc ggataaggcg cagcggtcgg gctgaacggg gggttcgtgc acacagccca   6600
gcttggagcg aacgacctac accgaactga gatacctaca gcgtgagcta tgagaaagcg   6660
ccacgcttcc cgaagggaga aaggcggaca ggtatccggt aagcggcagg gtcggaacag   6720
gagagcgcac gagggagctt ccagggggaa acgcctggta tctttatagt cctgtcgggt   6780
ttcgccacct ctgacttgag cgtcgatttt tgtgatgctc gtcagggggg cggagcctat   6840
ggaaaaacgc cagcaacgcg gcctttttac ggttcctggc cttttgctgg ccttttgctc   6900
acatggctcg acagatct                                                 6918
```

<210> SEQ ID NO 11
<211> LENGTH: 347
<212> TYPE: PRT
<213> ORGANISM: Artificial Sequence
<220> FEATURE:
<223> OTHER INFORMATION: Gal4 ASK1(d) fusion protein sequence

<400> SEQUENCE: 11

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45
```

Leu Thr Arg Ala His Leu Thr Glu Val Glu Ser Arg Leu Glu Arg Leu
50 55 60

Glu Gln Leu Phe Leu Leu Ile Phe Pro Arg Glu Asp Leu Asp Met Ile
65 70 75 80

Leu Lys Met Asp Ser Leu Gln Asp Ile Lys Ala Leu Leu Thr Gly Leu
85 90 95

Phe Val Gln Asp Asn Val Asn Lys Asp Ala Val Thr Asp Arg Leu Ala
100 105 110

Ser Val Glu Thr Asp Met Pro Leu Thr Leu Arg Gln His Arg Ile Ser
115 120 125

Ala Thr Ser Ser Ser Glu Glu Ser Ser Asn Lys Gly Gln Arg Gln Leu
130 135 140

Thr Val Ser Pro Glu Phe Pro Gly Ile Arg Ala Ala Asp Ile Trp Ser
145 150 155 160

Leu Gly Cys Thr Ile Ile Glu Met Ala Thr Gly Lys Pro Pro Phe Tyr
165 170 175

Glu Leu Gly Glu Pro Gln Ala Ala Met Phe Lys Val Gly Met Phe Lys
180 185 190

Val His Pro Glu Ile Pro Glu Ser Met Ser Ala Glu Ala Lys Ala Phe
195 200 205

Ile Leu Lys Cys Phe Glu Pro Asp Pro Asp Lys Arg Ala Cys Ala Asn
210 215 220

Asp Leu Leu Val Asp Glu Phe Leu Lys Val Ser Ser Lys Lys Lys Lys
225 230 235 240

Thr Gln Pro Lys Leu Ser Ala Leu Ser Ala Gly Ser Asn Glu Tyr Leu
245 250 255

Arg Ser Ile Ser Leu Pro Val Pro Val Leu Val Glu Asp Thr Ser Ser
260 265 270

Ser Ser Glu Tyr Gly Ser Val Ser Pro Asp Thr Glu Leu Lys Val Asp
275 280 285

Pro Phe Ser Phe Lys Thr Arg Ala Lys Ser Cys Gly Glu Arg Asp Val
290 295 300

Lys Gly Ile Arg Thr Leu Phe Leu Gly Ile Pro Asp Glu Asn Phe Glu
305 310 315 320

Asp His Ser Ala Pro Pro Ser Pro Glu Glu Lys Asp Ser Gly Phe Phe
325 330 335

Met Leu Arg Lys Asp Ser Glu Arg Arg Ser Arg
340 345

<210> SEQ ID NO 12
<211> LENGTH: 7171
<212> TYPE: DNA
<213> ORGANISM: Artificial Sequence
<220> FEATURE:
<223> OTHER INFORMATION: construct sequence containing ASK1(e) cloned in pBIND

<400> SEQUENCE: 12
tcaatattgg ccattagcca tattattcat tggttatata gcataaatca atattggcta 60
ttggccattg catacgttgt atctatatca taatatgtac atttatattg gctcatgtcc 120
aatatgaccg ccatgttggc attgattatt gactagttat taatagtaat caattacggg 180
gtcattagtt catagcccat atatggagtt ccgcgttaca taacttacgg taaatggccc 240
gcctggctga ccgcccaacg acccccgccc attgacgtca ataatgacgt atgttcccat 300

-continued

```
agtaacgcca atagggactt tccattgacg tcaatgggtg gagtatttac ggtaaactgc    360
ccacttggca gtacatcaag tgtatcatat gccaagtccg cccctattg acgtcaatga    420
cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt ttgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaggctag agtacttaat acgactcact   1080
ataggctagc cagcttgaag caagcctcct gaaagatgaa gctactgtct tctatcgaac   1140
aagcatgcga tatttgccga cttaaaaagc tcaagtgctc caaagaaaaa ccgaagtgcg   1200
ccaagtgtct gaagaacaac tgggagtgtc gctactctcc caaaaccaaa aggtctccgc   1260
tgactagggc acatctgaca gaagtggaat caaggctaga aagactggaa cagctatttc   1320
tactgatttt tcctcgagaa gaccttgaca tgattttgaa aatggattct ttacaggata   1380
taaaagcatt gttaacagga ttatttgtac aagataatgt gaataaagat gccgtcacag   1440
atagattggc ttcagtggag actgatatgc ctctaacatt gagacagcat agaataagtg   1500
cgacatcatc atcggaagag agtagtaaca aaggtcaaag acagttgact gtatcgccgg   1560
aattcccggg gatccatgaa gctactgtct tctatcgaac aagcatgcga tatttgccga   1620
cttaaaaagc tcaagtgctc caaagaaaaa ccgaagtgcg ccaagtgtct gaagaacaac   1680
tgggagtgtc gctactctcc caaaaccaaa aggtctccgc tgactagggc acatctgaca   1740
gaagtggaat caaggctaga aagactggaa cagctatttc tactgatttt tcctcgagaa   1800
gaccttgaca tgattttgaa aatggattct ttacaggata taaaagcatt gttaacagga   1860
ttatttgtac aagataatgt gaataaagat gccgtcacag atagattggc ttcagtggag   1920
actgatatgc ctctaacatt gagacagcat agaataagtg cgacatcatc atcggaagag   1980
agtagtaaca aaggtcaaag acagttgact gtatcgccgg aattcccggg gatcctgacg   2040
gaagaccaag acaaaattgt gagaaaccta atggaatctt tagctcaggg ggctgaagaa   2100
ccgaaactaa aatgggaaca catcacaacc ctcattgcaa gcctcagaga atttgtgaga   2160
tccactgacc gaaaaatcat agccaccaca ctgtcaaagc tgaaactgga gctggacttc   2220
gacagccatg gcattagcca agtccaggtg gtactctttg gttttcaaga tgctgtcaat   2280
aaagttcttc ggaatcataa catcaagccg cactggatgt ttgccttaga cagtatcatt   2340
cggaaggcgg tacagacagc cattaccatc ctggttccag aactaaggcc acatttcagc   2400
cttgcatctt ctagagcggc cgcaggtacc tgaataacta aggccgcttc cctttagtga   2460
gggttaatgc ttcgagcaga catgataaga tacattgatg agtttggaca aaccacaact   2520
agaatgcagt gaaaaaaatg ctttatttgt gaaatttgtg atgctattgc tttatttgta   2580
accattataa gctgcaataa acaagttaac aacaacaatt gcattcattt tatgtttcag   2640
gttcaggggg agatgtggga ggttttttaa agcaagtaaa acctctacaa atgtggtaaa   2700
```

-continued

```
atccgataag gatcgatccg ggctggcgta atagcgaaga ggcccgcacc gatcgccctt   2760
cccaacagtt gcgcagcctg aatggcgaat ggacgcgccc tgtagcggcg cattaagcgc   2820
ggcgggtgtg gtggttacgc gcagcgtgac cgctacactt gccagcgccc tagcgcccgc   2880
tcctttcgct ttcttccctt cctttcacgc cacgttcgcc ggctttcccc gtcaagctct   2940
aaatcggggg ctccctttag ggttccgatt tagtgcttta cggcacctcg accccaaaaa   3000
acttgattag ggtgatggtt cacgtagtgg gccatcgccc tgatagacgg tttttcgccc   3060
tttgacgttg gagtccacgt tctttaatag tggactcttg ttccaaactg gaacaacact   3120
caaccctatc tcggtctatt cttttgattt ataagggatt ttgccgattt cggcctattg   3180
gttaaaaaat gagctgattt aacaaaaatt taacgcgaat tttaacaaaa tattaacgct   3240
tacaatttcc tgatgcggta ttttctcctt acgcatctgt gcggtatttc acaccgcata   3300
cgcggatctt ccgtaccttc tgaggcggaa agaaccagct gtggaatgtg tgtcagttag   3360
ggtgtggaaa gtccccaggc tccccagcag gcagaagtat gcaaagcatg catctcaatt   3420
agtcagcaac caggtgtgga aagtccccag gctccccagc aggcagaagt atgcaaagca   3480
tgcatctcaa ttagtcagca accatagtcc cgcccctaac tccgcccatc ccgcccctaa   3540
ctccgcccag ttccgcccat tctccgcccc atggctgact aattttttt atttatgcag   3600
aggccgaggc cgcctcggcc tctgagctat tccagaagta gtgaggaggc ttttttggag   3660
gcctaggctt ttgcaaaaag cttgattctt ctgacacaac agtctcgaac ttaaggctag   3720
aattctggct acaggtaagc gcccctaaaa tccctttggg cacaatgtgt cctgagggga   3780
gaggcagcga cctgtagatg ggacgggggc actaaccctc aggtttgggg cttctgaatg   3840
tgagtatcgc catgtaagcc cagtatttgg ccaatctcag aaagctcctg gtccctggag   3900
ggatggagag agaaaaacaa acagctcctg gagcagggag agtgctggcc tcttgctctc   3960
cggctccctc tgttgccctc tggtttctcc ccaggctccc ggacgtcctc tagccaccat   4020
gacttcgaaa gtttatgatc cagaacaaag gaaacggatg ataactggtc cgcagtggtg   4080
ggccagatgt aaacaaatga atgttcttga ttcatttatt aattattatg attcagaaaa   4140
acatgcagaa aatgctgtta tttttttaca tggtaacgcg gcctcttctt atttatggcg   4200
acatgttgtg ccacatattg agccagtagc gcggtgtatt ataccagacc ttattggtat   4260
gggcaaatca ggcaaatctg gtaatggttc ttataggtta cttgatcatt acaaatatct   4320
tactgcatgg tttgaacttc ttaatttacc aaagaagatc atttttgtcg gccatgattg   4380
gggtgcttgt ttggcatttc attatagcta tgagcatcaa gataagatca aagcaatagt   4440
tcacgctgaa agtgtagtag atgtgattga atcatgggat gaatggcctg atattgaaga   4500
agatattgcg ttgatcaaat ctgaagaagg agaaaaaatg gttttggaga ataacttctt   4560
cgtggaaacc atgttgccat caaaaatcat gagaaagtta gaaccagaag aatttgcagc   4620
atatcttgaa ccattcaaag agaaaggtga agttcgtcgt ccaacattat catggcctcg   4680
tgaaatcccg ttagtaaaag gtggtaaacc tgacgttgta caaattgtta ggaattataa   4740
tgcttatcta cgtgcaagtg atgatttacc aaaaatgttt attgaatcgg acccaggatt   4800
cttttccaat gctattgttg aaggtgccaa gaagtttcct aatactgaat ttgtcaaagt   4860
aaaaggtctt catttttcgc aagaagatgc acctgatgaa atgggaaaat atatcaaatc   4920
gttcgttgag cgagttctca aaaatgaaca ataattctag ccctgaataa gtgataataa   4980
gcggatgaat ggcagaaatt cgtcgaagcg caataaaata tctttatttt cattacatct   5040
```

-continued gtgtgttggt tttttgtgtg aatcgatagc gataaggatc ggaagatccg cgtatggtgc 5100
actctcagta caatctgctc tgatgccgca tagttaagcc agccccgaca cccgccaaca 5160
cccgctgacg cgccctgacg ggcttgtctg ctcccggcat ccgcttacag acaagctgtg 5220
accgtctccg ggagctgcat gtgtcagagg ttttcaccgt catcaccgaa acgcgcgaga 5280
cgaaagggcc tcgtgatacg cctattttta taggttaatg tcatgataat aatggtttct 5340
tagacgtcag gtggcacttt tcggggaaat gtgcgcggaa cccctatttg tttatttttc 5400
taaatacatt caaatatgta tccgctcatg agacaataac cctgataaat gcttcaataa 5460
tattgaaaaa ggaagagtat gagtattcaa catttccgtg tcgcccttat tccctttttt 5520
gcggcatttt gccttcctgt ttttgctcac ccagaaacgc tggtgaaagt aaaagatgct 5580
gaagatcagt tgggtgcacg agtgggttac atcgaactgg atctcaacag cggtaagatc 5640
cttgagagtt ttcgccccga agaacgtttt ccaatgatga gcacttttaa agttctgcta 5700
tgtggcgcgg tattatcccg tgttgacgcc gggcaagagc aactcggtcg ccgcatacac 5760
tattctcaga atgacttggt tgagtactca ccagtcacag aaaagcatct tacggatggc 5820
atgacagtaa gagaattatg cagtgctgcc ataaccatga gtgataacac tgcggccaac 5880
ttacttctga caacgatcgg aggaccgaag gagctaaccg cttttttgca caacatgggg 5940
gatcatgtaa ctcgccttga tcgttgggaa ccggagctga atgaagccat accaaacgac 6000
gagcgtgaca ccacgatgcc tgtagcaatg gcaacaacgt tgcgcaaact attaactggc 6060
gaactactta ctctagcttc ccggcaacaa ttaatagact ggatggaggc ggataaagtt 6120
gcaggaccac ttctgcgctc ggcccttccg gctggctggt ttattgctga taaatctgga 6180
gccggtgagc gtgggtctcg cggtatcatt gcagcactgg ggccagatgg taagccctcc 6240
cgtatcgtag ttatctacac gacggggagt caggcaacta tggatgaacg aaatagacag 6300
atcgctgaga taggtgcctc actgattaag cattggtaac tgtcagacca agtttactca 6360
tatatacttt agattgattt aaaacttcat ttttaattta aaaggatcta ggtgaagatc 6420
ctttttgata atctcatgac caaaatccct taacgtgagt tttcgttcca ctgagcgtca 6480
gaccccgtag aaaagatcaa aggatcttct tgagatcctt tttttctgcg cgtaatctgc 6540
tgcttgcaaa caaaaaaacc accgctacca gcggtggttt gtttgccgga tcaagagcta 6600
ccaactcttt ttccgaaggt aactggcttc agcagagcgc agataccaaa tactgttctt 6660
ctagtgtagc cgtagttagg ccaccacttc aagaactctg tagcaccgcc tacatacctc 6720
gctctgctaa tcctgttacc agtggctgct gccagtggcg ataagtcgtg tcttaccggg 6780
ttggactcaa gacgatagtt accggataag gcgcagcggt cgggctgaac ggggggttcg 6840
tgcacacagc ccagcttgga gcgaacgacc tacaccgaac tgagatacct acagcgtgag 6900
ctatgagaaa gcgccacgct tcccgaaggg agaaaggcgg acaggtatcc ggtaagcggc 6960
agggtcggaa caggagagcg cacgagggag cttccagggg gaaacgcctg gtatctttat 7020
agtcctgtcg ggtttcgcca cctctgactt gagcgtcgat ttttgtgatg ctcgtcaggg 7080
gggcggagcc tatggaaaaa cgccagcaac gcggcctttt tacggttcct ggccttttgc 7140
tggccttttg ctcacatggc tcgacagatc t 7171

<210> SEQ ID NO 13
<211> LENGTH: 278
<212> TYPE: PRT
<213> ORGANISM: Artificial Sequence
<220> FEATURE:
<223> OTHER INFORMATION: Gal4 ASK1(e) fusion protein sequence

<400> SEQUENCE: 13

Met Lys Leu Leu Ser Ser Ile Glu Gln Ala Cys Asp Ile Cys Arg Leu
1 5 10 15

Lys Lys Leu Lys Cys Ser Lys Glu Lys Pro Lys Cys Ala Lys Cys Leu
20 25 30

Lys Asn Asn Trp Glu Cys Arg Tyr Ser Pro Lys Thr Lys Arg Ser Pro
35 40 45

Leu Thr Arg Ala His Leu Thr Glu Val Glu Ser Arg Leu Glu Arg Leu
50 55 60

Glu Gln Leu Phe Leu Leu Ile Phe Pro Arg Glu Asp Leu Asp Met Ile
65 70 75 80

Leu Lys Met Asp Ser Leu Gln Asp Ile Lys Ala Leu Leu Thr Gly Leu
85 90 95

Phe Val Gln Asp Asn Val Asn Lys Asp Ala Val Thr Asp Arg Leu Ala
100 105 110

Ser Val Glu Thr Asp Met Pro Leu Thr Leu Arg Gln His Arg Ile Ser
115 120 125

Ala Thr Ser Ser Ser Glu Glu Ser Ser Asn Lys Gly Gln Arg Gln Leu
130 135 140

Thr Val Ser Pro Glu Phe Pro Gly Ile Arg Thr Glu Asp Gln Asp Lys
145 150 155 160

Ile Val Arg Asn Leu Met Glu Ser Leu Ala Gln Gly Ala Glu Glu Pro
165 170 175

Lys Leu Lys Trp Glu His Ile Thr Thr Leu Ile Ala Ser Leu Arg Glu
180 185 190

Phe Val Arg Ser Thr Asp Arg Lys Ile Ile Ala Thr Thr Leu Ser Lys
195 200 205

Leu Lys Leu Glu Leu Asp Phe Asp Ser His Gly Ile Ser Gln Val Gln
210 215 220

Val Val Leu Phe Gly Phe Gln Asp Ala Val Asn Lys Val Leu Arg Asn
225 230 235 240

His Asn Ile Lys Pro His Trp Met Phe Ala Leu Asp Ser Ile Ile Arg
245 250 255

Lys Ala Val Gln Thr Ala Ile Thr Ile Leu Val Pro Glu Leu Arg Pro
260 265 270

His Phe Ser Leu Ala Ser
275

<210> SEQ ID NO 14
<211> LENGTH: 6981
<212> TYPE: DNA
<213> ORGANISM: Artificial Sequence
<220> FEATURE:
<223> OTHER INFORMATION: construct sequence containing ASK1(f) cloned in pBIND

<400> SEQUENCE: 14
tcaatattgg ccattagcca tattattcat tggttatata gcataaatca atattggcta 60
ttggccattg catacgttgt atctatatca taatatgtac atttatattg gctcatgtcc 120
aatatgaccg ccatgttggc attgattatt gactagttat taatagtaat caattacggg 180
gtcattagtt catagcccat atatggagtt ccgcgttaca taacttacgg taaatggccc 240
gcctggctga ccgcccaacg acccccgccc attgacgtca ataatgacgt atgttcccat 300
agtaacgcca atagggactt tccattgacg tcaatgggtg gagtatttac ggtaaactgc 360

-continued

```
ccacttggca gtacatcaag tgtatcatat gccaagtccg cccctattg acgtcaatga    420
cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt ttgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaggctag agtacttaat acgactcact   1080
ataggctagc cagcttgaag caagcctcct gaaagatgaa gctactgtct tctatcgaac   1140
aagcatgcga tatttgccga cttaaaaagc tcaagtgctc caaagaaaaa ccgaagtgcg   1200
ccaagtgtct gaagaacaac tgggagtgtc gctactctcc caaaaccaaa aggtctccgc   1260
tgactagggc acatctgaca gaagtggaat caaggctaga aagactggaa cagctatttc   1320
tactgatttt tcctcgagaa gaccttgaca tgattttgaa aatggattct ttacaggata   1380
taaaagcatt gttaacagga ttatttgtac aagataatgt gaataaagat gccgtcacag   1440
atagattggc ttcagtggag actgatatgc ctctaacatt gagacagcat agaataagtg   1500
cgacatcatc atcggaagag agtagtaaca aaggtcaaag acagttgact gtatcgccgg   1560
aattcccggg gatccgtgac agtatcattc ggaaggcggt acagacagcc attaccatcc   1620
tggttccaga actaaggcca catttcagcc ttgcatctga gagtgatact gctgatcaag   1680
aagacttgga tgtagaagat gaccatgagg aacagccttc aaatcaaact gtccgaagac   1740
ctcaggctgt cattgaagat gctgtggcta cctcaggcgt gagcacgctc agttctactg   1800
tgtctcatga ttcccagagt gctcaccggt cactgaatgt acagcttgga aggatgaaaa   1860
tagaaaccaa tagattactg gaagaattgg ttcggaaaga gaaagaatta caagcactcc   1920
ttcatcgagc tattgaagaa aaagaccaag aaattaaaca cctgaagctt aagtcccaac   1980
ccatagaaat tcctgaattg cctgtatttc atctaaattc ttctggcaca aatactgaag   2040
attctgaact taccgactgg ctgagagtga atggagctga tgaagacact ataagccggt   2100
ttttggctga agattataca ctattggatg ttctctacta tgttacacgt gatgacttaa   2160
aatgcttgag actaagggga gggatgctgt gcacactgtg gaaggctatt gactctagat   2220
ctagagcggc cgcaggtacc tgaataacta aggccgcttc cctttagtga gggttaatgc   2280
ttcgagcaga catgataaga tacattgatg agtttggaca aaccacaact agaatgcagt   2340
gaaaaaaatg ctttatttgt gaaatttgtg atgctattgc tttatttgta accattataa   2400
gctgcaataa acaagttaac aacaacaatt gcattcattt tatgtttcag gttcaggggg   2460
agatgtggga ggttttttaa agcaagtaaa acctctacaa atgtggtaaa atccgataag   2520
gatcgatccg ggctggcgta atagcgaaga ggcccgcacc gatcgccctt cccaacagtt   2580
gcgcagcctg aatggcgaat ggacgcgccc tgtagcggcg cattaagcgc ggcgggtgtg   2640
gtggttacgc gcagcgtgac cgctacactt gccagcgccc tagcgcccgc tcctttcgct   2700
```

ttcttccctt cctttcacgc cacgttcgcc ggctttcccc gtcaagctct aaatcggggg 2760
ctccctttag ggttccgatt tagtgcttta cggcacctcg accccaaaaa acttgattag 2820
ggtgatggtt cacgtagtgg gccatcgccc tgatagacgg tttttcgccc tttgacgttg 2880
gagtccacgt tctttaatag tggactcttg ttccaaactg gaacaacact caaccctatc 2940
tcggtctatt cttttgattt ataagggatt ttgccgattt cggcctattg gttaaaaaat 3000
gagctgattt aacaaaaatt taacgcgaat tttaacaaaa tattaacgct tacaatttcc 3060
tgatgcggta ttttctcctt acgcatctgt gcggtatttc acaccgcata cgcggatctt 3120
ccgtaccttc tgaggcggaa agaaccagct gtggaatgtg tgtcagttag ggtgtggaaa 3180
gtccccaggc tccccagcag gcagaagtat gcaaagcatg catctcaatt agtcagcaac 3240
caggtgtgga aagtccccag gctccccagc aggcagaagt atgcaaagca tgcatctcaa 3300
ttagtcagca accatagtcc cgcccctaac tccgcccatc ccgcccctaa ctccgcccag 3360
ttccgcccat tctccgcccc atggctgact aattttttt atttatgcag aggccgaggc 3420
cgcctcggcc tctgagctat tccagaagta gtgaggaggc ttttttggag gcctaggctt 3480
ttgcaaaaag cttgattctt ctgacacaac agtctcgaac ttaaggctag aattctggct 3540
acaggtaagc gcccctaaaa tccctttggg cacaatgtgt cctgagggga gaggcagcga 3600
cctgtagatg ggacgggggc actaaccctc aggtttgggg cttctgaatg tgagtatcgc 3660
catgtaagcc cagtatttgg ccaatctcag aaagctcctg gtccctggag ggatggagag 3720
agaaaaacaa acagctcctg gagcagggag agtgctggcc tcttgctctc cggctccctc 3780
tgttgccctc tggtttctcc ccaggctccc ggacgtcctc tagccaccat gacttcgaaa 3840
gtttatgatc cagaacaaag gaaacggatg ataactggtc cgcagtggtg ggccagatgt 3900
aaacaaatga atgttcttga ttcatttatt aattattatg attcagaaaa acatgcagaa 3960
aatgctgtta ttttttaca tggtaacgcg gcctcttctt atttatggcg acatgttgtg 4020
ccacatattg agccagtagc gcggtgtatt ataccagacc ttattggtat gggcaaatca 4080
ggcaaatctg gtaatggttc ttataggtta cttgatcatt acaaatatct tactgcatgg 4140
tttgaacttc ttaatttacc aaagaagatc atttttgtcg gccatgattg gggtgcttgt 4200
ttggcatttc attatagcta tgagcatcaa gataagatca aagcaatagt tcacgctgaa 4260
agtgtagtag atgtgattga atcatgggat gaatggcctg atattgaaga agatattgcg 4320
ttgatcaaat ctgaagaagg agaaaaaatg gttttggaga ataacttctt cgtggaaacc 4380
atgttgccat caaaaatcat gagaaagtta gaaccagaag aatttgcagc atatcttgaa 4440
ccattcaaag agaaaggtga agttcgtcgt ccaacattat catggcctcg tgaaatcccg 4500
ttagtaaaag gtggtaaacc tgacgttgta caaattgtta ggaattataa tgcttatcta 4560
cgtgcaagtg atgatttacc aaaaatgttt attgaatcgg acccaggatt cttttccaat 4620
gctattgttg aaggtgccaa gaagtttcct aatactgaat ttgtcaaagt aaaaggtctt 4680
catttttcgc aagaagatgc acctgatgaa atgggaaaat atatcaaatc gttcgttgag 4740
cgagttctca aaaatgaaca ataattctag ccctgaataa gtgataataa gcggatgaat 4800
ggcagaaatt cgtcgaagcg caataaaata tctttatttt cattacatct gtgtgttggt 4860
tttttgtgtg aatcgatagc gataaggatc ggaagatccg cgtatggtgc actctcagta 4920
caatctgctc tgatgccgca tagttaagcc agccccgaca cccgccaaca cccgctgacg 4980
cgccctgacg ggcttgtctg ctcccggcat ccgcttacag acaagctgtg accgtctccg 5040
ggagctgcat gtgtcagagg ttttcaccgt catcaccgaa acgcgcgaga cgaaagggcc 5100

```
tcgtgatacg cctattttta taggttaatg tcatgataat aatggtttct tagacgtcag   5160

gtggcacttt tcggggaaat gtgcgcggaa cccctatttg tttatttttc taaatacatt   5220

caaatatgta tccgctcatg agacaataac cctgataaat gcttcaataa tattgaaaaa   5280

ggaagagtat gagtattcaa catttccgtg tcgcccttat tccctttttt gcggcatttt   5340

gccttcctgt ttttgctcac ccagaaacgc tggtgaaagt aaaagatgct gaagatcagt   5400

tgggtgcacg agtgggttac atcgaactgg atctcaacag cggtaagatc cttgagagtt   5460

ttcgccccga agaacgtttt ccaatgatga gcacttttaa agttctgcta tgtggcgcgg   5520

tattatcccg tgttgacgcc gggcaagagc aactcggtcg ccgcatacac tattctcaga   5580

atgacttggt tgagtactca ccagtcacag aaaagcatct tacggatggc atgacagtaa   5640

gagaattatg cagtgctgcc ataaccatga gtgataacac tgcggccaac ttacttctga   5700

caacgatcgg aggaccgaag gagctaaccg cttttttgca caacatgggg gatcatgtaa   5760

ctcgccttga tcgttgggaa ccggagctga atgaagccat accaaacgac gagcgtgaca   5820

ccacgatgcc tgtagcaatg gcaacaacgt tgcgcaaact attaactggc gaactactta   5880

ctctagcttc ccggcaacaa ttaatagact ggatggaggc ggataaagtt gcaggaccac   5940

ttctgcgctc ggcccttccg gctggctggt ttattgctga taaatctgga gccggtgagc   6000

gtgggtctcg cggtatcatt gcagcactgg ggccagatgg taagccctcc cgtatcgtag   6060

ttatctacac gacggggagt caggcaacta tggatgaacg aaatagacag atcgctgaga   6120

taggtgcctc actgattaag cattggtaac tgtcagacca agtttactca tatatacttt   6180

agattgattt aaaacttcat ttttaattta aaaggatcta ggtgaagatc ctttttgata   6240

atctcatgac caaaatccct taacgtgagt tttcgttcca ctgagcgtca gaccccgtag   6300

aaaagatcaa aggatcttct tgagatcctt tttttctgcg cgtaatctgc tgcttgcaaa   6360

caaaaaaacc accgctacca gcggtggttt gtttgccgga tcaagagcta ccaactcttt   6420

ttccgaaggt aactggcttc agcagagcgc agataccaaa tactgttctt ctagtgtagc   6480

cgtagttagg ccaccacttc aagaactctg tagcaccgcc tacatacctc gctctgctaa   6540

tcctgttacc agtggctgct gccagtggcg ataagtcgtg tcttaccggg ttggactcaa   6600

gacgatagtt accggataag gcgcagcggt cgggctgaac ggggggttcg tgcacacagc   6660

ccagcttgga gcgaacgacc tacaccgaac tgagatacct acagcgtgag ctatgagaaa   6720

gcgccacgct tcccgaaggg agaaaggcgg acaggtatcc ggtaagcggc agggtcggaa   6780

caggagagcg cacgagggag cttccagggg gaaacgcctg gtatctttat agtcctgtcg   6840

ggtttcgcca cctctgactt gagcgtcgat ttttgtgatg ctcgtcaggg gggcggagcc   6900

tatggaaaaa cgccagcaac gcggcctttt tacggttcct ggccttttgc tggccttttg   6960

ctcacatggc tcgacagatc t                                             6981
```

```
<210> SEQ ID NO 15
<211> LENGTH: 368
<212> TYPE: PRT
<213> ORGANISM: Artificial Sequence
<220> FEATURE:
<223> OTHER INFORMATION: Gal4 ASK1(f) fusion protein sequence

<400> SEQUENCE: 15

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
```

-continued

```
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Pro Glu Phe Pro Gly Ile Arg Asp Ser Ile Ile Arg Lys
145                 150                 155                 160

Ala Val Gln Thr Ala Ile Thr Ile Leu Val Pro Glu Leu Arg Pro His
                165                 170                 175

Phe Ser Leu Ala Ser Glu Ser Asp Thr Ala Asp Gln Glu Asp Leu Asp
            180                 185                 190

Val Glu Asp Asp His Glu Glu Gln Pro Ser Asn Gln Thr Val Arg Arg
        195                 200                 205

Pro Gln Ala Val Ile Glu Asp Ala Val Ala Thr Ser Gly Val Ser Thr
    210                 215                 220

Leu Ser Ser Thr Val Ser His Asp Ser Gln Ser Ala His Arg Ser Leu
225                 230                 235                 240

Asn Val Gln Leu Gly Arg Met Lys Ile Glu Thr Asn Arg Leu Leu Glu
                245                 250                 255

Glu Leu Val Arg Lys Glu Lys Glu Leu Gln Ala Leu Leu His Arg Ala
            260                 265                 270

Ile Glu Glu Lys Asp Gln Glu Ile Lys His Leu Lys Leu Lys Ser Gln
        275                 280                 285

Pro Ile Glu Ile Pro Glu Leu Pro Val Phe His Leu Asn Ser Ser Gly
    290                 295                 300

Thr Asn Thr Glu Asp Ser Glu Leu Thr Asp Trp Leu Arg Val Asn Gly
305                 310                 315                 320

Ala Asp Glu Asp Thr Ile Ser Arg Phe Leu Ala Glu Asp Tyr Thr Leu
                325                 330                 335

Leu Asp Val Leu Tyr Tyr Val Thr Arg Asp Asp Leu Lys Cys Leu Arg
            340                 345                 350

Leu Arg Gly Gly Met Leu Cys Thr Leu Trp Lys Ala Ile Asp Ser Arg
        355                 360                 365
```

<210> SEQ ID NO 16
<211> LENGTH: 9485
<212> TYPE: DNA
<213> ORGANISM: Artificial Sequence
<220> FEATURE:
<223> OTHER INFORMATION: construct sequence containing ASK1(g) cloned in pBIND

<400> SEQUENCE: 16

```
tcaatattgg ccattagcca tattattcat tggttatata gcataaatca atattggcta      60

ttggccattg catacgttgt atctatatca taatatgtac atttatattg gctcatgtcc     120
```

-continued

```
aatatgaccg ccatgttggc attgattatt gactagttat taatagtaat caattacggg    180
gtcattagtt catagcccat atatggagtt ccgcgttaca taacttacgg taaatggccc    240
gcctggctga ccgcccaacg acccccgccc attgacgtca ataatgacgt atgttcccat    300
agtaacgcca atagggactt tccattgacg tcaatgggtg gagtatttac ggtaaactgc    360
ccacttggca gtacatcaag tgtatcatat gccaagtccg cccctattg acgtcaatga    420
cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt ttgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaggctag agtacttaat acgactcact   1080
ataggctagc cagcttgaag caagcctcct gaaagatgaa gctactgtct tctatcgaac   1140
aagcatgcga tatttgccga cttaaaaagc tcaagtgctc caaagaaaaa ccgaagtgcg   1200
ccaagtgtct gaagaacaac tgggagtgtc gctactctcc caaaaccaaa aggtctccgc   1260
tgactagggc acatctgaca gaagtggaat caaggctaga aagactggaa cagctatttc   1320
tactgatttt tcctcgagaa gaccttgaca tgattttgaa aatggattct ttacaggata   1380
taaaagcatt gttaacagga ttatttgtac aagataatgt gaataaagat gccgtcacag   1440
atagattggc ttcagtggag actgatatgc ctctaacatt gagacagcat agaataagtg   1500
cgacatcatc atcggaagag agtagtaaca aaggtcaaag acagttgact gtatcgccgg   1560
aattcccggg gatccgtacg gaggcggacg agggcatcac tttctctgtg ccacccttcg   1620
ccccctcggg cttctgcacc atccccgagg gcggcatctg caggaggga ggagcggcgg   1680
cggtgggcga gggcgaggag caccagctgc caccgccgcc gccgggcagt ttctggaacg   1740
tggagagcgc cgctgcccct ggcatcggtt gtccggcggc cacctcctcg agcagtgcca   1800
cccgaggccg gggcagctct gttggcgggg gcagccgacg gaccacggtg gcatatgtga   1860
tcaacgaagc gagccaaggg caactggtgg tggccgagag cgaggccctg cagagcttgc   1920
gggaggcgtg cgagacagtg ggcgccaccc tggaaaccct gcattttggg aaactcgact   1980
ttggagaaac caccgtgctg gaccgctttt acaatgcaga tattgcggtg gtggagatga   2040
gcgatgcctt ccggcagccg tccttgtttt accaccttgg ggtgagagaa agtttcagca   2100
tggccaacaa catcatcctc tactgtgata ctaactcgga ctctctgcag tcactgaagg   2160
aaatcatttg ccagaagaat actatgtgca ctgggaacta cacctttgtt ccttacatga   2220
taactccaca taacaaagtc tactgctgtg acagcagctt catgaagggg ttgacagagc   2280
tcatgcaacc gaacttcgag ctgcttcttg gacccatctg cttacctctt gtggatcgtt   2340
ttattcaact tttgaaggtg gcacaagcaa gttctagcca gtacttccgg gaatctatac   2400
tcaatgacat caggaaagct cgtaatttat acactggtaa agaattggca gctgagttgg   2460
```

-continued

```
caagaattcg gcagcgagta gataatatcg aagtcttgac agcagatatt gtcataaatc   2520
tgttactttc ctacagagat atccaggact atgattctat tgtgaagctg gtagagactt   2580
tagaaaaact gccaaccttt gatttggcct cccatcacca tgtgaagttt cattatgcat   2640
ttgcactgaa taggagaaat ctccctggtg acagagcaaa agctcttgat attatgattc   2700
ccatggtgca aagcgaagga caagttgctt cagatatgta ttgcctagtt ggtcgaatct   2760
acaaagatat gtttttggac tctaatttca cggacactga aagcagagac catggagctt   2820
cttggttcaa aaaggcattt gaatctgagc caacactaca gtcaggaatt aattatgcgg   2880
tcctcctcct ggcagctgga caccagtttg aatcttcctt tgagctccgg aaagttgggg   2940
tgaagctaag tagtcttctt ggtaaaaagg gaaacttgga aaaactccag agctactggg   3000
aagttggatt ttttctgggg gccagcgtcc tagccaatga ccacatgaga gtcattcaag   3060
catctgaaaa gcttttttaaa ctgaagacac cagcatggta cctcaagtct attgtagaga   3120
caattttaat atataagcat tttgtgaaac tgaccacaga acagcctgtg gccaagcaag   3180
aacttgtgga cttttggatg gatttcctgg tcgaggccac aaagacagat gttactgtgg   3240
ttaggtttcc agtattaata ttagaaccaa ccaaaatcta tcaaccttct tatttgtcta   3300
tcaacaatga agttgaggaa aagacaatct ctatttggca cgtgcttcct gatgacaaga   3360
aaggtataca tgagtggaat tttagtgcct cttctgtcag gggagtgagt atttctaaat   3420
ttgaagaaag atgctgcttt ctttatgtgc ttcacaattc tgatgatttc caaatctatt   3480
tctgtacaga acttcattgt aaaaagtttt ttgagatggt gaacaccatt accgaagaga   3540
aggggagaag cacagaggaa ggagactgtg aaagtgactt gctggagtat gactatgaat   3600
atgatgaaaa tggtgacaga gtcgttttag gaaaaggcac ttatgggata gtctacgcag   3660
gtcgggactt gagcaaccaa gtcagaattg ctattaagga aatcccagag agagacagca   3720
gatactctca gccccctgcat gaagaaatag cattgcataa acacctgaag cacaaaaata   3780
ttgtccagta tctgggctct ttcagtgaga atggtttcat taaaatcttc atggagcagg   3840
tccctggagg aagtctttct gctctccttc gttccaaatg gggtccatta aaagacaatg   3900
agcaaacaat tggcttttat acaaagcaaa tactggaagg attaaaatat ctccatgaca   3960
atcagatagt tcaccgggac ataaagggtg acaatgtgtt gattaatacc tacagtggtg   4020
ttctcaagat ctctgacttc ggaacatcaa agaggcttgc tggcataaac ccctgtactg   4080
aaacttttac tggtaccctc cagtatatgg caccagaaat aatagataaa ggaccaagag   4140
gctacggaaa agcagcagac atctggtctc tgggctgtac aatcattgaa atggccacag   4200
gaaaaccccc attttatgaa ctgggagaac cacaagcagc tatgttcaag gtgggaatgt   4260
ttaaagtcca ccctgagatc ccagagtcca tgtctgcaga ggccaaggca ttcatactga   4320
aatgttttga accagatcct gacaagagag cctgtgctaa cgacttgctt gttgatgagt   4380
ttttaaaagt ttcaagcaaa aagaaaaaga cacaacctaa gctttcagct ctttcagctg   4440
gatcaaatga atatctcagg agtatatcct tgccggtacc tgtgctggtg gaggacacca   4500
gcagcagcag tgagtacggc tcagtttcac ccgacacgga gttgaaagtg gacccttct   4560
ctttcaaaac aagagccaag tcctgcggag aaagagatgt caagggaatt cggacactct   4620
ttttgggcat tccagatgag aattttgaag atcacagtgc tcctccttcc cctgaagaaa   4680
aagattctgg attcttcatg ctgaggaagg acagtgagag gcgtctagag cggccgcagg   4740
tacctgaata actaaggccg cttcccttta gtgagggtta atgcttcgag cagacatgat   4800
aagatacatt gatgagtttg gacaaaccac aactagaatg cagtgaaaaa aatgctttat   4860
```

-continued

```
ttgtgaaatt tgtgatgcta ttgctttatt tgtaaccatt ataagctgca ataaacaagt   4920
taacaacaac aattgcattc attttatgtt tcaggttcag ggggagatgt gggaggtttt   4980
ttaaagcaag taaaacctct acaaatgtgg taaaatccga taaggatcga tccgggctgg   5040
cgtaatagcg aagaggcccg caccgatcgc ccttcccaac agttgcgcag cctgaatggc   5100
gaatggacgc gccctgtagc ggcgcattaa gcgcggcggg tgtggtggtt acgcgcagcg   5160
tgaccgctac acttgccagc gccctagcgc ccgctccttt cgctttcttc ccttcctttc   5220
acgccacgtt cgccggcttt ccccgtcaag ctctaaatcg ggggctccct ttagggttcc   5280
gatttagtgc tttacggcac ctcgacccca aaaaacttga ttagggtgat ggttcacgta   5340
gtgggccatc gccctgatag acggtttttc gccctttgac gttggagtcc acgttcttta   5400
atagtggact cttgttccaa actggaacaa cactcaaccc tatctcggtc tattcttttg   5460
atttataagg gattttgccg atttcggcct attggttaaa aaatgagctg atttaacaaa   5520
aatttaacgc gaattttaac aaaatattaa cgcttacaat ttcctgatgc ggtattttct   5580
ccttacgcat ctgtgcggta tttcacaccg catacgcgga tcttccgtac cttctgaggc   5640
ggaaagaacc agctgtggaa tgtgtgtcag ttagggtgtg gaaagtcccc aggctcccca   5700
gcaggcagaa gtatgcaaag catgcatctc aattagtcag caaccaggtg tggaaagtcc   5760
ccaggctccc cagcaggcag aagtatgcaa agcatgcatc tcaattagtc agcaaccata   5820
gtcccgcccc taactccgcc catcccgccc ctaactccgc ccagttccgc ccattctccg   5880
ccccatggct gactaatttt ttttatttat gcagaggccg aggccgcctc ggcctctgag   5940
ctattccaga agtagtgagg aggctttttt ggaggcctag gcttttgcaa aaagcttgat   6000
tcttctgaca caacagtctc gaacttaagg ctagaattct ggctacaggt aagcgcccct   6060
aaaatccctt tgggcacaat gtgtcctgag gggagaggca gcgacctgta gatgggacgg   6120
gggcactaac cctcaggttt ggggcttctg aatgtgagta tcgccatgta agcccagtat   6180
ttggccaatc tcagaaagct cctggtccct ggagggatgg agagagaaaa acaaacagct   6240
cctggagcag ggagagtgct ggcctcttgc tctccggctc cctctgttgc cctctggttt   6300
ctccccaggc tcccggacgt cctctagcca ccatgacttc gaaagtttat gatccagaac   6360
aaaggaaacg gatgataact ggtccgcagt ggtgggccag atgtaaacaa atgaatgttc   6420
ttgattcatt tattaattat tatgattcag aaaaacatgc agaaaatgct gttatttttt   6480
tacatggtaa cgcggcctct tcttatttat ggcgacatgt tgtgccacat attgagccag   6540
tagcgcggtg tattatacca gaccttattg gtatgggcaa atcaggcaaa tctggtaatg   6600
gttcttatag gttacttgat cattacaaat atcttactgc atggtttgaa cttcttaatt   6660
taccaaagaa gatcattttt gtcggccatg attggggtgc ttgtttggca tttcattata   6720
gctatgagca tcaagataag atcaaagcaa tagttcacgc tgaaagtgta gtagatgtga   6780
ttgaatcatg ggatgaatgg cctgatattg aagaagatat tgcgttgatc aaatctgaag   6840
aaggagaaaa aatggttttg gagaataact tcttcgtgga aaccatgttg ccatcaaaaa   6900
tcatgagaaa gttagaacca gaagaatttg cagcatatct tgaaccattc aaagagaaag   6960
gtgaagttcg tcgtccaaca ttatcatggc ctcgtgaaat cccgttagta aaaggtggta   7020
aacctgacgt tgtacaaatt gttaggaatt ataatgctta tctacgtgca agtgatgatt   7080
taccaaaaat gtttattgaa tcggacccag gattcttttc caatgctatt gttgaaggtg   7140
ccaagaagtt tcctaatact gaatttgtca aagtaaaagg tcttcatttt tcgcaagaag   7200
```

-continued

```
atgcacctga tgaaatggga aaatatatca aatcgttcgt tgagcgagtt ctcaaaaatg   7260
aacaataatt ctagccctga ataagtgata ataagcggat gaatggcaga aattcgtcga   7320
agcgcaataa aatatcttta ttttcattac atctgtgtgt tggttttttg tgtgaatcga   7380
tagcgataag gatcggaaga tccgcgtatg gtgcactctc agtacaatct gctctgatgc   7440
cgcatagtta agccagcccc gacacccgcc aacacccgct gacgcgccct gacgggcttg   7500
tctgctcccg gcatccgctt acagacaagc tgtgaccgtc tccgggagct gcatgtgtca   7560
gaggttttca ccgtcatcac cgaaacgcgc gagacgaaag ggcctcgtga tacgcctatt   7620
tttataggtt aatgtcatga taataatggt ttcttagacg tcaggtggca cttttcgggg   7680
aaatgtgcgc ggaaccccta tttgtttatt tttctaaata cattcaaata tgtatccgct   7740
catgagacaa taaccctgat aaatgcttca ataatattga aaaaggaaga gtatgagtat   7800
tcaacatttc cgtgtcgccc ttattccctt ttttgcggca ttttgccttc ctgtttttgc   7860
tcacccagaa acgctggtga aagtaaaaga tgctgaagat cagttgggtg cacgagtggg   7920
ttacatcgaa ctggatctca acagcggtaa gatccttgag agttttcgcc ccgaagaacg   7980
ttttccaatg atgagcactt ttaaagttct gctatgtggc gcggtattat cccgtgttga   8040
cgccgggcaa gagcaactcg gtcgccgcat acactattct cagaatgact tggttgagta   8100
ctcaccagtc acagaaaagc atcttacgga tggcatgaca gtaagagaat tatgcagtgc   8160
tgccataacc atgagtgata acactgcggc caacttactt ctgacaacga tcggaggacc   8220
gaaggagcta accgcttttt tgcacaacat gggggatcat gtaactcgcc ttgatcgttg   8280
ggaaccggag ctgaatgaag ccataccaaa cgacgagcgt gacaccacga tgcctgtagc   8340
aatggcaaca acgttgcgca aactattaac tggcgaacta cttactctag cttcccggca   8400
acaattaata gactggatgg aggcggataa agttgcagga ccacttctgc gctcggccct   8460
tccggctggc tggtttattg ctgataaatc tggagccggt gagcgtgggt ctcgcggtat   8520
cattgcagca ctggggccag atggtaagcc ctcccgtatc gtagttatct acacgacggg   8580
gagtcaggca actatggatg aacgaaatag acagatcgct gagataggtg cctcactgat   8640
taagcattgg taactgtcag accaagttta ctcatatata ctttagattg atttaaaact   8700
tcatttttaa tttaaaagga tctaggtgaa gatccttttt gataatctca tgaccaaaat   8760
cccttaacgt gagttttcgt tccactgagc gtcagacccc gtagaaaaga tcaaaggatc   8820
ttcttgagat cctttttttc tgcgcgtaat ctgctgcttg caaacaaaaa aaccaccgct   8880
accagcggtg gtttgtttgc cggatcaaga gctaccaact ctttttccga aggtaactgg   8940
cttcagcaga gcgcagatac caaatactgt tcttctagtg tagccgtagt taggccacca   9000
cttcaagaac tctgtagcac cgcctacata cctcgctctg ctaatcctgt taccagtggc   9060
tgctgccagt ggcgataagt cgtgtcttac cgggttggac tcaagacgat agttaccgga   9120
taaggcgcag cggtcgggct gaacgggggg ttcgtgcaca cagcccagct tggagcgaac   9180
gacctacacc gaactgagat acctacagcg tgagctatga gaaagcgcca cgcttcccga   9240
agggagaaag gcggacaggt atccggtaag cggcagggtc ggaacaggag agcgcacgag   9300
ggagcttcca gggggaaacg cctggtatct ttatagtcct gtcgggtttc gccacctctg   9360
acttgagcgt cgatttttgt gatgctcgtc aggggggcgg agcctatgga aaaacgccag   9420
caacgcggcc tttttacggt tcctggcctt ttgctggcct tttgctcaca tggctcgaca   9480
gatct                                                               9485
```

<210> SEQ ID NO 17
<211> LENGTH: 1202
<212> TYPE: PRT
<213> ORGANISM: Artificial Sequence
<220> FEATURE:
<223> OTHER INFORMATION: Gal4 ASK1(g) fusion protein sequence

<400> SEQUENCE: 17

```
Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Pro Glu Phe Pro Gly Ile Arg Thr Glu Ala Asp Glu Gly
145                 150                 155                 160

Ile Thr Phe Ser Val Pro Pro Phe Ala Pro Ser Gly Phe Cys Thr Ile
                165                 170                 175

Pro Glu Gly Gly Ile Cys Arg Arg Gly Gly Ala Ala Ala Val Gly Glu
            180                 185                 190

Gly Glu Glu His Gln Leu Pro Pro Pro Pro Pro Gly Ser Phe Trp Asn
        195                 200                 205

Val Glu Ser Ala Ala Ala Pro Gly Ile Gly Cys Pro Ala Ala Thr Ser
    210                 215                 220

Ser Ser Ser Ala Thr Arg Gly Arg Gly Ser Ser Val Gly Gly Gly Ser
225                 230                 235                 240

Arg Arg Thr Thr Val Ala Tyr Val Ile Asn Glu Ala Ser Gln Gly Gln
                245                 250                 255

Leu Val Val Ala Glu Ser Glu Ala Leu Gln Ser Leu Arg Glu Ala Cys
            260                 265                 270

Glu Thr Val Gly Ala Thr Leu Glu Thr Leu His Phe Gly Lys Leu Asp
        275                 280                 285

Phe Gly Glu Thr Thr Val Leu Asp Arg Phe Tyr Asn Ala Asp Ile Ala
    290                 295                 300

Val Val Glu Met Ser Asp Ala Phe Arg Gln Pro Ser Leu Phe Tyr His
305                 310                 315                 320

Leu Gly Val Arg Glu Ser Phe Ser Met Ala Asn Asn Ile Ile Leu Tyr
                325                 330                 335

Cys Asp Thr Asn Ser Asp Ser Leu Gln Ser Leu Lys Glu Ile Ile Cys
            340                 345                 350

Gln Lys Asn Thr Met Cys Thr Gly Asn Tyr Thr Phe Val Pro Tyr Met
        355                 360                 365

Ile Thr Pro His Asn Lys Val Tyr Cys Cys Asp Ser Ser Phe Met Lys
```

-continued

```
    370                 375                 380

Gly Leu Thr Glu Leu Met Gln Pro Asn Phe Glu Leu Leu Leu Gly Pro
385                 390                 395                 400

Ile Cys Leu Pro Leu Val Asp Arg Phe Ile Gln Leu Leu Lys Val Ala
                405                 410                 415

Gln Ala Ser Ser Ser Gln Tyr Phe Arg Glu Ser Ile Leu Asn Asp Ile
            420                 425                 430

Arg Lys Ala Arg Asn Leu Tyr Thr Gly Lys Glu Leu Ala Ala Glu Leu
        435                 440                 445

Ala Arg Ile Arg Gln Arg Val Asp Asn Ile Glu Val Leu Thr Ala Asp
    450                 455                 460

Ile Val Ile Asn Leu Leu Leu Ser Tyr Arg Asp Ile Gln Asp Tyr Asp
465                 470                 475                 480

Ser Ile Val Lys Leu Val Glu Thr Leu Glu Lys Leu Pro Thr Phe Asp
                485                 490                 495

Leu Ala Ser His His His Val Lys Phe His Tyr Ala Phe Ala Leu Asn
            500                 505                 510

Arg Arg Asn Leu Pro Gly Asp Arg Ala Lys Ala Leu Asp Ile Met Ile
        515                 520                 525

Pro Met Val Gln Ser Glu Gly Gln Val Ala Ser Asp Met Tyr Cys Leu
    530                 535                 540

Val Gly Arg Ile Tyr Lys Asp Met Phe Leu Asp Ser Asn Phe Thr Asp
545                 550                 555                 560

Thr Glu Ser Arg Asp His Gly Ala Ser Trp Phe Lys Lys Ala Phe Glu
                565                 570                 575

Ser Glu Pro Thr Leu Gln Ser Gly Ile Asn Tyr Ala Val Leu Leu Leu
            580                 585                 590

Ala Ala Gly His Gln Phe Glu Ser Ser Phe Glu Leu Arg Lys Val Gly
        595                 600                 605

Val Lys Leu Ser Ser Leu Leu Gly Lys Lys Gly Asn Leu Glu Lys Leu
    610                 615                 620

Gln Ser Tyr Trp Glu Val Gly Phe Phe Leu Gly Ala Ser Val Leu Ala
625                 630                 635                 640

Asn Asp His Met Arg Val Ile Gln Ala Ser Glu Lys Leu Phe Lys Leu
                645                 650                 655

Lys Thr Pro Ala Trp Tyr Leu Lys Ser Ile Val Glu Thr Ile Leu Ile
            660                 665                 670

Tyr Lys His Phe Val Lys Leu Thr Thr Glu Gln Pro Val Ala Lys Gln
        675                 680                 685

Glu Leu Val Asp Phe Trp Met Asp Phe Leu Val Glu Ala Thr Lys Thr
    690                 695                 700

Asp Val Thr Val Val Arg Phe Pro Val Leu Ile Leu Glu Pro Thr Lys
705                 710                 715                 720

Ile Tyr Gln Pro Ser Tyr Leu Ser Ile Asn Asn Glu Val Glu Glu Lys
                725                 730                 735

Thr Ile Ser Ile Trp His Val Leu Pro Asp Asp Lys Lys Gly Ile His
            740                 745                 750

Glu Trp Asn Phe Ser Ala Ser Ser Val Arg Gly Val Ser Ile Ser Lys
        755                 760                 765

Phe Glu Glu Arg Cys Cys Phe Leu Tyr Val Leu His Asn Ser Asp Asp
    770                 775                 780

Phe Gln Ile Tyr Phe Cys Thr Glu Leu His Cys Lys Lys Phe Phe Glu
785                 790                 795                 800
```

-continued

```
Met Val Asn Thr Ile Thr Glu Glu Lys Gly Arg Ser Thr Glu Glu Gly
                805                 810                 815

Asp Cys Glu Ser Asp Leu Leu Glu Tyr Asp Tyr Glu Tyr Asp Glu Asn
            820                 825                 830

Gly Asp Arg Val Val Leu Gly Lys Gly Thr Tyr Gly Ile Val Tyr Ala
        835                 840                 845

Gly Arg Asp Leu Ser Asn Gln Val Arg Ile Ala Ile Lys Glu Ile Pro
    850                 855                 860

Glu Arg Asp Ser Arg Tyr Ser Gln Pro Leu His Glu Glu Ile Ala Leu
865                 870                 875                 880

His Lys His Leu Lys His Lys Asn Ile Val Gln Tyr Leu Gly Ser Phe
                885                 890                 895

Ser Glu Asn Gly Phe Ile Lys Ile Phe Met Glu Gln Val Pro Gly Gly
            900                 905                 910

Ser Leu Ser Ala Leu Leu Arg Ser Lys Trp Gly Pro Leu Lys Asp Asn
        915                 920                 925

Glu Gln Thr Ile Gly Phe Tyr Thr Lys Gln Ile Leu Glu Gly Leu Lys
    930                 935                 940

Tyr Leu His Asp Asn Gln Ile Val His Arg Asp Ile Lys Gly Asp Asn
945                 950                 955                 960

Val Leu Ile Asn Thr Tyr Ser Gly Val Leu Lys Ile Ser Asp Phe Gly
                965                 970                 975

Thr Ser Lys Arg Leu Ala Gly Ile Asn Pro Cys Thr Glu Thr Phe Thr
            980                 985                 990

Gly Thr Leu Gln Tyr Met Ala Pro  Glu Ile Ile Asp Lys  Gly Pro Arg
        995                 1000                1005

Gly Tyr  Gly Lys Ala Ala Asp  Ile Trp Ser Leu Gly  Cys Thr Ile
    1010                1015                1020

Ile Glu  Met Ala Thr Gly Lys  Pro Pro Phe Tyr Glu  Leu Gly Glu
    1025                1030                1035

Pro Gln  Ala Ala Met Phe Lys  Val Gly Met Phe Lys  Val His Pro
    1040                1045                1050

Glu Ile  Pro Glu Ser Met Ser  Ala Glu Ala Lys Ala  Phe Ile Leu
    1055                1060                1065

Lys Cys  Phe Glu Pro Asp Pro  Asp Lys Arg Ala Cys  Ala Asn Asp
    1070                1075                1080

Leu Leu  Val Asp Glu Phe Leu  Lys Val Ser Ser Lys  Lys Lys Lys
    1085                1090                1095

Thr Gln  Pro Lys Leu Ser Ala  Leu Ser Ala Gly Ser  Asn Glu Tyr
    1100                1105                1110

Leu Arg  Ser Ile Ser Leu Pro  Val Pro Val Leu Val  Glu Asp Thr
    1115                1120                1125

Ser Ser  Ser Ser Glu Tyr Gly  Ser Val Ser Pro Asp  Thr Glu Leu
    1130                1135                1140

Lys Val  Asp Pro Phe Ser Phe  Lys Thr Arg Ala Lys  Ser Cys Gly
    1145                1150                1155

Glu Arg  Asp Val Lys Gly Ile  Arg Thr Leu Phe Leu  Gly Ile Pro
    1160                1165                1170

Asp Glu  Asn Phe Glu Asp His  Ser Ala Pro Pro Ser  Pro Glu Glu
    1175                1180                1185

Lys Asp  Ser Gly Phe Phe Met  Leu Arg Lys Asp Ser  Glu Arg
    1190                1195                1200
```

<210> SEQ ID NO 18
<211> LENGTH: 8541
<212> TYPE: DNA
<213> ORGANISM: Artificial Sequence
<220> FEATURE:
<223> OTHER INFORMATION: construct sequence containing ASK1(h) cloned in pBIND

<400> SEQUENCE: 18
tcaatattgg ccattagcca tattattcat tggttatata gcataaatca atattggcta 60
ttggccattg catacgttgt atctatatca taatatgtac atttatattg gctcatgtcc 120
aatatgaccg ccatgttggc attgattatt gactagttat taatagtaat caattacggg 180
gtcattagtt catagcccat atatggagtt ccgcgttaca taacttacgg taaatggccc 240
gcctggctga ccgcccaacg acccccgccc attgacgtca ataatgacgt atgttcccat 300
agtaacgcca atagggactt tccattgacg tcaatgggtg gagtatttac ggtaaactgc 360
ccacttggca gtacatcaag tgtatcatat gccaagtccg cccccctattg acgtcaatga 420 cggtaaatgg cccgcctggc attatgccca gtacatgacc ttacgggact ttcctacttg 480
gcagtacatc tacgtattag tcatcgctat taccatggtg atgcggtttt ggcagtacac 540
caatgggcgt ggatagcggt ttgactcacg gggatttcca agtctccacc ccattgacgt 600
caatgggagt ttgttttggc accaaaatca acgggacttt ccaaaatgtc gtaacaactg 660
cgatcgcccg ccccgttgac gcaaatgggc ggtaggcgtg tacggtggga ggtctatata 720
agcagagctc gtttagtgaa ccgtcagatc actagaagct ttattgcggt agtttatcac 780
agttaaattg ctaacgcagt cagtgcttct gacacaacag tctcgaactt aagctgcagt 840
gactctctta aggtagcctt gcagaagttg gtcgtgaggc actgggcagg taagtatcaa 900
ggttacaaga caggtttaag gagaccaata gaaactgggc ttgtcgagac agagaagact 960
cttgcgtttc tgataggcac ctattggtct tactgacatc cactttgcct ttctctccac 1020
aggtgtccac tcccagttca attacagctc ttaaggctag agtacttaat acgactcact 1080
ataggctagc cagcttgaag caagcctcct gaaagatgaa gctactgtct tctatcgaac 1140
aagcatgcga tatttgccga cttaaaaagc tcaagtgctc caaagaaaaa ccgaagtgcg 1200
ccaagtgtct gaagaacaac tgggagtgtc gctactctcc caaaaccaaa aggtctccgc 1260
tgactagggc acatctgaca gaagtggaat caaggctaga aagactggaa cagctatttc 1320
tactgatttt tcctcgagaa gaccttgaca tgattttgaa aatggattct ttacaggata 1380
taaaagcatt gttaacagga ttatttgtac aagataatgt gaataaagat gccgtcacag 1440
atagattggc ttcagtggag actgatatgc ctctaacatt gagacagcat agaataagtg 1500
cgacatcatc atcggaagag agtagtaaca aaggtcaaag acagttgact gtatcgccgg 1560
aattcccggg gatccgttcc tacagagata tccaggacta tgattctatt gtgaagctgg 1620
tagagacttt agaaaaactg ccaacctttg atttggcctc ccatcaccat gtgaagtttc 1680
attatgcatt tgcactgaat aggagaaatc tccctggtga cagagcaaaa gctcttgata 1740
ttatgattcc catggtgcaa agcgaaggac aagttgcttc agatatgtat tgcctagttg 1800
gtcgaatcta caaagatatg tttttggact ctaatttcac ggacactgaa agcagagacc 1860
atggagcttc ttggttcaaa aaggcatttg aatctgagcc aacactacag tcaggaatta 1920
attatgcggt cctcctcctg gcagctggac accagtttga atcttccttt gagctccgga 1980
aagttggggt gaagctaagt agtcttcttg gtaaaaaggg aaacttggaa aaactccaga 2040

```
gctactggga agttggattt tttctggggg ccagcgtcct agccaatgac cacatgagag   2100
tcattcaagc atctgaaaag ctttttaaac tgaagacacc agcatggtac ctcaagtcta   2160
ttgtagagac aattttaata tataagcatt ttgtgaaact gaccacagaa cagcctgtgg   2220
ccaagcaaga acttgtggac ttttggatgg atttcctggt cgaggccaca aagacagatg   2280
ttactgtggt taggtttcca gtattaatat tagaaccaac caaaatctat caaccttctt   2340
atttgtctat caacaatgaa gttgaggaaa agacaatctc tatttggcac gtgcttcctg   2400
atgacaagaa aggtatacat gagtggaatt ttagtgcctc ttctgtcagg ggagtgagta   2460
tttctaaatt tgaagaaaga tgctgctttc tttatgtgct tcacaattct gatgatttcc   2520
aaatctattt ctgtacagaa cttcattgta aaaagttttt tgagatggtg aacaccatta   2580
ccgaagagaa ggggagaagc acagaggaag gagactgtga aagtgacttg ctggagtatg   2640
actatgaata tgatgaaaat ggtgacagag tcgttttagg aaaaggcact tatgggatag   2700
tctacgcagg tcgggacttg agcaaccaag tcagaattgc tattaaggaa atcccagaga   2760
gagacagcag atactctcag cccctgcatg aagaaatagc attgcataaa cacctgaagc   2820
acaaaaatat tgtccagtat ctgggctctt tcagtgagaa tggtttcatt aaaatcttca   2880
tggagcaggt ccctggagga agtctttctg ctctccttcg ttccaaatgg ggtccattaa   2940
aagacaatga gcaaacaatt ggcttttata caaagcaaat actggaagga ttaaaatatc   3000
tccatgacaa tcagatagtt caccgggaca taaagggtga caatgtgttg attaatacct   3060
acagtggtgt tctcaagatc tctgacttcg gaacatcaaa gaggcttgct ggcataaacc   3120
cctgtactga aacttttact ggtaccctcc agtatatggc accagaaata atagataaag   3180
gaccaagagg ctacggaaaa gcagcagaca tctggtctct gggctgtaca atcattgaaa   3240
tggccacagg aaaacccccca ttttatgaac tgggagaacc acaagcagct atgttcaagg   3300
tgggaatgtt taaagtccac cctgagatcc cagagtccat gtctgcagag gccaaggcat   3360
tcatactgaa atgttttgaa ccagatcctg acaagagagc ctgtgctaac gacttgcttg   3420
ttgatgagtt tttaaaagtt tcaagcaaaa agaaaaagac acaacctaag ctttcagctc   3480
tttcagctgg atcaaatgaa tatctcagga gtatatcctt gccggtacct gtgctggtgg   3540
aggacaccag cagcagcagt gagtacggct cagtttcacc cgacacggag ttgaaagtgg   3600
acccccttctc tttcaaaaca agagccaagt cctgcggaga aagagatgtc aagggaattc   3660
ggacactctt tttgggcatt ccagatgaga attttgaaga tcacagtgct cctccttccc   3720
ctgaagaaaa agattctgga ttcttcatgc tgaggaagga cagtgagagg cgatctagat   3780
ctagagcggc cgcaggtacc tgaataacta aggccgcttc cctttagtga gggttaatgc   3840
ttcgagcaga catgataaga tacattgatg agtttggaca aaccacaact agaatgcagt   3900
gaaaaaaatg ctttatttgt gaaatttgtg atgctattgc tttatttgta accattataa   3960
gctgcaataa acaagttaac aacaacaatt gcattcattt tatgtttcag gttcaggggg   4020
agatgtggga ggttttttaa agcaagtaaa acctctacaa atgtggtaaa atccgataag   4080
gatcgatccg ggctggcgta atagcgaaga ggcccgcacc gatcgccctt cccaacagtt   4140
gcgcagcctg aatggcgaat ggacgcgccc tgtagcggcg cattaagcgc ggcgggtgtg   4200
gtggttacgc gcagcgtgac cgctacactt gccagcgccc tagcgcccgc tcctttcgct   4260
ttcttccctt cctttcacgc cacgttcgcc ggctttcccc gtcaagctct aaatcggggg   4320
ctccctttag ggttccgatt tagtgcttta cggcacctcg accccaaaaa acttgattag   4380
ggtgatggtt cacgtagtgg gccatcgccc tgatagacgg tttttcgccc tttgacgttg   4440
```

-continued

```
gagtccacgt tctttaatag tggactcttg ttccaaactg gaacaacact caaccctatc   4500
tcggtctatt cttttgattt ataagggatt ttgccgattt cggcctattg gttaaaaaat   4560
gagctgattt aacaaaaatt taacgcgaat tttaacaaaa tattaacgct tacaatttcc   4620
tgatgcggta ttttctcctt acgcatctgt gcggtatttc acaccgcata cgcggatctt   4680
ccgtaccttc tgaggcggaa agaaccagct gtggaatgtg tgtcagttag ggtgtggaaa   4740
gtccccaggc tccccagcag gcagaagtat gcaaagcatg catctcaatt agtcagcaac   4800
caggtgtgga aagtccccag gctccccagc aggcagaagt atgcaaagca tgcatctcaa   4860
ttagtcagca accatagtcc cgcccctaac tccgcccatc ccgcccctaa ctccgcccag   4920
ttccgcccat tctccgcccc atggctgact aatttttttt atttatgcag aggccgaggc   4980
cgcctcggcc tctgagctat tccagaagta gtgaggaggc ttttttggag gcctaggctt   5040
ttgcaaaaag cttgattctt ctgacacaac agtctcgaac ttaaggctag aattctggct   5100
acaggtaagc gcccctaaaa tccctttggg cacaatgtgt cctgagggga gaggcagcga   5160
cctgtagatg ggacgggggc actaaccctc aggtttgggg cttctgaatg tgagtatcgc   5220
catgtaagcc cagtatttgg ccaatctcag aaagctcctg gtccctggag ggatggagag   5280
agaaaaacaa acagctcctg gagcagggag agtgctggcc tcttgctctc cggctccctc   5340
tgttgccctc tggtttctcc ccaggctccc ggacgtcctc tagccaccat gacttcgaaa   5400
gtttatgatc cagaacaaag gaaacggatg ataactggtc cgcagtggtg ggccagatgt   5460
aaacaaatga atgttcttga ttcatttatt aattattatg attcagaaaa acatgcagaa   5520
aatgctgtta ttttttttaca tggtaacgcg gcctcttctt atttatggcg acatgttgtg   5580
ccacatattg agccagtagc gcggtgtatt ataccagacc ttattggtat gggcaaatca   5640
ggcaaatctg gtaatggttc ttataggtta cttgatcatt acaaatatct tactgcatgg   5700
tttgaacttc ttaatttacc aaagaagatc atttttgtcg gccatgattg gggtgcttgt   5760
ttggcatttc attatagcta tgagcatcaa gataagatca aagcaatagt tcacgctgaa   5820
agtgtagtag atgtgattga atcatgggat gaatggcctg atattgaaga agatattgcg   5880
ttgatcaaat ctgaagaagg agaaaaaatg gttttggaga ataacttctt cgtggaaacc   5940
atgttgccat caaaaatcat gagaaagtta gaaccagaag aatttgcagc atatcttgaa   6000
ccattcaaag agaaaggtga agttcgtcgt ccaacattat catggcctcg tgaaatcccg   6060
ttagtaaaag gtggtaaacc tgacgttgta caaattgtta ggaattataa tgcttatcta   6120
cgtgcaagtg atgatttacc aaaaatgttt attgaatcgg acccaggatt cttttccaat   6180
gctattgttg aaggtgccaa gaagtttcct aatactgaat ttgtcaaagt aaaaggtctt   6240
catttttcgc aagaagatgc acctgatgaa atgggaaaat atatcaaatc gttcgttgag   6300
cgagttctca aaaatgaaca ataattctag ccctgaataa gtgataataa gcggatgaat   6360
ggcagaaatt cgtcgaagcg caataaaata tctttatttt cattacatct gtgtgttggt   6420
tttttgtgtg aatcgatagc gataaggatc ggaagatccg cgtatggtgc actctcagta   6480
caatctgctc tgatgccgca tagttaagcc agccccgaca cccgccaaca cccgctgacg   6540
cgccctgacg ggcttgtctg ctcccggcat ccgcttacag acaagctgtg accgtctccg   6600
ggagctgcat gtgtcagagg ttttcaccgt catcaccgaa acgcgcgaga cgaaagggcc   6660
tcgtgatacg cctattttta taggttaatg tcatgataat aatggtttct tagacgtcag   6720
gtggcacttt tcggggaaat gtgcgcggaa cccctatttg tttatttttc taaatacatt   6780
```

-continued caaatatgta tccgctcatg agacaataac cctgataaat gcttcaataa tattgaaaaa 6840
ggaagagtat gagtattcaa catttccgtg tcgcccttat tccctttttt gcggcatttt 6900
gccttcctgt ttttgctcac ccagaaacgc tggtgaaagt aaaagatgct gaagatcagt 6960
tgggtgcacg agtgggttac atcgaactgg atctcaacag cggtaagatc cttgagagtt 7020
ttcgccccga agaacgtttt ccaatgatga gcacttttaa agttctgcta tgtggcgcgg 7080
tattatcccg tgttgacgcc gggcaagagc aactcggtcg ccgcatacac tattctcaga 7140
atgacttggt tgagtactca ccagtcacag aaaagcatct tacggatggc atgacagtaa 7200
gagaattatg cagtgctgcc ataaccatga gtgataacac tgcggccaac ttacttctga 7260
caacgatcgg aggaccgaag gagctaaccg cttttttgca caacatgggg gatcatgtaa 7320
ctcgccttga tcgttgggaa ccggagctga atgaagccat accaaacgac gagcgtgaca 7380
ccacgatgcc tgtagcaatg gcaacaacgt tgcgcaaact attaactggc gaactactta 7440
ctctagcttc ccggcaacaa ttaatagact ggatggaggc ggataaagtt gcaggaccac 7500
ttctgcgctc ggcccttccg gctggctggt ttattgctga taaatctgga gccggtgagc 7560
gtgggtctcg cggtatcatt gcagcactgg ggccagatgg taagccctcc cgtatcgtag 7620
ttatctacac gacggggagt caggcaacta tggatgaacg aaatagacag atcgctgaga 7680
taggtgcctc actgattaag cattggtaac tgtcagacca agtttactca tatatacttt 7740
agattgattt aaaacttcat ttttaattta aaaggatcta ggtgaagatc ctttttgata 7800
atctcatgac caaaatccct taacgtgagt tttcgttcca ctgagcgtca gaccccgtag 7860
aaaagatcaa aggatcttct tgagatcctt tttttctgcg cgtaatctgc tgcttgcaaa 7920
caaaaaaacc accgctacca gcggtggttt gtttgccgga tcaagagcta ccaactcttt 7980
ttccgaaggt aactggcttc agcagagcgc agataccaaa tactgttctt ctagtgtagc 8040
cgtagttagg ccaccacttc aagaactctg tagcaccgcc tacatacctc gctctgctaa 8100
tcctgttacc agtggctgct gccagtggcg ataagtcgtg tcttaccggg ttggactcaa 8160
gacgatagtt accggataag gcgcagcggt cgggctgaac ggggggttcg tgcacacagc 8220
ccagcttgga gcgaacgacc tacaccgaac tgagatacct acagcgtgag ctatgagaaa 8280
gcgccacgct tcccgaaggg agaaaggcgg acaggtatcc ggtaagcggc agggtcggaa 8340
caggagagcg cacgagggag cttccagggg gaaacgcctg gtatctttat agtcctgtcg 8400
ggtttcgcca cctctgactt gagcgtcgat ttttgtgatg ctcgtcaggg gggcggagcc 8460
tatggaaaaa cgccagcaac gcggcctttt tacggttcct ggccttttgc tggccttttg 8520
ctcacatggc tcgacagatc t 8541

<210> SEQ ID NO 19
<211> LENGTH: 888
<212> TYPE: PRT
<213> ORGANISM: Artificial Sequence
<220> FEATURE:
<223> OTHER INFORMATION: Gal4 ASK1(h) fusion protein sequence

<400> SEQUENCE: 19

Met Lys Leu Leu Ser Ser Ile Glu Gln Ala Cys Asp Ile Cys Arg Leu
1 5 10 15

Lys Lys Leu Lys Cys Ser Lys Glu Lys Pro Lys Cys Ala Lys Cys Leu
20 25 30

Lys Asn Asn Trp Glu Cys Arg Tyr Ser Pro Lys Thr Lys Arg Ser Pro
35 40 45

-continued

```
Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Pro Glu Phe Pro Gly Ile Arg Ser Tyr Arg Asp Ile Gln
145                 150                 155                 160

Asp Tyr Asp Ser Ile Val Lys Leu Val Glu Thr Leu Glu Lys Leu Pro
                165                 170                 175

Thr Phe Asp Leu Ala Ser His His His Val Lys Phe His Tyr Ala Phe
            180                 185                 190

Ala Leu Asn Arg Arg Asn Leu Pro Gly Asp Arg Ala Lys Ala Leu Asp
        195                 200                 205

Ile Met Ile Pro Met Val Gln Ser Glu Gly Gln Val Ala Ser Asp Met
    210                 215                 220

Tyr Cys Leu Val Gly Arg Ile Tyr Lys Asp Met Phe Leu Asp Ser Asn
225                 230                 235                 240

Phe Thr Asp Thr Glu Ser Arg Asp His Gly Ala Ser Trp Phe Lys Lys
                245                 250                 255

Ala Phe Glu Ser Glu Pro Thr Leu Gln Ser Gly Ile Asn Tyr Ala Val
            260                 265                 270

Leu Leu Leu Ala Ala Gly His Gln Phe Glu Ser Ser Phe Glu Leu Arg
        275                 280                 285

Lys Val Gly Val Lys Leu Ser Ser Leu Leu Gly Lys Lys Gly Asn Leu
    290                 295                 300

Glu Lys Leu Gln Ser Tyr Trp Glu Val Gly Phe Phe Leu Gly Ala Ser
305                 310                 315                 320

Val Leu Ala Asn Asp His Met Arg Val Ile Gln Ala Ser Glu Lys Leu
                325                 330                 335

Phe Lys Leu Lys Thr Pro Ala Trp Tyr Leu Lys Ser Ile Val Glu Thr
            340                 345                 350

Ile Leu Ile Tyr Lys His Phe Val Lys Leu Thr Thr Glu Gln Pro Val
        355                 360                 365

Ala Lys Gln Glu Leu Val Asp Phe Trp Met Asp Phe Leu Val Glu Ala
    370                 375                 380

Thr Lys Thr Asp Val Thr Val Val Arg Phe Pro Val Leu Ile Leu Glu
385                 390                 395                 400

Pro Thr Lys Ile Tyr Gln Pro Ser Tyr Leu Ser Ile Asn Asn Glu Val
                405                 410                 415

Glu Glu Lys Thr Ile Ser Ile Trp His Val Leu Pro Asp Asp Lys Lys
            420                 425                 430

Gly Ile His Glu Trp Asn Phe Ser Ala Ser Ser Val Arg Gly Val Ser
        435                 440                 445

Ile Ser Lys Phe Glu Glu Arg Cys Cys Phe Leu Tyr Val Leu His Asn
    450                 455                 460

Ser Asp Asp Phe Gln Ile Tyr Phe Cys Thr Glu Leu His Cys Lys Lys
```

-continued

```
465                 470                 475                 480

Phe Phe Glu Met Val Asn Thr Ile Thr Glu Glu Lys Gly Arg Ser Thr
                485                 490                 495

Glu Glu Gly Asp Cys Glu Ser Asp Leu Leu Glu Tyr Asp Tyr Glu Tyr
            500                 505                 510

Asp Glu Asn Gly Asp Arg Val Val Leu Gly Lys Gly Thr Tyr Gly Ile
        515                 520                 525

Val Tyr Ala Gly Arg Asp Leu Ser Asn Gln Val Arg Ile Ala Ile Lys
    530                 535                 540

Glu Ile Pro Glu Arg Asp Ser Arg Tyr Ser Gln Pro Leu His Glu Glu
545                 550                 555                 560

Ile Ala Leu His Lys His Leu Lys His Lys Asn Ile Val Gln Tyr Leu
                565                 570                 575

Gly Ser Phe Ser Glu Asn Gly Phe Ile Lys Ile Phe Met Glu Gln Val
            580                 585                 590

Pro Gly Gly Ser Leu Ser Ala Leu Leu Arg Ser Lys Trp Gly Pro Leu
        595                 600                 605

Lys Asp Asn Glu Gln Thr Ile Gly Phe Tyr Thr Lys Gln Ile Leu Glu
    610                 615                 620

Gly Leu Lys Tyr Leu His Asp Asn Gln Ile Val His Arg Asp Ile Lys
625                 630                 635                 640

Gly Asp Asn Val Leu Ile Asn Thr Tyr Ser Gly Val Leu Lys Ile Ser
                645                 650                 655

Asp Phe Gly Thr Ser Lys Arg Leu Ala Gly Ile Asn Pro Cys Thr Glu
            660                 665                 670

Thr Phe Thr Gly Thr Leu Gln Tyr Met Ala Pro Glu Ile Ile Asp Lys
        675                 680                 685

Gly Pro Arg Gly Tyr Gly Lys Ala Ala Asp Ile Trp Ser Leu Gly Cys
    690                 695                 700

Thr Ile Ile Glu Met Ala Thr Gly Lys Pro Pro Phe Tyr Glu Leu Gly
705                 710                 715                 720

Glu Pro Gln Ala Ala Met Phe Lys Val Gly Met Phe Lys Val His Pro
                725                 730                 735

Glu Ile Pro Glu Ser Met Ser Ala Glu Ala Lys Ala Phe Ile Leu Lys
            740                 745                 750

Cys Phe Glu Pro Asp Pro Asp Lys Arg Ala Cys Ala Asn Asp Leu Leu
        755                 760                 765

Val Asp Glu Phe Leu Lys Val Ser Ser Lys Lys Lys Lys Thr Gln Pro
    770                 775                 780

Lys Leu Ser Ala Leu Ser Ala Gly Ser Asn Glu Tyr Leu Arg Ser Ile
785                 790                 795                 800

Ser Leu Pro Val Pro Val Leu Val Glu Asp Thr Ser Ser Ser Ser Glu
                805                 810                 815

Tyr Gly Ser Val Ser Pro Asp Thr Glu Leu Lys Val Asp Pro Phe Ser
            820                 825                 830

Phe Lys Thr Arg Ala Lys Ser Cys Gly Glu Arg Asp Val Lys Gly Ile
        835                 840                 845

Arg Thr Leu Phe Leu Gly Ile Pro Asp Glu Asn Phe Glu Asp His Ser
    850                 855                 860

Ala Pro Pro Ser Pro Glu Glu Lys Asp Ser Gly Phe Phe Met Leu Arg
865                 870                 875                 880

Lys Asp Ser Glu Arg Arg Ser Arg
                885
```

<210> SEQ ID NO 20
<211> LENGTH: 9046
<212> TYPE: DNA
<213> ORGANISM: Artificial Sequence
<220> FEATURE:
<223> OTHER INFORMATION: construct sequence containing ASK1(i) cloned in pBIND

<400> SEQUENCE: 20
tcaatattgg ccattagcca tattattcat tggttatata gcataaatca atattggcta 60
ttggccattg catacgttgt atctatatca taatatgtac atttatattg gctcatgtcc 120
aatatgaccg ccatgttggc attgattatt gactagttat taatagtaat caattacggg 180
gtcattagtt catagcccat atatggagtt ccgcgttaca taacttacgg taaatggccc 240
gcctggctga ccgcccaacg acccccgccc attgacgtca ataatgacgt atgttcccat 300
agtaacgcca atagggactt tccattgacg tcaatgggtg gagtatttac ggtaaactgc 360
ccacttggca gtacatcaag tgtatcatat gccaagtccg ccccctattg acgtcaatga 420
cggtaaatgg cccgcctggc attatgccca gtacatgacc ttacgggact ttcctacttg 480
gcagtacatc tacgtattag tcatcgctat taccatggtg atgcggtttt ggcagtacac 540
caatgggcgt ggatagcggt ttgactcacg gggatttcca agtctccacc ccattgacgt 600
caatgggagt ttgttttggc accaaaatca acgggacttt ccaaaatgtc gtaacaactg 660
cgatcgcccg ccccgttgac gcaaatgggc ggtaggcgtg tacggtggga ggtctatata 720
agcagagctc gtttagtgaa ccgtcagatc actagaagct ttattgcggt agtttatcac 780
agttaaattg ctaacgcagt cagtgcttct gacacaacag tctcgaactt aagctgcagt 840
gactctctta aggtagcctt gcagaagttg gtcgtgaggc actgggcagg taagtatcaa 900
ggttacaaga caggtttaag gagaccaata gaaactgggc ttgtcgagac agagaagact 960
cttgcgtttc tgataggcac ctattggtct tactgacatc cactttgcct ttctctccac 1020
aggtgtccac tcccagttca attacagctc ttaaggctag agtacttaat acgactcact 1080
ataggctagc cagcttgaag caagcctcct gaaagatgaa gctactgtct tctatcgaac 1140
aagcatgcga tatttgccga cttaaaaagc tcaagtgctc caaagaaaaa ccgaagtgcg 1200
ccaagtgtct gaagaacaac tgggagtgtc gctactctcc caaaaccaaa aggtctccgc 1260
tgactagggc acatctgaca gaagtggaat caaggctaga aagactggaa cagctatttc 1320
tactgatttt tcctcgagaa gaccttgaca tgattttgaa aatggattct ttacaggata 1380
taaaagcatt gttaacagga ttatttgtac aagataatgt gaataaagat gccgtcacag 1440
atagattggc ttcagtggag actgatatgc ctctaacatt gagacagcat agaataagtg 1500
cgacatcatc atcggaagag agtagtaaca aaggtcaaag acagttgact gtatcgccgg 1560
aattcccggg gatccgtacg gaggcggacg agggcatcac tttctctgtg ccacccttcg 1620
ccccctcggg cttctgcacc atccccgagg gcggcatctg caggagggga ggagcggcgg 1680
cggtgggcga gggcgaggag caccagctgc caccgccgcc gccgggcagt ttctggaacg 1740
tggagagcgc cgctgcccct ggcatcggtt gtccggcggc cacctcctcg agcagtgcca 1800
cccgaggccg gggcagctct gttggcgggg gcagccgacg gaccacggtg gcatatgtga 1860
tcaacgaagc gagccaaggg caactggtgg tggccgagag cgaggccctg cagagcttgc 1920
gggaggcgtg cgagacagtg ggcgccaccc tggaaaccct gcattttggg aaactcgact 1980
ttggagaaac caccgtgctg gaccgctttt acaatgcaga tattgcggtg gtggagatga 2040

```
gcgatgcctt ccggcagccg tccttgtttt accaccttgg ggtgagagaa agtttcagca   2100
tggccaacaa catcatcctc tactgtgata ctaactcgga ctctctgcag tcactgaagg   2160
aaatcatttg ccagaagaat actatgtgca ctgggaacta cacctttgtt ccttacatga   2220
taactccaca taacaaagtc tactgctgtg acagcagctt catgaagggg ttgacagagc   2280
tcatgcaacc gaacttcgag ctgcttcttg gacccatctg cttacctctt gtggatcgtt   2340
ttattcaact tttgaaggtg gcacaagcaa gttctagcca gtacttccgg gaatctatac   2400
tcaatgacat caggaaagct cgtaatttat acactggtaa agaattggca gctgagttgg   2460
caagaattcg gcagcgagta gataatatcg aagtcttgac agcagatatt gtcataaatc   2520
tgttactttc ctacagagat atccaggacg tttatgattc tattgtgaag ctggtagaga   2580
ctttagaaaa actgccaacc tttgatttgg cctcccatca ccatgtgaag tttcattatg   2640
catttgcact gaataggaga aatctccctg gtgacagagc aaaagctctt gatattatga   2700
ttcccatggt gcaaagcgaa ggacaagttg cttcagatat gtattgccta gttggtcgaa   2760
tctacaaaga tatgtttttg gactctaatt tcacggacac tgaaagcaga gaccatggag   2820
cttcttggtt caaaaaggca tttgaatctg agccaacact acagtcagga attaattatg   2880
cggtcctcct cctggcagct ggacaccagt ttgaatcttc ctttgagctc cggaaagttg   2940
gggtgaagct aagtagtctt cttggtaaaa agggaaactt ggaaaaactc cagagctact   3000
gggaagttgg atttttttctg gggggccagcg tcctagccaa tgaccacatg agagtcattc   3060
aagcatctga aaagcttttt aaactgaaga caccagcatg gtacctcaag tctattgtag   3120
agacaatttt aatatataag cattttgtga aactgaccac agaacagcct gtggccaagc   3180
aagaacttgt ggacttttgg atggatttcc tggtcgaggc cacaaagaca gatgttactg   3240
tggttaggtt tccagtatta atattagaac caaccaaaat ctatcaacct tcttatttgt   3300
ctatcaacaa tgaagttgag gaaaagacaa tctctatttg gcacgtgctt cctgatgaca   3360
agaaaggtat acatgagtgg aattttagtg cctcttctgt caggggagtg agtatttcta   3420
aatttgaaga aagatgctgc tttctttatg tgcttcacaa ttctgatgat ttccaaatct   3480
atttctgtac agaacttcat tgtaaaaagt tttttgagat ggtgaacacc attaccgaag   3540
agaaggggag aagcacagag gaaggagact gtgaaagtga cttgctggag tatgactatg   3600
aatatgatga aaatggtgac agagtcgttt taggaaaagg cacttatggg atagtctacg   3660
caggtcggga cttgagcaac caagtcagaa ttgctattaa ggaaatccca gagagagaca   3720
gcagatactc tcagcccctg catgaagaaa tagcattgca taaacacctg aagcacaaaa   3780
atattgtcca gtatctgggc tctttcagtg agaatggttt cattaaaatc ttcatggagc   3840
aggtccctgg aggaagtctt tctgctctcc ttcgttccaa atggggtcca ttaaaagaca   3900
atgagcaaac aattggcttt tatacaaagc aaatactgga aggattaaaa tatctccatg   3960
acaatcagat agttcaccgg gacataaagg gtgacaatgt gttgattaat acctacagtg   4020
gtgttctcaa gatctctgac ttcggaacat caaagaggct tgctggcata aacccctgta   4080
ctgaaacttt tactggtacc ctccagtata tggcaccaga aataatagat aaaggaccaa   4140
gaggctacgg aaaagcagca gacatctggt ctctgggctg tacaatcatt gaaatggcca   4200
caggaaaacc cccattttat gaactgggag aaccacaagc agctatgttc aaggtgggaa   4260
tgtttaaagt ccaccctgag atcctctaga gcggccgcag gtacctgaat aactaaggcc   4320
gcttcccttt agtgagggtt aatgcttcga gcagacatga taagatacat tgatgagttt   4380
```

```
ggacaaacca caactagaat gcagtgaaaa aaatgcttta tttgtgaaat ttgtgatgct   4440
attgctttat ttgtaaccat tataagctgc aataaacaag ttaacaacaa caattgcatt   4500
cattttatgt ttcaggttca gggggagatg tgggaggttt tttaaagcaa gtaaaacctc   4560
tacaaatgtg gtaaaatccg ataaggatcg atccgggctg gcgtaatagc gaagaggccc   4620
gcaccgatcg cccttcccaa cagttgcgca gcctgaatgg cgaatggacg cgccctgtag   4680
cggcgcatta agcgcggcgg gtgtggtggt tacgcgcagc gtgaccgcta cacttgccag   4740
cgccctagcg cccgctcctt tcgctttctt cccttccttt cacgccacgt tcgccggctt   4800
tccccgtcaa gctctaaatc gggggctccc tttagggttc cgatttagtg ctttacggca   4860
cctcgacccc aaaaaacttg attagggtga tggttcacgt agtgggccat cgccctgata   4920
gacggttttt cgccctttga cgttggagtc cacgttcttt aatagtggac tcttgttcca   4980
aactggaaca acactcaacc ctatctcggt ctattctttt gatttataag ggattttgcc   5040
gatttcggcc tattggttaa aaaatgagct gatttaacaa aaatttaacg cgaattttaa   5100
caaaatatta acgcttacaa tttcctgatg cggtattttc tccttacgca tctgtgcggt   5160
atttcacacc gcatacgcgg atcttccgta ccttctgagg cggaaagaac cagctgtgga   5220
atgtgtgtca gttagggtgt ggaaagtccc caggctcccc agcaggcaga agtatgcaaa   5280
gcatgcatct caattagtca gcaaccaggt gtggaaagtc cccaggctcc ccagcaggca   5340
gaagtatgca aagcatgcat ctcaattagt cagcaaccat agtcccgccc ctaactccgc   5400
ccatcccgcc cctaactccg cccagttccg cccattctcc gccccatggc tgactaattt   5460
tttttattta tgcagaggcc gaggccgcct cggcctctga gctattccag aagtagtgag   5520
gaggcttttt tggaggccta ggcttttgca aaaagcttga ttcttctgac acaacagtct   5580
cgaacttaag gctagaattc tggctacagg taagcgcccc taaaatccct ttgggcacaa   5640
tgtgtcctga ggggagaggc agcgacctgt agatgggacg ggggcactaa ccctcaggtt   5700
tggggcttct gaatgtgagt atcgccatgt aagcccagta tttggccaat ctcagaaagc   5760
tcctggtccc tggagggatg gagagagaaa aacaaacagc tcctggagca gggagagtgc   5820
tggcctcttg ctctccggct ccctctgttg ccctctggtt tctccccagg ctcccggacg   5880
tcctctagcc accatgactt cgaaagttta tgatccagaa caaaggaaac ggatgataac   5940
tggtccgcag tggtgggcca gatgtaaaca aatgaatgtt cttgattcat ttattaatta   6000
ttatgattca gaaaaacatg cagaaaatgc tgttattttt ttacatggta acgcggcctc   6060
ttcttattta tggcgacatg ttgtgccaca tattgagcca gtagcgcggt gtattatacc   6120
agaccttatt ggtatgggca aatcaggcaa atctggtaat ggttcttata ggttacttga   6180
tcattacaaa tatcttactg catggtttga acttcttaat ttaccaaaga agatcatttt   6240
tgtcggccat gattggggtg cttgtttggc atttcattat agctatgagc atcaagataa   6300
gatcaaagca atagttcacg ctgaaagtgt agtagatgtg attgaatcat gggatgaatg   6360
gcctgatatt gaagaagata ttgcgttgat caaatctgaa gaaggagaaa aaatggtttt   6420
ggagaataac ttcttcgtgg aaaccatgtt gccatcaaaa atcatgagaa agttagaacc   6480
agaagaattt gcagcatatc ttgaaccatt caaagagaaa ggtgaagttc gtcgtccaac   6540
attatcatgg cctcgtgaaa tcccgttagt aaaaggtggt aaacctgacg ttgtacaaat   6600
tgttaggaat tataatgctt atctacgtgc aagtgatgat ttaccaaaaa tgtttattga   6660
atcggaccca ggattctttt ccaatgctat tgttgaaggt gccaagaagt ttcctaatac   6720
tgaatttgtc aaagtaaaag gtcttcattt ttcgcaagaa gatgcacctg atgaaatggg   6780
```

```
aaaatatatc aaatcgttcg ttgagcgagt tctcaaaaat gaacaataat tctagccctg   6840
aataagtgat aataagcgga tgaatggcag aaattcgtcg aagcgcaata aaatatcttt   6900
attttcatta catctgtgtg ttggtttttt gtgtgaatcg atagcgataa ggatcggaag   6960
atccgcgtat ggtgcactct cagtacaatc tgctctgatg ccgcatagtt aagccagccc   7020
cgacacccgc caacacccgc tgacgcgccc tgacgggctt gtctgctccc ggcatccgct   7080
tacagacaag ctgtgaccgt ctccgggagc tgcatgtgtc agaggttttc accgtcatca   7140
ccgaaacgcg cgagacgaaa gggcctcgtg atacgcctat ttttataggt taatgtcatg   7200
ataataatgg tttcttagac gtcaggtggc acttttcggg gaaatgtgcg cggaacccct   7260
atttgtttat ttttctaaat acattcaaat atgtatccgc tcatgagaca ataaccctga   7320
taaatgcttc aataatattg aaaaaggaag agtatgagta ttcaacattt ccgtgtcgcc   7380
cttattccct tttttgcggc attttgcctt cctgtttttg ctcacccaga aacgctggtg   7440
aaagtaaaag atgctgaaga tcagttgggt gcacgagtgg gttacatcga actggatctc   7500
aacagcggta agatccttga gagttttcgc cccgaagaac gttttccaat gatgagcact   7560
tttaaagttc tgctatgtgg cgcggtatta tcccgtgttg acgccgggca agagcaactc   7620
ggtcgccgca tacactattc tcagaatgac ttggttgagt actcaccagt cacagaaaag   7680
catcttacgg atggcatgac agtaagagaa ttatgcagtg ctgccataac catgagtgat   7740
aacactgcgg ccaacttact tctgacaacg atcggaggac cgaaggagct aaccgctttt   7800
ttgcacaaca tgggggatca tgtaactcgc cttgatcgtt gggaaccgga gctgaatgaa   7860
gccataccaa acgacgagcg tgacaccacg atgcctgtag caatggcaac aacgttgcgc   7920
aaactattaa ctggcgaact acttactcta gcttcccggc aacaattaat agactggatg   7980
gaggcggata aagttgcagg accacttctg cgctcggccc ttccggctgg ctggtttatt   8040
gctgataaat ctggagccgg tgagcgtggg tctcgcggta tcattgcagc actggggcca   8100
gatggtaagc cctcccgtat cgtagttatc tacacgacgg ggagtcaggc aactatggat   8160
gaacgaaata gacagatcgc tgagataggt gcctcactga ttaagcattg gtaactgtca   8220
gaccaagttt actcatatat actttagatt gatttaaaac ttcattttta atttaaaagg   8280
atctaggtga agatcctttt tgataatctc atgaccaaaa tcccttaacg tgagttttcg   8340
ttccactgag cgtcagaccc cgtagaaaag atcaaaggat cttcttgaga tccttttttt   8400
ctgcgcgtaa tctgctgctt gcaaacaaaa aaaccaccgc taccagcggt ggtttgtttg   8460
ccggatcaag agctaccaac tctttttccg aaggtaactg gcttcagcag agcgcagata   8520
ccaaatactg ttcttctagt gtagccgtag ttaggccacc acttcaagaa ctctgtagca   8580
ccgcctacat acctcgctct gctaatcctg ttaccagtgg ctgctgccag tggcgataag   8640
tcgtgtctta ccgggttgga ctcaagacga tagttaccgg ataaggcgca gcggtcgggc   8700
tgaacggggg gttcgtgcac acagcccagc ttggagcgaa cgacctacac cgaactgaga   8760
tacctacagc gtgagctatg agaaagcgcc acgcttcccg aagggagaaa ggcggacagg   8820
tatccggtaa gcggcagggt cggaacagga gagcgcacga gggagcttcc agggggaaac   8880
gcctggtatc tttatagtcc tgtcgggttt cgccacctct gacttgagcg tcgatttttg   8940
tgatgctcgt caggggggcg gagcctatgg aaaaacgcca gcaacgcggc ctttttacgg   9000
ttcctggcct tttgctggcc ttttgctcac atggctcgac agatct                  9046
```

<210> SEQ ID NO 21

<211> LENGTH: 1056
<212> TYPE: PRT
<213> ORGANISM: Artificial Sequence
<220> FEATURE:
<223> OTHER INFORMATION: Gal4 ASK1(i) fusion protein sequence

<400> SEQUENCE: 21

Met Lys Leu Leu Ser Ser Ile Glu Gln Ala Cys Asp Ile Cys Arg Leu
1 5 10 15

Lys Lys Leu Lys Cys Ser Lys Glu Lys Pro Lys Cys Ala Lys Cys Leu
20 25 30

Lys Asn Asn Trp Glu Cys Arg Tyr Ser Pro Lys Thr Lys Arg Ser Pro
35 40 45

Leu Thr Arg Ala His Leu Thr Glu Val Glu Ser Arg Leu Glu Arg Leu
50 55 60

Glu Gln Leu Phe Leu Leu Ile Phe Pro Arg Glu Asp Leu Asp Met Ile
65 70 75 80

Leu Lys Met Asp Ser Leu Gln Asp Ile Lys Ala Leu Leu Thr Gly Leu
85 90 95

Phe Val Gln Asp Asn Val Asn Lys Asp Ala Val Thr Asp Arg Leu Ala
100 105 110

Ser Val Glu Thr Asp Met Pro Leu Thr Leu Arg Gln His Arg Ile Ser
115 120 125

Ala Thr Ser Ser Ser Glu Glu Ser Ser Asn Lys Gly Gln Arg Gln Leu
130 135 140

Thr Val Ser Pro Glu Phe Pro Gly Ile Arg Thr Glu Ala Asp Glu Gly
145 150 155 160

Ile Thr Phe Ser Val Pro Pro Phe Ala Pro Ser Gly Phe Cys Thr Ile
165 170 175

Pro Glu Gly Gly Ile Cys Arg Arg Gly Gly Ala Ala Ala Val Gly Glu
180 185 190

Gly Glu Glu His Gln Leu Pro Pro Pro Pro Pro Gly Ser Phe Trp Asn
195 200 205

Val Glu Ser Ala Ala Ala Pro Gly Ile Gly Cys Pro Ala Ala Thr Ser
210 215 220

Ser Ser Ser Ala Thr Arg Gly Arg Gly Ser Ser Val Gly Gly Gly Ser
225 230 235 240

Arg Arg Thr Thr Val Ala Tyr Val Ile Asn Glu Ala Ser Gln Gly Gln
245 250 255

Leu Val Val Ala Glu Ser Glu Ala Leu Gln Ser Leu Arg Glu Ala Cys
260 265 270

Glu Thr Val Gly Ala Thr Leu Glu Thr Leu His Phe Gly Lys Leu Asp
275 280 285

Phe Gly Glu Thr Thr Val Leu Asp Arg Phe Tyr Asn Ala Asp Ile Ala
290 295 300

Val Val Glu Met Ser Asp Ala Phe Arg Gln Pro Ser Leu Phe Tyr His
305 310 315 320

Leu Gly Val Arg Glu Ser Phe Ser Met Ala Asn Asn Ile Ile Leu Tyr
325 330 335

Cys Asp Thr Asn Ser Asp Ser Leu Gln Ser Leu Lys Glu Ile Ile Cys
340 345 350

Gln Lys Asn Thr Met Cys Thr Gly Asn Tyr Thr Phe Val Pro Tyr Met
355 360 365

Ile Thr Pro His Asn Lys Val Tyr Cys Cys Asp Ser Ser Phe Met Lys
370 375 380

-continued

```
Gly Leu Thr Glu Leu Met Gln Pro Asn Phe Glu Leu Leu Leu Gly Pro
385                 390                 395                 400

Ile Cys Leu Pro Leu Val Asp Arg Phe Ile Gln Leu Leu Lys Val Ala
                405                 410                 415

Gln Ala Ser Ser Ser Gln Tyr Phe Arg Glu Ser Ile Leu Asn Asp Ile
            420                 425                 430

Arg Lys Ala Arg Asn Leu Tyr Thr Gly Lys Glu Leu Ala Ala Glu Leu
        435                 440                 445

Ala Arg Ile Arg Gln Arg Val Asp Asn Ile Glu Val Leu Thr Ala Asp
    450                 455                 460

Ile Val Ile Asn Leu Leu Leu Ser Tyr Arg Asp Ile Gln Asp Val Tyr
465                 470                 475                 480

Asp Ser Ile Val Lys Leu Val Glu Thr Leu Glu Lys Leu Pro Thr Phe
                485                 490                 495

Asp Leu Ala Ser His His His Val Lys Phe His Tyr Ala Phe Ala Leu
            500                 505                 510

Asn Arg Arg Asn Leu Pro Gly Asp Arg Ala Lys Ala Leu Asp Ile Met
        515                 520                 525

Ile Pro Met Val Gln Ser Glu Gly Gln Val Ala Ser Asp Met Tyr Cys
    530                 535                 540

Leu Val Gly Arg Ile Tyr Lys Asp Met Phe Leu Asp Ser Asn Phe Thr
545                 550                 555                 560

Asp Thr Glu Ser Arg Asp His Gly Ala Ser Trp Phe Lys Lys Ala Phe
                565                 570                 575

Glu Ser Glu Pro Thr Leu Gln Ser Gly Ile Asn Tyr Ala Val Leu Leu
            580                 585                 590

Leu Ala Ala Gly His Gln Phe Glu Ser Ser Phe Glu Leu Arg Lys Val
        595                 600                 605

Gly Val Lys Leu Ser Ser Leu Leu Gly Lys Lys Gly Asn Leu Glu Lys
    610                 615                 620

Leu Gln Ser Tyr Trp Glu Val Gly Phe Phe Leu Gly Ala Ser Val Leu
625                 630                 635                 640

Ala Asn Asp His Met Arg Val Ile Gln Ala Ser Glu Lys Leu Phe Lys
                645                 650                 655

Leu Lys Thr Pro Ala Trp Tyr Leu Lys Ser Ile Val Glu Thr Ile Leu
            660                 665                 670

Ile Tyr Lys His Phe Val Lys Leu Thr Thr Glu Gln Pro Val Ala Lys
        675                 680                 685

Gln Glu Leu Val Asp Phe Trp Met Asp Phe Leu Val Glu Ala Thr Lys
    690                 695                 700

Thr Asp Val Thr Val Val Arg Phe Pro Val Leu Ile Leu Glu Pro Thr
705                 710                 715                 720

Lys Ile Tyr Gln Pro Ser Tyr Leu Ser Ile Asn Asn Glu Val Glu Glu
                725                 730                 735

Lys Thr Ile Ser Ile Trp His Val Leu Pro Asp Asp Lys Lys Gly Ile
            740                 745                 750

His Glu Trp Asn Phe Ser Ala Ser Ser Val Arg Gly Val Ser Ile Ser
        755                 760                 765

Lys Phe Glu Glu Arg Cys Cys Phe Leu Tyr Val Leu His Asn Ser Asp
    770                 775                 780

Asp Phe Gln Ile Tyr Phe Cys Thr Glu Leu His Cys Lys Lys Phe Phe
785                 790                 795                 800
```

-continued

```
Glu Met Val Asn Thr Ile Thr Glu Glu Lys Gly Arg Ser Thr Glu Glu
                805                 810                 815

Gly Asp Cys Glu Ser Asp Leu Leu Glu Tyr Asp Tyr Glu Tyr Asp Glu
            820                 825                 830

Asn Gly Asp Arg Val Val Leu Gly Lys Gly Thr Tyr Gly Ile Val Tyr
        835                 840                 845

Ala Gly Arg Asp Leu Ser Asn Gln Val Arg Ile Ala Ile Lys Glu Ile
    850                 855                 860

Pro Glu Arg Asp Ser Arg Tyr Ser Gln Pro Leu His Glu Glu Ile Ala
865                 870                 875                 880

Leu His Lys His Leu Lys His Lys Asn Ile Val Gln Tyr Leu Gly Ser
                885                 890                 895

Phe Ser Glu Asn Gly Phe Ile Lys Ile Phe Met Glu Gln Val Pro Gly
            900                 905                 910

Gly Ser Leu Ser Ala Leu Leu Arg Ser Lys Trp Gly Pro Leu Lys Asp
        915                 920                 925

Asn Glu Gln Thr Ile Gly Phe Tyr Thr Lys Gln Ile Leu Glu Gly Leu
    930                 935                 940

Lys Tyr Leu His Asp Asn Gln Ile Val His Arg Asp Ile Lys Gly Asp
945                 950                 955                 960

Asn Val Leu Ile Asn Thr Tyr Ser Gly Val Leu Lys Ile Ser Asp Phe
                965                 970                 975

Gly Thr Ser Lys Arg Leu Ala Gly Ile Asn Pro Cys Thr Glu Thr Phe
            980                 985                 990

Thr Gly Thr Leu Gln Tyr Met Ala  Pro Glu Ile Ile Asp  Lys Gly Pro
        995                 1000                 1005

Arg Gly  Tyr Gly Lys Ala Ala  Asp Ile Trp Ser Leu  Gly Cys Thr
    1010                 1015                 1020

Ile Ile  Glu Met Ala Thr Gly  Lys Pro Pro Phe Tyr  Glu Leu Gly
    1025                 1030                 1035

Glu Pro  Gln Ala Ala Met Phe  Lys Val Gly Met Phe  Lys Val His
    1040                 1045                 1050

Pro Glu  Ile
    1055


<210> SEQ ID NO 22
<211> LENGTH: 8104
<212> TYPE: DNA
<213> ORGANISM: Artificial Sequence
<220> FEATURE:
<223> OTHER INFORMATION: construct sequence containing ASK1(j) cloned in
      pBIND

<400> SEQUENCE: 22

tcaatattgg ccattagcca tattattcat tggttatata gcataaatca atattggcta     60

ttggccattg catacgttgt atctatatca taatatgtac atttatattg gctcatgtcc    120

aatatgaccg ccatgttggc attgattatt gactagttat taatagtaat caattacggg    180

gtcattagtt catagcccat atatggagtt ccgcgttaca taacttacgg taaatggccc    240

gcctggctga ccgcccaacg acccccgccc attgacgtca ataatgacgt atgttcccat    300

agtaacgcca atagggactt tccattgacg tcaatgggtg gagtatttac ggtaaactgc    360

ccacttggca gtacatcaag tgtatcatat gccaagtccg ccccctattg acgtcaatga    420

cggtaaatgg cccgcctggc attatgccca gtacatgacc ttacgggact ttcctacttg    480

gcagtacatc tacgtattag tcatcgctat taccatggtg atgcggtttt ggcagtacac    540
```

-continued

```
caatgggcgt ggatagcggt ttgactcacg gggatttcca agtctccacc ccattgacgt    600
caatgggagt ttgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaggctag agtacttaat acgactcact   1080
ataggctagc cagcttgaag caagcctcct gaaagatgaa gctactgtct tctatcgaac   1140
aagcatgcga tatttgccga cttaaaaagc tcaagtgctc caaagaaaaa ccgaagtgcg   1200
ccaagtgtct gaagaacaac tgggagtgtc gctactctcc caaaaccaaa aggtctccgc   1260
tgactagggc acatctgaca gaagtggaat caaggctaga aagactggaa cagctatttc   1320
tactgatttt tcctcgagaa gaccttgaca tgattttgaa aatggattct ttacaggata   1380
taaaagcatt gttaacagga ttatttgtac aagataatgt gaataaagat gccgtcacag   1440
atagattggc ttcagtggag actgatatgc ctctaacatt gagacagcat agaataagtg   1500
cgacatcatc atcggaagag agtagtaaca aaggtcaaag acagttgact gtatcgccgg   1560
aattcccggg gatccggatc cgtctttcct acagagatat ccaggacgtt tatgattcta   1620
ttgtgaagct ggtagagact ttagaaaaac tgccaacctt tgatttggcc tcccatcacc   1680
atgtgaagtt tcattatgca tttgcactga ataggagaaa tctccctggt gacagagcaa   1740
aagctcttga tattatgatt cccatggtgc aaagcgaagg acaagttgct tcagatatgt   1800
attgcctagt tggtcgaatc tacaaagata tgtttttgga ctctaatttc acggacactg   1860
aaagcagaga ccatggagct tcttggttca aaaaggcatt tgaatctgag ccaacactac   1920
agtcaggaat taattatgcg gtcctcctcc tggcagctgg acaccagttt gaatcttcct   1980
ttgagctccg gaaagttggg gtgaagctaa gtagtcttct tggtaaaaag ggaaacttgg   2040
aaaaactcca gagctactgg gaagttggat tttttctggg ggccagcgtc ctagccaatg   2100
accacatgag agtcattcaa gcatctgaaa agcttttaa actgaagaca ccagcatggt    2160
acctcaagtc tattgtagag acaattttaa tatataagca ttttgtgaaa ctgaccacag   2220
aacagcctgt ggccaagcaa gaacttgtgg acttttggat ggatttcctg gtcgaggcca   2280
caaagacaga tgttactgtg gttaggtttc cagtattaat attagaacca accaaaatct   2340
atcaaccttc ttatttgtct atcaacaatg aagttgagga aaagacaatc tctatttggc   2400
acgtgcttcc tgatgacaag aaaggtatac atgagtggaa ttttagtgcc tcttctgtca   2460
ggggagtgag tatttctaaa tttgaagaaa gatgctgctt tctttatgtg cttcacaatt   2520
ctgatgattt ccaaatctat ttctgtacag aacttcattg taaaaagttt tttgagatgg   2580
tgaacaccat taccgaagag aaggggagaa gcacagagga aggagactgt gaaagtgact   2640
tgctggagta tgactatgaa tatgatgaaa atggtgacag agtcgtttta ggaaaaggca   2700
cttatgggat agtctacgca ggtcgggact tgagcaacca agtcagaatt gctattaagg   2760
aaatcccaga gagagacagc agatactctc agcccctgca tgaagaaata gcattgcata   2820
aacacctgaa gcacaaaaat attgtccagt atctgggctc tttcagtgag aatggtttca   2880
```

-continued

```
ttaaaatctt catggagcag gtccctggag gaagtctttc tgctctcctt cgttccaaat   2940
ggggtccatt aaaagacaat gagcaaacaa ttggctttta tacaaagcaa atactggaag   3000
gattaaaata tctccatgac aatcagatag ttcaccggga cataaagggt gacaatgtgt   3060
tgattaatac ctacagtggt gttctcaaga tctctgactt cggaacatca aagaggcttg   3120
ctggcataaa cccctgtact gaaactttta ctggtaccct ccagtatatg gcaccagaaa   3180
taatagataa aggaccaaga ggctacggaa aagcagcaga catctggtct ctgggctgta   3240
caatcattga aatggccaca ggaaaacccc cattttatga actgggagaa ccacaagcag   3300
ctatgttcaa ggtgggaatg tttaaagtcc accctgagat cctctagagc ggccgcaggt   3360
acctgaataa ctaaggccgc ttccctttag tgagggttaa tgcttcgagc agacatgata   3420
agatacattg atgagtttgg acaaaccaca actagaatgc agtgaaaaaa atgctttatt   3480
tgtgaaattt gtgatgctat tgctttattt gtaaccatta taagctgcaa taaacaagtt   3540
aacaacaaca attgcattca ttttatgttt caggttcagg gggagatgtg ggaggttttt   3600
taaagcaagt aaaacctcta caaatgtggt aaaatccgat aaggatcgat ccgggctggc   3660
gtaatagcga agaggcccgc accgatcgcc cttcccaaca gttgcgcagc ctgaatggcg   3720
aatggacgcg ccctgtagcg gcgcattaag cgcggcgggt gtggtggtta cgcgcagcgt   3780
gaccgctaca cttgccagcg ccctagcgcc cgctcctttc gctttcttcc cttcctttca   3840
cgccacgttc gccggctttc cccgtcaagc tctaaatcgg gggctccctt tagggttccg   3900
atttagtgct ttacggcacc tcgaccccaa aaaacttgat tagggtgatg gttcacgtag   3960
tgggccatcg ccctgataga cggtttttcg ccctttgacg ttggagtcca cgttctttaa   4020
tagtggactc ttgttccaaa ctggaacaac actcaaccct atctcggtct attcttttga   4080
tttataaggg attttgccga tttcggccta ttggttaaaa aatgagctga tttaacaaaa   4140
atttaacgcg aattttaaca aaatattaac gcttacaatt tcctgatgcg gtattttctc   4200
cttacgcatc tgtgcggtat ttcacaccgc atacgcggat cttccgtacc ttctgaggcg   4260
gaaagaacca gctgtggaat gtgtgtcagt tagggtgtgg aaagtcccca ggctccccag   4320
caggcagaag tatgcaaagc atgcatctca attagtcagc aaccaggtgt ggaaagtccc   4380
caggctcccc agcaggcaga agtatgcaaa gcatgcatct caattagtca gcaaccatag   4440
tcccgcccct aactccgccc atcccgcccc taactccgcc cagttccgcc cattctccgc   4500
cccatggctg actaattttt tttatttatg cagaggccga ggccgcctcg gcctctgagc   4560
tattccagaa gtagtgagga ggcttttttg gaggcctagg cttttgcaaa aagcttgatt   4620
cttctgacac aacagtctcg aacttaaggc tagaattctg gctacaggta agcgccccta   4680
aaatcccttt gggcacaatg tgtcctgagg ggagaggcag cgacctgtag atgggacggg   4740
ggcactaacc ctcaggtttg gggcttctga atgtgagtat cgccatgtaa gcccagtatt   4800
tggccaatct cagaaagctc ctggtccctg gagggatgga gagagaaaaa caaacagctc   4860
ctggagcagg gagagtgctg gcctcttgct ctccggctcc ctctgttgcc ctctggtttc   4920
tccccaggct cccggacgtc cctagccac catgacttcg aaagtttatg atccagaaca   4980
aaggaaacgg atgataactg gtccgcagtg gtgggccaga tgtaaacaaa tgaatgttct   5040
tgattcattt attaattatt atgattcaga aaaacatgca gaaaatgctg ttattttttt   5100
acatggtaac gcggcctctt cttatttatg gcgacatgtt gtgccacata ttgagccagt   5160
agcgcggtgt attataccag accttattgg tatgggcaaa tcaggcaaat ctggtaatgg   5220
ttcttatagg ttacttgatc attacaaata tcttactgca tggtttgaac ttcttaattt   5280
```

accaaagaag atcatttttg tcggccatga ttggggtgct tgtttggcat ttcattatag 5340
ctatgagcat caagataaga tcaaagcaat agttcacgct gaaagtgtag tagatgtgat 5400
tgaatcatgg gatgaatggc ctgatattga agaagatatt gcgttgatca aatctgaaga 5460
aggagaaaaa atggttttgg agaataactt cttcgtggaa accatgttgc catcaaaaat 5520
catgagaaag ttagaaccag aagaatttgc agcatatctt gaaccattca aagagaaagg 5580
tgaagttcgt cgtccaacat tatcatggcc tcgtgaaatc ccgttagtaa aaggtggtaa 5640
acctgacgtt gtacaaattg ttaggaatta taatgcttat ctacgtgcaa gtgatgattt 5700
accaaaaatg tttattgaat cggacccagg attcttttcc aatgctattg ttgaaggtgc 5760
caagaagttt cctaatactg aatttgtcaa agtaaaaggt cttcattttt cgcaagaaga 5820
tgcacctgat gaaatgggaa aatatatcaa atcgttcgtt gagcgagttc tcaaaaatga 5880
acaataattc tagccctgaa taagtgataa taagcggatg aatggcagaa attcgtcgaa 5940
gcgcaataaa atatctttat tttcattaca tctgtgtgtt ggttttttgt gtgaatcgat 6000
agcgataagg atcggaagat ccgcgtatgg tgcactctca gtacaatctg ctctgatgcc 6060
gcatagttaa gccagccccg acacccgcca acacccgctg acgcgccctg acgggcttgt 6120
ctgctcccgg catccgctta cagacaagct gtgaccgtct ccgggagctg catgtgtcag 6180
aggttttcac cgtcatcacc gaaacgcgcg agacgaaagg gcctcgtgat acgcctattt 6240
ttataggtta atgtcatgat aataatggtt tcttagacgt caggtggcac ttttcgggga 6300
aatgtgcgcg gaacccctat ttgtttattt ttctaaatac attcaaatat gtatccgctc 6360
atgagacaat aaccctgata aatgcttcaa taatattgaa aaaggaagag tatgagtatt 6420
caacatttcc gtgtcgccct tattcccttt tttgcggcat tttgccttcc tgtttttgct 6480
cacccagaaa cgctggtgaa agtaaaagat gctgaagatc agttgggtgc acgagtgggt 6540
tacatcgaac tggatctcaa cagcggtaag atccttgaga gttttcgccc cgaagaacgt 6600
tttccaatga tgagcacttt taaagttctg ctatgtggcg cggtattatc ccgtgttgac 6660
gccgggcaag agcaactcgg tcgccgcata cactattctc agaatgactt ggttgagtac 6720
tcaccagtca cagaaaagca tcttacggat ggcatgacag taagagaatt atgcagtgct 6780
gccataacca tgagtgataa cactgcggcc aacttacttc tgacaacgat cggaggaccg 6840
aaggagctaa ccgctttttt gcacaacatg ggggatcatg taactcgcct tgatcgttgg 6900
gaaccggagc tgaatgaagc cataccaaac gacgagcgtg acaccacgat gcctgtagca 6960
atggcaacaa cgttgcgcaa actattaact ggcgaactac ttactctagc ttcccggcaa 7020
caattaatag actggatgga ggcggataaa gttgcaggac cacttctgcg ctcggccctt 7080
ccggctggct ggtttattgc tgataaatct ggagccggtg agcgtgggtc tcgcggtatc 7140
attgcagcac tggggccaga tggtaagccc tcccgtatcg tagttatcta cacgacgggg 7200
agtcaggcaa ctatggatga acgaaataga cagatcgctg agataggtgc ctcactgatt 7260
aagcattggt aactgtcaga ccaagtttac tcatatatac tttagattga tttaaaactt 7320
catttttaat ttaaaaggat ctaggtgaag atcctttttg ataatctcat gaccaaaatc 7380
ccttaacgtg agttttcgtt ccactgagcg tcagaccccg tagaaaagat caaaggatct 7440
tcttgagatc cttttttttct gcgcgtaatc tgctgcttgc aaacaaaaaa accaccgcta 7500
ccagcggtgg tttgtttgcc ggatcaagag ctaccaactc tttttccgaa ggtaactggc 7560
ttcagcagag cgcagatacc aaatactgtt cttctagtgt agccgtagtt aggccaccac 7620

```
ttcaagaact ctgtagcacc gcctacatac ctcgctctgc taatcctgtt accagtggct   7680

gctgccagtg gcgataagtc gtgtcttacc gggttggact caagacgata gttaccggat   7740

aaggcgcagc ggtcgggctg aacggggggt tcgtgcacac agcccagctt ggagcgaacg   7800

acctacaccg aactgagata cctacagcgt gagctatgag aaagcgccac gcttcccgaa   7860

gggagaaagg cggacaggta tccggtaagc ggcagggtcg gaacaggaga gcgcacgagg   7920

gagcttccag ggggaaacgc ctggtatctt tatagtcctg tcgggtttcg ccacctctga   7980

cttgagcgtc gatttttgtg atgctcgtca ggggggcgga gcctatggaa aaacgccagc   8040

aacgcggcct ttttacggtt cctggccttt tgctggcctt ttgctcacat ggctcgacag   8100

atct                                                                8104
```

```
<210> SEQ ID NO 23
<211> LENGTH: 742
<212> TYPE: PRT
<213> ORGANISM: Artificial Sequence
<220> FEATURE:
<223> OTHER INFORMATION: Gal4 ASK1(j) fusion protein sequence

<400> SEQUENCE: 23

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Pro Glu Phe Pro Gly Ile Arg Ile Arg Leu Ser Tyr Arg
145                 150                 155                 160

Asp Ile Gln Asp Val Tyr Asp Ser Ile Val Lys Leu Val Glu Thr Leu
                165                 170                 175

Glu Lys Leu Pro Thr Phe Asp Leu Ala Ser His His His Val Lys Phe
            180                 185                 190

His Tyr Ala Phe Ala Leu Asn Arg Arg Asn Leu Pro Gly Asp Arg Ala
        195                 200                 205

Lys Ala Leu Asp Ile Met Ile Pro Met Val Gln Ser Glu Gly Gln Val
    210                 215                 220

Ala Ser Asp Met Tyr Cys Leu Val Gly Arg Ile Tyr Lys Asp Met Phe
225                 230                 235                 240

Leu Asp Ser Asn Phe Thr Asp Thr Glu Ser Arg Asp His Gly Ala Ser
                245                 250                 255

Trp Phe Lys Lys Ala Phe Glu Ser Glu Pro Thr Leu Gln Ser Gly Ile
            260                 265                 270
```

-continued

```
Asn Tyr Ala Val Leu Leu Leu Ala Ala Gly His Gln Phe Glu Ser Ser
        275                 280                 285

Phe Glu Leu Arg Lys Val Gly Val Lys Leu Ser Ser Leu Leu Gly Lys
    290                 295                 300

Lys Gly Asn Leu Glu Lys Leu Gln Ser Tyr Trp Glu Val Gly Phe Phe
305                 310                 315                 320

Leu Gly Ala Ser Val Leu Ala Asn Asp His Met Arg Val Ile Gln Ala
                325                 330                 335

Ser Glu Lys Leu Phe Lys Leu Lys Thr Pro Ala Trp Tyr Leu Lys Ser
            340                 345                 350

Ile Val Glu Thr Ile Leu Ile Tyr Lys His Phe Val Lys Leu Thr Thr
        355                 360                 365

Glu Gln Pro Val Ala Lys Gln Glu Leu Val Asp Phe Trp Met Asp Phe
    370                 375                 380

Leu Val Glu Ala Thr Lys Thr Asp Val Thr Val Val Arg Phe Pro Val
385                 390                 395                 400

Leu Ile Leu Glu Pro Thr Lys Ile Tyr Gln Pro Ser Tyr Leu Ser Ile
                405                 410                 415

Asn Asn Glu Val Glu Glu Lys Thr Ile Ser Ile Trp His Val Leu Pro
            420                 425                 430

Asp Asp Lys Lys Gly Ile His Glu Trp Asn Phe Ser Ala Ser Ser Val
        435                 440                 445

Arg Gly Val Ser Ile Ser Lys Phe Glu Glu Arg Cys Cys Phe Leu Tyr
    450                 455                 460

Val Leu His Asn Ser Asp Asp Phe Gln Ile Tyr Phe Cys Thr Glu Leu
465                 470                 475                 480

His Cys Lys Lys Phe Phe Glu Met Val Asn Thr Ile Thr Glu Glu Lys
                485                 490                 495

Gly Arg Ser Thr Glu Glu Gly Asp Cys Glu Ser Asp Leu Leu Glu Tyr
            500                 505                 510

Asp Tyr Glu Tyr Asp Glu Asn Gly Asp Arg Val Val Leu Gly Lys Gly
        515                 520                 525

Thr Tyr Gly Ile Val Tyr Ala Gly Arg Asp Leu Ser Asn Gln Val Arg
    530                 535                 540

Ile Ala Ile Lys Glu Ile Pro Glu Arg Asp Ser Arg Tyr Ser Gln Pro
545                 550                 555                 560

Leu His Glu Glu Ile Ala Leu His Lys His Leu Lys His Lys Asn Ile
                565                 570                 575

Val Gln Tyr Leu Gly Ser Phe Ser Glu Asn Gly Phe Ile Lys Ile Phe
            580                 585                 590

Met Glu Gln Val Pro Gly Gly Ser Leu Ser Ala Leu Leu Arg Ser Lys
        595                 600                 605

Trp Gly Pro Leu Lys Asp Asn Glu Gln Thr Ile Gly Phe Tyr Thr Lys
    610                 615                 620

Gln Ile Leu Glu Gly Leu Lys Tyr Leu His Asp Asn Gln Ile Val His
625                 630                 635                 640

Arg Asp Ile Lys Gly Asp Asn Val Leu Ile Asn Thr Tyr Ser Gly Val
                645                 650                 655

Leu Lys Ile Ser Asp Phe Gly Thr Ser Lys Arg Leu Ala Gly Ile Asn
            660                 665                 670

Pro Cys Thr Glu Thr Phe Thr Gly Thr Leu Gln Tyr Met Ala Pro Glu
        675                 680                 685

Ile Ile Asp Lys Gly Pro Arg Gly Tyr Gly Lys Ala Ala Asp Ile Trp
```

-continued

```
    690                 695                 700

Ser Leu Gly Cys Thr Ile Ile Glu Met Ala Thr Gly Lys Pro Pro Phe
705                 710                 715                 720

Tyr Glu Leu Gly Glu Pro Gln Ala Ala Met Phe Lys Val Gly Met Phe
                725                 730                 735

Lys Val His Pro Glu Ile
            740


<210> SEQ ID NO 24
<211> LENGTH: 4733
<212> TYPE: DNA
<213> ORGANISM: Artificial Sequence
<220> FEATURE:
<223> OTHER INFORMATION: pEYFP-N1 Sequence

<400> SEQUENCE: 24

tagttattaa tagtaatcaa ttacggggtc attagttcat agcccatata tggagttccg      60

cgttacataa cttacggtaa atggcccgcc tggctgaccg cccaacgacc cccgcccatt     120

gacgtcaata atgacgtatg ttcccatagt aacgccaata gggactttcc attgacgtca     180

atgggtggag tatttacggt aaactgccca cttggcagta catcaagtgt atcatatgcc     240

aagtacgccc cctattgacg tcaatgacgg taaatggccc gcctggcatt atgcccagta     300

catgacctta tgggactttc ctacttggca gtacatctac gtattagtca tcgctattac     360

catggtgatg cggttttggc agtacatcaa tgggcgtgga tagcggtttg actcacgggg     420

atttccaagt ctccacccca ttgacgtcaa tgggagtttg ttttggcacc aaaatcaacg     480

ggactttcca aaatgtcgta acaactccgc cccattgacg caaatgggcg gtaggcgtgt     540

acggtgggag gtctatataa gcagagctgg tttagtgaac cgtcagatcc gctagcgcta     600

ccggactcag atctcgagct caagcttcga attctgcagt cgacggtacc gcgggcccgg     660

gatccaccgg tcgccaccat ggtgagcaag ggcgaggagc tgttcaccgg ggtggtgccc     720

atcctggtcg agctggacgg cgacgtaaac ggccacaagt tcagcgtgtc cggcgagggc     780

gagggcgatg ccacctacgg caagctgacc ctgaagttca tctgcaccac cggcaagctg     840

cccgtgccct ggcccaccct cgtgaccacc ttcggctacg gcctgcagtg cttcgcccgc     900

taccccgacc acatgaagca gcacgacttc ttcaagtccg ccatgcccga aggctacgtc     960

caggagcgca ccatcttctt caaggacgac ggcaactaca agacccgcgc cgaggtgaag    1020

ttcgagggcg acaccctggt gaaccgcatc gagctgaagg gcatcgactt caaggaggac    1080

ggcaacatcc tggggcacaa gctggagtac aactacaaca gccacaacgt ctatatcatg    1140

gccgacaagc agaagaacgg catcaaggtg aacttcaaga tccgccacaa catcgaggac    1200

ggcagcgtgc agctcgccga ccactaccag cagaacaccc ccatcggcga cggccccgtg    1260

ctgctgcccg acaaccacta cctgagctac cagtccgccc tgagcaaaga ccccaacgag    1320

aagcgcgatc acatggtcct gctggagttc gtgaccgccg ccgggatcac tctcggcatg    1380

gacgagctgt acaagtaaag cggccgcgac tctagatcat aatcagccat accacatttg    1440

tagaggtttt acttgcttta aaaaacctcc cacacctccc cctgaacctg aaacataaaa    1500

tgaatgcaat tgttgttgtt aacttgttta ttgcagctta taatggttac aaataaagca    1560

atagcatcac aaatttcaca aataaagcat ttttttcact gcattctagt tgtggtttgt    1620

ccaaactcat caatgtatct taaggcgtaa attgtaagcg ttaatatttt gttaaaattc    1680

gcgttaaatt tttgttaaat cagctcattt tttaaccaat aggccgaaat cggcaaaatc    1740
```

-continued

```
ccttataaat caaaagaata gaccgagata gggttgagtg ttgttccagt ttggaacaag   1800
agtccactat taaagaacgt ggactccaac gtcaaagggc gaaaaaccgt ctatcagggc   1860
gatggcccac tacgtgaacc atcaccctaa tcaagttttt tggggtcgag gtgccgtaaa   1920
gcactaaatc ggaaccctaa agggagcccc cgatttagag cttgacgggg aaagccggcg   1980
aacgtggcga gaaaggaagg gaagaaagcg aaaggagcgg gcgctagggc gctggcaagt   2040
gtagcggtca cgctgcgcgt aaccaccaca cccgccgcgc ttaatgcgcc gctacagggc   2100
gcgtcaggtg gcacttttcg gggaaatgtg cgcggaaccc ctatttgttt atttttctaa   2160
atacattcaa atatgtatcc gctcatgaga caataaccct gataaatgct tcaataatat   2220
tgaaaaagga agagtcctga ggcggaaaga accagctgtg gaatgtgtgt cagttagggt   2280
gtggaaagtc cccaggctcc ccagcaggca gaagtatgca aagcatgcat ctcaattagt   2340
cagcaaccag gtgtggaaag tccccaggct ccccagcagg cagaagtatg caaagcatgc   2400
atctcaatta gtcagcaacc atagtcccgc ccctaactcc gcccatcccg cccctaactc   2460
cgcccagttc cgcccattct ccgccccatg gctgactaat tttttttatt tatgcagagg   2520
ccgaggccgc ctcggcctct gagctattcc agaagtagtg aggaggcttt tttggaggcc   2580
taggcttttg caaagatcga tcaagagaca ggatgaggat cgtttcgcat gattgaacaa   2640
gatggattgc acgcaggttc tccggccgct tgggtggaga ggctattcgg ctatgactgg   2700
gcacaacaga caatcggctg ctctgatgcc gccgtgttcc ggctgtcagc gcaggggcgc   2760
ccggttcttt ttgtcaagac cgacctgtcc ggtgccctga atgaactgca agacgaggca   2820
gcgcggctat cgtggctggc cacgacgggc gttccttgcg cagctgtgct cgacgttgtc   2880
actgaagcgg gaagggactg gctgctattg ggcgaagtgc cggggcagga tctcctgtca   2940
tctcaccttg ctcctgccga gaaagtatcc atcatggctg atgcaatgcg gcggctgcat   3000
acgcttgatc cggctacctg cccattcgac caccaagcga aacatcgcat cgagcgagca   3060
cgtactcgga tggaagccgg tcttgtcgat caggatgatc tggacgaaga gcatcagggg   3120
ctcgcgccag ccgaactgtt cgccaggctc aaggcgagca tgcccgacgg cgaggatctc   3180
gtcgtgaccc atggcgatgc ctgcttgccg aatatcatgg tggaaaatgg ccgcttttct   3240
ggattcatcg actgtggccg gctgggtgtg gcggaccgct atcaggacat agcgttggct   3300
acccgtgata ttgctgaaga gcttggcggc gaatgggctg accgcttcct cgtgctttac   3360
ggtatcgccg ctcccgattc gcagcgcatc gccttctatc gccttcttga cgagttcttc   3420
tgagcgggac tctggggttc gaaatgaccg accaagcgac gcccaacctg ccatcacgag   3480
atttcgattc caccgccgcc ttctatgaaa ggttgggctt cggaatcgtt ttccgggacg   3540
ccggctggat gatcctccag cgcggggatc tcatgctgga gttcttcgcc caccctaggg   3600
ggaggctaac tgaaacacgg aaggagacaa taccggaagg aacccgcgct atgacggcaa   3660
taaaaagaca gaataaaacg cacggtgttg ggtcgtttgt tcataaacgc ggggttcggt   3720
cccagggctg gcactctgtc gataccccac cgagacccca ttggggccaa tacgcccgcg   3780
tttcttcctt ttccccaccc caccccccaa gttcgggtga aggcccaggg ctcgcagcca   3840
acgtcggggc ggcaggccct gccatagcct caggttactc atatatactt tagattgatt   3900
taaaacttca tttttaattt aaaaggatct aggtgaagat cctttttgat aatctcatga   3960
ccaaaatccc ttaacgtgag ttttcgttcc actgagcgtc agaccccgta gaaaagatca   4020
aaggatcttc ttgagatcct ttttttctgc gcgtaatctg ctgcttgcaa acaaaaaaac   4080
caccgctacc agcggtggtt tgtttgccgg atcaagagct accaactctt tttccgaagg   4140
```

```
taactggctt cagcagagcg cagataccaa atactgtcct tctagtgtag ccgtagttag   4200
gccaccactt caagaactct gtagcaccgc ctacatacct cgctctgcta atcctgttac   4260
cagtggctgc tgccagtggc gataagtcgt gtcttaccgg gttggactca agacgatagt   4320
taccggataa ggcgcagcgg tcgggctgaa cggggggttc gtgcacacag cccagcttgg   4380
agcgaacgac ctacaccgaa ctgagatacc tacagcgtga gctatgagaa agcgccacgc   4440
ttcccgaagg gagaaaggcg gacaggtatc cggtaagcgg cagggtcgga acaggagagc   4500
gcacgaggga gcttccaggg ggaaacgcct ggtatcttta tagtcctgtc gggtttcgcc   4560
acctctgact tgagcgtcga tttttgtgat gctcgtcagg ggggcggagc ctatggaaaa   4620
acgccagcaa cgcggccttt ttacggttcc tggccttttg ctggcctttt gctcacatgt   4680
tctttcctgc gttatcccct gattctgtgg ataaccgtat taccgccatg cat          4733
```

<210> SEQ ID NO 25
<211> LENGTH: 5345
<212> TYPE: DNA
<213> ORGANISM: Artificial Sequence
<220> FEATURE:
<223> OTHER INFORMATION: HIV-1 Nef Sequence cloned in pEYFP N1

<400> SEQUENCE: 25

```
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatcc gctagcgcta    600
ccggactcag atctcgagct caagcttatg gggggcaagt ggtcaaaaag cagtatagtt    660
ggatggcctg cagtgagaga aagaataaga agaactgagc cagcagcaga gggagtagga    720
gcagcgtctc gagacttaga taaacatgga gcacttacaa gcagcaacac agcccaaact    780
aatgctgatt gtgcctggct ggaagcacaa gaggaggaaa acgaagtagg gtttccagtc    840
agacctcagg tgccgctcag accaatgact tataaggggg cagtagatct cagcttcttt    900
ttaaaagaaa aggggggact ggaagggtta acttactcta agaaaagaca agaaatcctt    960
gatttgtggg tctatcacac acaaggctac ttccctgatt ggcaatgcta cacaccggga   1020
ccaggggtca gatacccact gacttttgga tggtgcttca agctagtgcc agttgaccca   1080
gatgaagtag gagaagccaa caatggagag aataactgtt tgctacaccc tataagcctg   1140
catggaatgg aggatccaga aagagaagta ttaaggtgga agtttgacag tcacctagca   1200
cacacacaca aggcccgcga gctacatccg gagtattaca aagactgcgc gtcgacggta   1260
ccgcgggccc gggatccacc ggtcgccacc atggtgagca agggcgagga gctgttcacc   1320
ggggtggtgc ccatcctggt cgagctggac ggcgacgtaa acggccacaa gttcagcgtg   1380
tccggcgagg gcgagggcga tgccacctac ggcaagctga ccctgaagtt catctgcacc   1440
```

accggcaagc tgcccgtgcc ctggcccacc ctcgtgacca ccttcggcta cggcctgcag 1500
tgcttcgccc gctaccccga ccacatgaag cagcacgact tcttcaagtc cgccatgccc 1560
gaaggctacg tccaggagcg caccatcttc ttcaaggacg acggcaacta caagacccgc 1620
gccgaggtga agttcgaggg cgacaccctg gtgaaccgca tcgagctgaa gggcatcgac 1680
ttcaaggagg acggcaacat cctggggcac aagctggagt acaactacaa cagccacaac 1740
gtctatatca tggccgacaa gcagaagaac ggcatcaagg tgaacttcaa gatccgccac 1800
aacatcgagg acggcagcgt gcagctcgcc gaccactacc agcagaacac ccccatcggc 1860
gacggccccg tgctgctgcc cgacaaccac tacctgagct accagtccgc cctgagcaaa 1920
gaccccaacg agaagcgcga tcacatggtc ctgctggagt tcgtgaccgc cgccgggatc 1980
actctcggca tggacgagct gtacaagtaa agcggccgcg actctagatc ataatcagcc 2040
ataccacatt tgtagaggtt ttacttgctt taaaaaacct cccacacctc cccctgaacc 2100
tgaaacataa aatgaatgca attgttgttg ttaacttgtt tattgcagct tataatggtt 2160
acaaataaag caatagcatc acaaatttca caaataaagc atttttttca ctgcattcta 2220
gttgtggttt gtccaaactc atcaatgtat cttaaggcgt aaattgtaag cgttaatatt 2280
ttgttaaaat tcgcgttaaa tttttgttaa atcagctcat tttttaacca ataggccgaa 2340
atcggcaaaa tcccttataa atcaaaagaa tagaccgaga tagggttgag tgttgttcca 2400
gtttggaaca agagtccact attaaagaac gtggactcca acgtcaaagg gcgaaaaacc 2460
gtctatcagg gcgatggccc actacgtgaa ccatcaccct aatcaagttt tttggggtcg 2520
aggtgccgta aagcactaaa tcggaaccct aaagggagcc cccgatttag agcttgacgg 2580
ggaaagccgg cgaacgtggc gagaaaggaa gggaagaaag cgaaaggagc gggcgctagg 2640
gcgctggcaa gtgtagcggt cacgctgcgc gtaaccacca cacccgccgc gcttaatgcg 2700
ccgctacagg gcgcgtcagg tggcactttt cggggaaatg tgcgcggaac ccctatttgt 2760
ttatttttct aaatacattc aaatatgtat ccgctcatga gacaataacc ctgataaatg 2820
cttcaataat attgaaaaag gaagagtcct gaggcggaaa gaaccagctg tggaatgtgt 2880
gtcagttagg gtgtggaaag tccccaggct ccccagcagg cagaagtatg caaagcatgc 2940
atctcaatta gtcagcaacc aggtgtggaa agtccccagg ctccccagca ggcagaagta 3000
tgcaaagcat gcatctcaat tagtcagcaa ccatagtccc gcccctaact ccgcccatcc 3060
cgcccctaac tccgcccagt tccgcccatt ctccgcccca tggctgacta attttttta 3120 tttatgcaga ggccgaggcc gcctcggcct ctgagctatt ccagaagtag tgaggaggct 3180
tttttggagg cctaggcttt tgcaaagatc gatcaagaga caggatgagg atcgtttcgc 3240
atgattgaac aagatggatt gcacgcaggt tctccggccg cttgggtgga gaggctattc 3300
ggctatgact gggcacaaca gacaatcggc tgctctgatg ccgccgtgtt ccggctgtca 3360
gcgcaggggc gcccggttct ttttgtcaag accgacctgt ccggtgccct gaatgaactg 3420
caagacgagg cagcgcggct atcgtggctg gccacgacgg gcgttccttg cgcagctgtg 3480
ctcgacgttg tcactgaagc gggaagggac tggctgctat tgggcgaagt gccggggcag 3540
gatctcctgt catctcacct tgctcctgcc gagaaagtat ccatcatggc tgatgcaatg 3600
cggcggctgc atacgcttga tccggctacc tgcccattcg accaccaagc gaaacatcgc 3660
atcgagcgag cacgtactcg gatggaagcc ggtcttgtcg atcaggatga tctggacgaa 3720
gagcatcagg ggctcgcgcc agccgaactg ttcgccaggc tcaaggcgag catgcccgac 3780
ggcgaggatc tcgtcgtgac ccatggcgat gcctgcttgc cgaatatcat ggtggaaaat 3840

```
ggccgctttt ctggattcat cgactgtggc cggctgggtg tggcggaccg ctatcaggac   3900
atagcgttgg ctacccgtga tattgctgaa gagcttggcg gcgaatgggc tgaccgcttc   3960
ctcgtgcttt acggtatcgc cgctcccgat tcgcagcgca tcgccttcta tcgccttctt   4020
gacgagttct tctgagcggg actctggggt tcgaaatgac cgaccaagcg acgcccaacc   4080
tgccatcacg agatttcgat tccaccgccg ccttctatga aaggttgggc ttcggaatcg   4140
ttttccggga cgccggctgg atgatcctcc agcgcgggga tctcatgctg gagttcttcg   4200
cccaccctag gggaggcta actgaaacac ggaaggagac aataccggaa ggaacccgcg    4260
ctatgacggc aataaaaaga cagaataaaa cgcacggtgt tgggtcgttt gttcataaac   4320
gcggggttcg gtcccagggc tggcactctg tcgatacccc accgagaccc cattggggcc   4380
aatacgcccg cgtttcttcc ttttccccac cccacccccc aagttcgggt gaaggcccag   4440
ggctcgcagc caacgtcggg gcggcaggcc ctgccatagc ctcaggttac tcatatatac   4500
tttagattga tttaaaactt catttttaat ttaaaaggat ctaggtgaag atcctttttg   4560
ataatctcat gaccaaaatc ccttaacgtg agttttcgtt ccactgagcg tcagaccccg   4620
tagaaaagat caaaggatct tcttgagatc cttttttttct gcgcgtaatc tgctgcttgc  4680
aaacaaaaaa accaccgcta ccagcggtgg tttgtttgcc ggatcaagag ctaccaactc   4740
tttttccgaa ggtaactggc ttcagcagag cgcagatacc aaatactgtc cttctagtgt   4800
agccgtagtt aggccaccac ttcaagaact ctgtagcacc gcctacatac ctcgctctgc   4860
taatcctgtt accagtggct gctgccagtg gcgataagtc gtgtcttacc gggttggact   4920
caagacgata gttaccggat aaggcgcagc ggtcgggctg aacggggggt tcgtgcacac   4980
agcccagctt ggagcgaacg acctacaccg aactgagata cctacagcgt gagctatgag   5040
aaagcgccac gcttcccgaa gggagaaagg cggacaggta tccggtaagc ggcagggtcg   5100
gaacaggaga gcgcacgagg gagcttccag ggggaaacgc ctggtatctt tatagtcctg   5160
tcgggtttcg ccacctctga cttgagcgtc gatttttgtg atgctcgtca ggggggcgga   5220
gcctatggaa aaacgccagc aacgcggcct ttttacggtt cctggccttt tgctggcctt   5280
ttgctcacat gttctttcct gcgttatccc ctgattctgt ggataaccgt attaccgcca   5340
tgcat                                                               5345
```

<210> SEQ ID NO 26
<211> LENGTH: 460
<212> TYPE: PRT
<213> ORGANISM: Artificial Sequence
<220> FEATURE:
<223> OTHER INFORMATION: HIV-1 Nef YFP fusion protein Sequence

<400> SEQUENCE: 26

```
Met Gly Gly Lys Trp Ser Lys Ser Ser Ile Val Gly Trp Pro Ala Val
1               5                   10                  15

Arg Glu Arg Ile Arg Arg Thr Glu Pro Ala Ala Glu Gly Val Gly Ala
            20                  25                  30

Ala Ser Arg Asp Leu Asp Lys His Gly Ala Leu Thr Ser Ser Asn Thr
        35                  40                  45

Ala Gln Thr Asn Ala Asp Cys Ala Trp Leu Glu Ala Gln Glu Glu Glu
    50                  55                  60

Asn Glu Val Gly Phe Pro Val Arg Pro Gln Val Pro Leu Arg Pro Met
65                  70                  75                  80

Thr Tyr Lys Gly Ala Val Asp Leu Ser Phe Phe Leu Lys Glu Lys Gly
```

-continued

```
                85                  90                  95

Gly Leu Glu Gly Leu Thr Tyr Ser Lys Lys Arg Gln Glu Ile Leu Asp
            100                 105                 110

Leu Trp Val Tyr His Thr Gln Gly Tyr Phe Pro Asp Trp Gln Cys Tyr
        115                 120                 125

Thr Pro Gly Pro Gly Val Arg Tyr Pro Leu Thr Phe Gly Trp Cys Phe
    130                 135                 140

Lys Leu Val Pro Val Asp Pro Asp Glu Val Gly Glu Ala Asn Asn Gly
145                 150                 155                 160

Glu Asn Asn Cys Leu Leu His Pro Ile Ser Leu His Gly Met Glu Asp
                165                 170                 175

Pro Glu Arg Glu Val Leu Arg Trp Lys Phe Asp Ser His Leu Ala His
            180                 185                 190

Thr His Lys Ala Arg Glu Leu His Pro Glu Tyr Tyr Lys Asp Cys Ala
        195                 200                 205

Ser Thr Val Pro Arg Ala Arg Asp Pro Pro Val Ala Thr Met Val Ser
    210                 215                 220

Lys Gly Glu Glu Leu Phe Thr Gly Val Val Pro Ile Leu Val Glu Leu
225                 230                 235                 240

Asp Gly Asp Val Asn Gly His Lys Phe Ser Val Ser Gly Glu Gly Glu
                245                 250                 255

Gly Asp Ala Thr Tyr Gly Lys Leu Thr Leu Lys Phe Ile Cys Thr Thr
            260                 265                 270

Gly Lys Leu Pro Val Pro Trp Pro Thr Leu Val Thr Thr Phe Gly Tyr
        275                 280                 285

Gly Leu Gln Cys Phe Ala Arg Tyr Pro Asp His Met Lys Gln His Asp
    290                 295                 300

Phe Phe Lys Ser Ala Met Pro Glu Gly Tyr Val Gln Glu Arg Thr Ile
305                 310                 315                 320

Phe Phe Lys Asp Asp Gly Asn Tyr Lys Thr Arg Ala Glu Val Lys Phe
                325                 330                 335

Glu Gly Asp Thr Leu Val Asn Arg Ile Glu Leu Lys Gly Ile Asp Phe
            340                 345                 350

Lys Glu Asp Gly Asn Ile Leu Gly His Lys Leu Glu Tyr Asn Tyr Asn
        355                 360                 365

Ser His Asn Val Tyr Ile Met Ala Asp Lys Gln Lys Asn Gly Ile Lys
    370                 375                 380

Val Asn Phe Lys Ile Arg His Asn Ile Glu Asp Gly Ser Val Gln Leu
385                 390                 395                 400

Ala Asp His Tyr Gln Gln Asn Thr Pro Ile Gly Asp Gly Pro Val Leu
                405                 410                 415

Leu Pro Asp Asn His Tyr Leu Ser Tyr Gln Ser Ala Leu Ser Lys Asp
            420                 425                 430

Pro Asn Glu Lys Arg Asp His Met Val Leu Leu Glu Phe Val Thr Ala
        435                 440                 445

Ala Gly Ile Thr Leu Gly Met Asp Glu Leu Tyr Lys
    450                 455                 460
```

```
<210> SEQ ID NO 27
<211> LENGTH: 7870
<212> TYPE: DNA
<213> ORGANISM: Artificial Sequence
<220> FEATURE:
<223> OTHER INFORMATION: construct Sequence containing ASK (g) cloned in
      pEYFP
```

<400> SEQUENCE: 27
tagttattaa tagtaatcaa ttacggggtc attagttcat agcccatata tggagttccg 60
cgttacataa cttacggtaa atggcccgcc tggctgaccg cccaacgacc cccgcccatt 120
gacgtcaata atgacgtatg ttcccatagt aacgccaata gggactttcc attgacgtca 180
atgggtggag tatttacggt aaactgccca cttggcagta catcaagtgt atcatatgcc 240
aagtacgccc cctattgacg tcaatgacgg taaatggccc gcctggcatt atgcccagta 300
catgacctta tgggactttc ctacttggca gtacatctac gtattagtca tcgctattac 360
catggtgatg cggttttggc agtacatcaa tgggcgtgga tagcggtttg actcacgggg 420
atttccaagt ctccacccca ttgacgtcaa tgggagtttg ttttggcacc aaaatcaacg 480
ggactttcca aaatgtcgta acaactccgc cccattgacg caaatgggcg gtaggcgtgt 540
acggtgggag gtctatataa gcagagctgg tttagtgaac cgtcagatcc gctagcgcta 600
ccggactcag atctcgagct caagcttcga attctgcagt cgacatgagc acggaggcgg 660
acgagggcat cactttctct gtgccaccct tcgccccctc gggcttctgc accatccccg 720
agggcggcat ctgcaggagg ggaggagcgg cggcggtggg cgagggcgag gagcaccagc 780
tgccaccgcc gccgccgggc agtttctgga acgtggagag cgccgctgcc cctggcatcg 840
gttgtccggc ggccacctcc tcgagcagtg ccacccgagg ccggggcagc tctgttggcg 900
ggggcagccg acggaccacg gtggcatatg tgatcaacga agcgagccaa gggcaactgg 960
tggtggccga gagcgaggcc ctgcagagct tgcgggaggc gtgcgagaca gtgggcgcca 1020
ccctggaaac cctgcatttt gggaaactcg actttggaga aaccaccgtg ctggaccgct 1080
tttacaatgc agatattgcg gtggtggaga tgagcgatgc cttccggcag ccgtccttgt 1140
tttaccacct tggggtgaga gaaagtttca gcatggccaa caacatcatc ctctactgtg 1200
atactaactc ggactctctg cagtcactga aggaaatcat ttgccagaag aatactatgt 1260
gcactgggaa ctacaccttt gttccttaca tgataactcc acataacaaa gtctactgct 1320
gtgacagcag cttcatgaag ggttgacag agctcatgca accgaacttc gagctgcttc 1380
ttggacccat ctgcttacct cttgtggatc gttttattca acttttgaag gtggcacaag 1440
caagttctag ccagtacttc cgggaatcta tactcaatga catcaggaaa gctcgtaatt 1500
tatacactgg taaagaattg gcagctgagt tggcaagaat tcggcagcga gtagataata 1560
tcgaagtctt gacagcagat attgtcataa atctgttact ttcctacaga gatatccagg 1620
actatgattc tattgtgaag ctggtagaga ctttagaaaa actgccaacc tttgatttgg 1680
cctcccatca ccatgtgaag tttcattatg catttgcact gaataggaga aatctccctg 1740
gtgacagagc aaaagctctt gatattatga ttcccatggt gcaaagcgaa ggacaagttg 1800
cttcagatat gtattgccta gttggtcgaa tctacaaaga tatgtttttg gactctaatt 1860
tcacggacac tgaaagcaga gaccatggag cttcttggtt caaaaaggca tttgaatctg 1920
agccaacact acagtcagga attaattatg cggtcctcct cctggcagct ggacaccagt 1980
ttgaatcttc ctttgagctc cggaaagttg gggtgaagct aagtagtctt cttggtaaaa 2040
agggaaactt ggaaaaactc cagagctact gggaagttgg attttttctg gggccagcg 2100
tcctagccaa tgaccacatg agagtcattc aagcatctga aaagcttttt aaactgaaga 2160
caccagcatg gtacctcaag tctattgtag agacaatttt aatatataag cattttgtga 2220
aactgaccac agaacagcct gtggccaagc aagaacttgt ggacttttgg atggatttcc 2280

-continued

```
tggtcgaggc cacaaagaca gatgttactg tggttaggtt tccagtatta atattagaac   2340
caaccaaaat ctatcaacct tcttatttgt ctatcaacaa tgaagttgag gaaaagacaa   2400
tctctatttg gcacgtgctt cctgatgaca agaaaggtat acatgagtgg aattttagtg   2460
cctcttctgt caggggagtg agtatttcta aatttgaaga aagatgctgc tttctttatg   2520
tgcttcacaa ttctgatgat ttccaaatct atttctgtac agaacttcat tgtaaaaagt   2580
tttttgagat ggtgaacacc attaccgaag agaaggggag aagcacagag gaaggagact   2640
gtgaaagtga cttgctggag tatgactatg aatatgatga aaatggtgac agagtcgttt   2700
taggaaaagg cacttatggg atagtctacg caggtcggga cttgagcaac caagtcagaa   2760
ttgctattaa ggaaatccca gagagagaca gcagatactc tcagcccctg catgaagaaa   2820
tagcattgca taaacacctg aagcacaaaa atattgtcca gtatctgggc tctttcagtg   2880
agaatggttt cattaaaatc ttcatggagc aggtccctgg aggaagtctt tctgctctcc   2940
ttcgttccaa atggggtcca ttaaaagaca atgagcaaac aattggcttt tatacaaagc   3000
aaatactgga aggattaaaa tatctccatg acaatcagat agttcaccgg gacataaagg   3060
gtgacaatgt gttgattaat acctacagtg gtgttctcaa gatctctgac ttcggaacat   3120
caaagaggct tgctggcata aacccctgta ctgaaacttt tactggtacc ctccagtata   3180
tggcaccaga aataatagat aaaggaccaa gaggctacgg aaaagcagca gacatctggt   3240
ctctgggctg tacaatcatt gaaatggcca caggaaaacc cccattttat gaactgggag   3300
aaccacaagc agctatgttc aaggtgggaa tgtttaaagt ccaccctgag atcccagagt   3360
ccatgtctgc agaggccaag gcattcatac tgaaatgttt tgaaccagat cctgacaaga   3420
gagcctgtgc taacgacttg cttgttgatg agtttttaaa agtttcaagc aaaaagaaaa   3480
agacacaacc taagctttca gctctttcag ctggatcaaa tgaatatctc aggagtatat   3540
ccttgccggt acctgtgctg gtggaggaca ccagcagcag cagtgagtac ggctcagttt   3600
cacccgacac ggagttgaaa gtggacccct tctctttcaa aacaagagcc aagtcctgcg   3660
gagaaagaga tgtcaaggga attcggacac tctttttggg cattccagat gagaattttg   3720
aagatcacag tgctcctcct tcccctgaag aaaaagattc tggattcttc atgctgagga   3780
aggacagtga gaggcgggat ccaccggtcg ccaccatggt gagcaagggc gaggagctgt   3840
tcaccggggt ggtgcccatc ctggtcgagc tggacggcga cgtaaacggc cacaagttca   3900
gcgtgtccgg cgagggcgag ggcgatgcca cctacggcaa gctgaccctg aagttcatct   3960
gcaccaccgg caagctgccc gtgccctggc ccaccctcgt gaccaccttc ggctacggcc   4020
tgcagtgctt cgcccgctac cccgaccaca tgaagcagca cgacttcttc aagtccgcca   4080
tgcccgaagg ctacgtccag gagcgcacca tcttcttcaa ggacgacggc aactacaaga   4140
cccgcgccga ggtgaagttc gagggcgaca ccctggtgaa ccgcatcgag ctgaagggca   4200
tcgacttcaa ggaggacggc aacatcctgg ggcacaagct ggagtacaac tacaacagcc   4260
acaacgtcta tatcatggcc gacaagcaga agaacggcat caaggtgaac ttcaagatcc   4320
gccacaacat cgaggacggc agcgtgcagc tcgccgacca ctaccagcag aacaccccca   4380
tcggcgacgg ccccgtgctg ctgcccgaca accactacct gagctaccag tccgccctga   4440
gcaaagaccc caacgagaag cgcgatcaca tggtcctgct ggagttcgtg accgccgccg   4500
ggatcactct cggcatggac gagctgtaca agtaaagcgg ccgcgactct agatcataat   4560
cagccatacc acatttgtag aggttttact tgctttaaaa aacctcccac acctcccccct   4620
gaacctgaaa cataaaatga atgcaattgt tgttgttaac ttgtttattg cagcttataa   4680
```

-continued

```
tggttacaaa taaagcaata gcatcacaaa tttcacaaat aaagcatttt tttcactgca   4740
ttctagttgt ggtttgtcca aactcatcaa tgtatcttaa ggcgtaaatt gtaagcgtta   4800
atattttgtt aaaattcgcg ttaaattttt gttaaatcag ctcatttttt aaccaatagg   4860
ccgaaatcgg caaaatccct tataaatcaa aagaatagac cgagataggg ttgagtgttg   4920
ttccagtttg gaacaagagt ccactattaa agaacgtgga ctccaacgtc aaagggcgaa   4980
aaaccgtcta tcagggcgat ggcccactac gtgaaccatc accctaatca agttttttgg   5040
ggtcgaggtg ccgtaaagca ctaaatcgga accctaaagg gagcccccga tttagagctt   5100
gacggggaaa gccggcgaac gtggcgagaa aggaagggaa gaaagcgaaa ggagcgggcg   5160
ctagggcgct ggcaagtgta gcggtcacgc tgcgcgtaac caccacaccc gccgcgctta   5220
atgcgccgct acagggcgcg tcaggtggca cttttcgggg aaatgtgcgc ggaaccccta   5280
tttgtttatt tttctaaata cattcaaata tgtatccgct catgagacaa taaccctgat   5340
aaatgcttca ataatattga aaaaggaaga gtcctgaggc ggaaagaacc agctgtggaa   5400
tgtgtgtcag ttagggtgtg gaaagtcccc aggctcccca gcaggcagaa gtatgcaaag   5460
catgcatctc aattagtcag caaccaggtg tggaaagtcc ccaggctccc cagcaggcag   5520
aagtatgcaa agcatgcatc tcaattagtc agcaaccata gtcccgcccc taactccgcc   5580
catcccgccc ctaactccgc ccagttccgc ccattctccg ccccatggct gactaatttt   5640
ttttatttat gcagaggccg aggccgcctc ggcctctgag ctattccaga agtagtgagg   5700
aggctttttt ggaggcctag gcttttgcaa agatcgatca agagacagga tgaggatcgt   5760
ttcgcatgat tgaacaagat ggattgcacg caggttctcc ggccgcttgg gtggagaggc   5820
tattcggcta tgactgggca caacagacaa tcggctgctc tgatgccgcc gtgttccggc   5880
tgtcagcgca ggggcgcccg gttctttttg tcaagaccga cctgtccggt gccctgaatg   5940
aactgcaaga cgaggcagcg cggctatcgt ggctggccac gacgggcgtt ccttgcgcag   6000
ctgtgctcga cgttgtcact gaagcgggaa gggactggct gctattgggc gaagtgccgg   6060
ggcaggatct cctgtcatct caccttgctc ctgccgagaa agtatccatc atggctgatg   6120
caatgcggcg gctgcatacg cttgatccgg ctacctgccc attcgaccac caagcgaaac   6180
atcgcatcga gcgagcacgt actcggatgg aagccggtct tgtcgatcag gatgatctgg   6240
acgaagagca tcaggggctc gcgccagccg aactgttcgc caggctcaag gcgagcatgc   6300
ccgacggcga ggatctcgtc gtgacccatg gcgatgcctg cttgccgaat atcatggtgg   6360
aaaatggccg cttttctgga ttcatcgact gtggccggct gggtgtggcg gaccgctatc   6420
aggacatagc gttggctacc cgtgatattg ctgaagagct tggcggcgaa tgggctgacc   6480
gcttcctcgt gctttacggt atcgccgctc ccgattcgca gcgcatcgcc ttctatcgcc   6540
ttcttgacga gttcttctga gcgggactct ggggttcgaa atgaccgacc aagcgacgcc   6600
caacctgcca tcacgagatt tcgattccac cgccgccttc tatgaaaggt tgggcttcgg   6660
aatcgttttc cgggacgccg gctggatgat cctccagcgc ggggatctca tgctggagtt   6720
cttcgcccac cctaggggga ggctaactga aacacggaag gagacaatac cggaaggaac   6780
ccgcgctatg acggcaataa aaagacagaa taaaacgcac ggtgttgggt cgtttgttca   6840
taaacgcggg gttcggtccc agggctggca ctctgtcgat accccaccga gaccccattg   6900
gggccaatac gcccgcgttt cttccttttc cccaccccac cccccaagtt cgggtgaagg   6960
cccagggctc gcagccaacg tcggggcggc aggccctgcc atagcctcag gttactcata   7020
```

-continued

```
tatactttag attgatttaa aacttcattt ttaatttaaa aggatctagg tgaagatcct   7080

ttttgataat ctcatgacca aaatccctta acgtgagttt tcgttccact gagcgtcaga   7140

ccccgtagaa aagatcaaag gatcttcttg agatcctttt tttctgcgcg taatctgctg   7200

cttgcaaaca aaaaaaccac cgctaccagc ggtggtttgt ttgccggatc aagagctacc   7260

aactcttttt ccgaaggtaa ctggcttcag cagagcgcag ataccaaata ctgtccttct   7320

agtgtagccg tagttaggcc accacttcaa gaactctgta gcaccgccta catacctcgc   7380

tctgctaatc ctgttaccag tggctgctgc cagtggcgat aagtcgtgtc ttaccgggtt   7440

ggactcaaga cgatagttac cggataaggc gcagcggtcg ggctgaacgg ggggttcgtg   7500

cacacagccc agcttggagc gaacgaccta caccgaactg agatacctac agcgtgagct   7560

atgagaaagc gccacgcttc ccgaagggag aaaggcggac aggtatccgg taagcggcag   7620

ggtcggaaca ggagagcgca cgagggagct tccaggggga aacgcctggt atctttatag   7680

tcctgtcggg tttcgccacc tctgacttga gcgtcgattt ttgtgatgct cgtcaggggg   7740

gcggagccta tggaaaaacg ccagcaacgc ggccttttta cggttcctgg ccttttgctg   7800

gccttttgct cacatgttct ttcctgcgtt atcccctgat tctgtggata accgtattac   7860

cgccatgcat                                                          7870
```

```
<210> SEQ ID NO 28
<211> LENGTH: 1296
<212> TYPE: PRT
<213> ORGANISM: Artificial Sequence
<220> FEATURE:
<223> OTHER INFORMATION: ASK1(g) YFP fusion protein sequence

<400> SEQUENCE: 28

Met Ser Thr Glu Ala Asp Glu Gly Ile Thr Phe Ser Val Pro Pro Phe
1               5                   10                  15

Ala Pro Ser Gly Phe Cys Thr Ile Pro Glu Gly Gly Ile Cys Arg Arg
            20                  25                  30

Gly Gly Ala Ala Ala Val Gly Glu Gly Glu Glu His Gln Leu Pro Pro
        35                  40                  45

Pro Pro Pro Gly Ser Phe Trp Asn Val Glu Ser Ala Ala Ala Pro Gly
    50                  55                  60

Ile Gly Cys Pro Ala Ala Thr Ser Ser Ser Ser Ala Thr Arg Gly Arg
65                  70                  75                  80

Gly Ser Ser Val Gly Gly Gly Ser Arg Arg Thr Thr Val Ala Tyr Val
                85                  90                  95

Ile Asn Glu Ala Ser Gln Gly Gln Leu Val Val Ala Glu Ser Glu Ala
            100                 105                 110

Leu Gln Ser Leu Arg Glu Ala Cys Glu Thr Val Gly Ala Thr Leu Glu
        115                 120                 125

Thr Leu His Phe Gly Lys Leu Asp Phe Gly Glu Thr Thr Val Leu Asp
    130                 135                 140

Arg Phe Tyr Asn Ala Asp Ile Ala Val Val Glu Met Ser Asp Ala Phe
145                 150                 155                 160

Arg Gln Pro Ser Leu Phe Tyr His Leu Gly Val Arg Glu Ser Phe Ser
                165                 170                 175

Met Ala Asn Asn Ile Ile Leu Tyr Cys Asp Thr Asn Ser Asp Ser Leu
            180                 185                 190

Gln Ser Leu Lys Glu Ile Ile Cys Gln Lys Asn Thr Met Cys Thr Gly
        195                 200                 205
```

```
Asn Tyr Thr Phe Val Pro Tyr Met Ile Thr Pro His Asn Lys Val Tyr
    210                 215                 220

Cys Cys Asp Ser Ser Phe Met Lys Gly Leu Thr Glu Leu Met Gln Pro
225                 230                 235                 240

Asn Phe Glu Leu Leu Leu Gly Pro Ile Cys Leu Pro Leu Val Asp Arg
                245                 250                 255

Phe Ile Gln Leu Leu Lys Val Ala Gln Ala Ser Ser Ser Gln Tyr Phe
            260                 265                 270

Arg Glu Ser Ile Leu Asn Asp Ile Arg Lys Ala Arg Asn Leu Tyr Thr
        275                 280                 285

Gly Lys Glu Leu Ala Ala Glu Leu Ala Arg Ile Arg Gln Arg Val Asp
    290                 295                 300

Asn Ile Glu Val Leu Thr Ala Asp Ile Val Ile Asn Leu Leu Leu Ser
305                 310                 315                 320

Tyr Arg Asp Ile Gln Asp Tyr Asp Ser Ile Val Lys Leu Val Glu Thr
                325                 330                 335

Leu Glu Lys Leu Pro Thr Phe Asp Leu Ala Ser His His His Val Lys
            340                 345                 350

Phe His Tyr Ala Phe Ala Leu Asn Arg Arg Asn Leu Pro Gly Asp Arg
        355                 360                 365

Ala Lys Ala Leu Asp Ile Met Ile Pro Met Val Gln Ser Glu Gly Gln
    370                 375                 380

Val Ala Ser Asp Met Tyr Cys Leu Val Gly Arg Ile Tyr Lys Asp Met
385                 390                 395                 400

Phe Leu Asp Ser Asn Phe Thr Asp Thr Glu Ser Arg Asp His Gly Ala
                405                 410                 415

Ser Trp Phe Lys Lys Ala Phe Glu Ser Glu Pro Thr Leu Gln Ser Gly
            420                 425                 430

Ile Asn Tyr Ala Val Leu Leu Leu Ala Ala Gly His Gln Phe Glu Ser
        435                 440                 445

Ser Phe Glu Leu Arg Lys Val Gly Val Lys Leu Ser Ser Leu Leu Gly
    450                 455                 460

Lys Lys Gly Asn Leu Glu Lys Leu Gln Ser Tyr Trp Glu Val Gly Phe
465                 470                 475                 480

Phe Leu Gly Ala Ser Val Leu Ala Asn Asp His Met Arg Val Ile Gln
                485                 490                 495

Ala Ser Glu Lys Leu Phe Lys Leu Lys Thr Pro Ala Trp Tyr Leu Lys
            500                 505                 510

Ser Ile Val Glu Thr Ile Leu Ile Tyr Lys His Phe Val Lys Leu Thr
        515                 520                 525

Thr Glu Gln Pro Val Ala Lys Gln Glu Leu Val Asp Phe Trp Met Asp
    530                 535                 540

Phe Leu Val Glu Ala Thr Lys Thr Asp Val Thr Val Val Arg Phe Pro
545                 550                 555                 560

Val Leu Ile Leu Glu Pro Thr Lys Ile Tyr Gln Pro Ser Tyr Leu Ser
                565                 570                 575

Ile Asn Asn Glu Val Glu Glu Lys Thr Ile Ser Ile Trp His Val Leu
            580                 585                 590

Pro Asp Asp Lys Lys Gly Ile His Glu Trp Asn Phe Ser Ala Ser Ser
        595                 600                 605

Val Arg Gly Val Ser Ile Ser Lys Phe Glu Glu Arg Cys Cys Phe Leu
    610                 615                 620

Tyr Val Leu His Asn Ser Asp Asp Phe Gln Ile Tyr Phe Cys Thr Glu
```

-continued

```
625                 630                 635                 640

Leu His Cys Lys Lys Phe Phe Glu Met Val Asn Thr Ile Thr Glu Glu
                645                 650                 655

Lys Gly Arg Ser Thr Glu Glu Gly Asp Cys Glu Ser Asp Leu Leu Glu
            660                 665                 670

Tyr Asp Tyr Glu Tyr Asp Glu Asn Gly Asp Arg Val Val Leu Gly Lys
        675                 680                 685

Gly Thr Tyr Gly Ile Val Tyr Ala Gly Arg Asp Leu Ser Asn Gln Val
    690                 695                 700

Arg Ile Ala Ile Lys Glu Ile Pro Glu Arg Asp Ser Arg Tyr Ser Gln
705                 710                 715                 720

Pro Leu His Glu Glu Ile Ala Leu His Lys His Leu Lys His Lys Asn
                725                 730                 735

Ile Val Gln Tyr Leu Gly Ser Phe Ser Glu Asn Gly Phe Ile Lys Ile
            740                 745                 750

Phe Met Glu Gln Val Pro Gly Gly Ser Leu Ser Ala Leu Leu Arg Ser
        755                 760                 765

Lys Trp Gly Pro Leu Lys Asp Asn Glu Gln Thr Ile Gly Phe Tyr Thr
    770                 775                 780

Lys Gln Ile Leu Glu Gly Leu Lys Tyr Leu His Asp Asn Gln Ile Val
785                 790                 795                 800

His Arg Asp Ile Lys Gly Asp Asn Val Leu Ile Asn Thr Tyr Ser Gly
                805                 810                 815

Val Leu Lys Ile Ser Asp Phe Gly Thr Ser Lys Arg Leu Ala Gly Ile
            820                 825                 830

Asn Pro Cys Thr Glu Thr Phe Thr Gly Thr Leu Gln Tyr Met Ala Pro
        835                 840                 845

Glu Ile Ile Asp Lys Gly Pro Arg Gly Tyr Gly Lys Ala Ala Asp Ile
    850                 855                 860

Trp Ser Leu Gly Cys Thr Ile Ile Glu Met Ala Thr Gly Lys Pro Pro
865                 870                 875                 880

Phe Tyr Glu Leu Gly Glu Pro Gln Ala Ala Met Phe Lys Val Gly Met
                885                 890                 895

Phe Lys Val His Pro Glu Ile Pro Glu Ser Met Ser Ala Glu Ala Lys
            900                 905                 910

Ala Phe Ile Leu Lys Cys Phe Glu Pro Asp Pro Asp Lys Arg Ala Cys
        915                 920                 925

Ala Asn Asp Leu Leu Val Asp Glu Phe Leu Lys Val Ser Ser Lys Lys
    930                 935                 940

Lys Lys Thr Gln Pro Lys Leu Ser Ala Leu Ser Ala Gly Ser Asn Glu
945                 950                 955                 960

Tyr Leu Arg Ser Ile Ser Leu Pro Val Pro Val Leu Val Glu Asp Thr
                965                 970                 975

Ser Ser Ser Ser Glu Tyr Gly Ser Val Ser Pro Asp Thr Glu Leu Lys
            980                 985                 990

Val Asp Pro Phe Ser Phe Lys Thr  Arg Ala Lys Ser Cys  Gly Glu Arg
        995                 1000                 1005

Asp Val  Lys Gly Ile Arg Thr  Leu Phe Leu Gly Ile  Pro Asp Glu
    1010                 1015                 1020

Asn Phe  Glu Asp His Ser Ala  Pro Pro Ser Pro Glu  Glu Lys Asp
    1025                 1030                 1035

Ser Gly  Phe Phe Met Leu Arg  Lys Asp Ser Glu Arg  Arg Asp Pro
    1040                 1045                 1050
```

-continued

Pro Val Ala Thr Met Val Ser Lys Gly Glu Glu Leu Phe Thr Gly
    1055                1060                1065

Val Val Pro Ile Leu Val Glu Leu Asp Gly Asp Val Asn Gly His
    1070                1075                1080

Lys Phe Ser Val Ser Gly Glu Gly Glu Gly Asp Ala Thr Tyr Gly
    1085                1090                1095

Lys Leu Thr Leu Lys Phe Ile Cys Thr Thr Gly Lys Leu Pro Val
    1100                1105                1110

Pro Trp Pro Thr Leu Val Thr Thr Phe Gly Tyr Gly Leu Gln Cys
    1115                1120                1125

Phe Ala Arg Tyr Pro Asp His Met Lys Gln His Asp Phe Phe Lys
    1130                1135                1140

Ser Ala Met Pro Glu Gly Tyr Val Gln Glu Arg Thr Ile Phe Phe
    1145                1150                1155

Lys Asp Asp Gly Asn Tyr Lys Thr Arg Ala Glu Val Lys Phe Glu
    1160                1165                1170

Gly Asp Thr Leu Val Asn Arg Ile Glu Leu Lys Gly Ile Asp Phe
    1175                1180                1185

Lys Glu Asp Gly Asn Ile Leu Gly His Lys Leu Glu Tyr Asn Tyr
    1190                1195                1200

Asn Ser His Asn Val Tyr Ile Met Ala Asp Lys Gln Lys Asn Gly
    1205                1210                1215

Ile Lys Val Asn Phe Lys Ile Arg His Asn Ile Glu Asp Gly Ser
    1220                1225                1230

Val Gln Leu Ala Asp His Tyr Gln Gln Asn Thr Pro Ile Gly Asp
    1235                1240                1245

Gly Pro Val Leu Leu Pro Asp Asn His Tyr Leu Ser Tyr Gln Ser
    1250                1255                1260

Ala Leu Ser Lys Asp Pro Asn Glu Lys Arg Asp His Met Val Leu
    1265                1270                1275

Leu Glu Phe Val Thr Ala Ala Gly Ile Thr Leu Gly Met Asp Glu
    1280                1285                1290

Leu Tyr Lys
    1295

<210> SEQ ID NO 29
<211> LENGTH: 6919
<212> TYPE: DNA
<213> ORGANISM: Artificial Sequence
<220> FEATURE:
<223> OTHER INFORMATION: construct Sequence containing ASK (h) cloned in pEYFP

<400> SEQUENCE: 29
tagttattaa tagtaatcaa ttacggggtc attagttcat agcccatata tggagttccg 60
cgttacataa cttacggtaa atggcccgcc tggctgaccg cccaacgacc cccgcccatt 120
gacgtcaata atgacgtatg ttcccatagt aacgccaata gggactttcc attgacgtca 180
atgggtggag tatttacggt aaactgccca cttggcagta catcaagtgt atcatatgcc 240
aagtacgccc cctattgacg tcaatgacgg taaatggccc gcctggcatt atgcccagta 300
catgacctta tgggactttc ctacttggca gtacatctac gtattagtca tcgctattac 360
catggtgatg cggttttggc agtacatcaa tgggcgtgga tagcggtttg actcacgggg 420
atttccaagt ctccacccca ttgacgtcaa tgggagtttg ttttggcacc aaaatcaacg 480

```
ggactttcca aaatgtcgta acaactccgc cccattgacg caaatgggcg gtaggcgtgt    540
acggtgggag gtctatataa gcagagctgg tttagtgaac cgtcagatcc gctagcgcta    600
ccggactcag atctcgagct caagcttcga attctgcagt cgacatgctt tcctacagag    660
atatccagga ctatgattct attgtgaagc tggtagagac tttagaaaaa ctgccaacct    720
ttgatttggc ctcccatcac catgtgaagt ttcattatgc atttgcactg aataggagaa    780
atctccctgg tgacagagca aaagctcttg atattatgat tcccatggtg caaagcgaag    840
gacaagttgc ttcagatatg tattgcctag ttggtcgaat ctacaaagat atgtttttgg    900
actctaattt cacggacact gaaagcagag accatggagc ttcttggttc aaaaaggcat    960
ttgaatctga gccaacacta cagtcaggaa ttaattatgc ggtcctcctc ctggcagctg   1020
gacaccagtt tgaatcttcc tttgagctcc ggaaagttgg ggtgaagcta agtagtcttc   1080
ttggtaaaaa gggaaacttg gaaaaactcc agagctactg ggaagttgga ttttttctgg   1140
gggccagcgt cctagccaat gaccacatga gagtcattca agcatctgaa aagcttttta   1200
aactgaagac accagcatgg tacctcaagt ctattgtaga gacaatttta atatataagc   1260
attttgtgaa actgaccaca gaacagcctg tggccaagca agaacttgtg gacttttgga   1320
tggatttcct ggtcgaggcc acaaagacag atgttactgt ggttaggttt ccagtattaa   1380
tattagaacc aaccaaaatc tatcaacctt cttatttgtc tatcaacaat gaagttgagg   1440
aaaagacaat ctctatttgg cacgtgcttc ctgatgacaa gaaaggtata catgagtgga   1500
attttagtgc ctcttctgtc aggggagtga gtatttctaa atttgaagaa agatgctgct   1560
ttctttatgt gcttcacaat tctgatgatt tccaaatcta tttctgtaca gaacttcatt   1620
gtaaaaagtt ttttgagatg gtgaacacca ttaccgaaga gaaggggaga agcacagagg   1680
aaggagactg tgaaagtgac ttgctggagt atgactatga atatgatgaa aatggtgaca   1740
gagtcgtttt aggaaaaggc acttatggga tagtctacgc aggtcgggac ttgagcaacc   1800
aagtcagaat tgctattaag gaaatcccag agagagacag cagatactct cagcccctgc   1860
atgaagaaat agcattgcat aaacacctga agcacaaaaa tattgtccag tatctgggct   1920
ctttcagtga gaatggtttc attaaaatct tcatggagca ggtccctgga ggaagtcttt   1980
ctgctctcct tcgttccaaa tggggtccat taaaagacaa tgagcaaaca attggctttt   2040
atacaaagca aatactggaa ggattaaaat atctccatga caatcagata gttcaccggg   2100
acataaaggg tgacaatgtg ttgattaata cctacagtgg tgttctcaag atctctgact   2160
tcggaacatc aaagaggctt gctggcataa accccctgtac tgaaactttt actggtaccc   2220
tccagtatat ggcaccagaa ataatagata aaggaccaag aggctacgga aaagcagcag   2280
acatctggtc tctgggctgt acaatcattg aaatggccac aggaaaaccc ccattttatg   2340
aactgggaga accacaagca gctatgttca aggtgggaat gtttaaagtc caccctgaga   2400
tcccagagtc catgtctgca gaggccaagg cattcatact gaaatgtttt gaaccagatc   2460
ctgacaagag agcctgtgct aacgacttgc ttgttgatga gtttttaaaa gtttcaagca   2520
aaaagaaaaa gacacaacct aagctttcag ctctttcagc tggatcaaat gaatatctca   2580
ggagtatatc cttgccggta cctgtgctgg tggaggacac cagcagcagc agtgagtacg   2640
gctcagtttc acccgacacg gagttgaaag tggacccctt ctctttcaaa acaagagcca   2700
agtcctgcgg agaaagagat gtcaagggaa ttcggacact ctttttgggc attccagatg   2760
agaattttga agatcacagt gctcctcctt cccctgaaga aaaagattct ggattcttca   2820
tgctgaggaa ggacagtgag aggcgggatc caccggtcgc caccatggtg agcaagggcg   2880
```

```
aggagctgtt caccggggtg gtgcccatcc tggtcgagct ggacggcgac gtaaacggcc   2940
acaagttcag cgtgtccggc gagggcgagg gcgatgccac ctacggcaag ctgaccctga   3000
agttcatctg caccaccggc aagctgcccg tgccctggcc caccctcgtg accaccttcg   3060
gctacggcct gcagtgcttc gcccgctacc ccgaccacat gaagcagcac gacttcttca   3120
agtccgccat gcccgaaggc tacgtccagg agcgcaccat cttcttcaag gacgacggca   3180
actacaagac ccgcgccgag gtgaagttcg agggcgacac cctggtgaac cgcatcgagc   3240
tgaagggcat cgacttcaag gaggacggca acatcctggg gcacaagctg gagtacaact   3300
acaacagcca caacgtctat atcatggccg acaagcagaa gaacggcatc aaggtgaact   3360
tcaagatccg ccacaacatc gaggacggca gcgtgcagct cgccgaccac taccagcaga   3420
acacccccat cggcgacggc cccgtgctgc tgcccgacaa ccactacctg agctaccagt   3480
ccgccctgag caaagacccc aacgagaagc gcgatcacat ggtcctgctg gagttcgtga   3540
ccgccgccgg gatcactctc ggcatggacg agctgtacaa gtaaagcggc cgcgactcta   3600
gatcataatc agccatacca catttgtaga ggttttactt gctttaaaaa acctcccaca   3660
cctccccctg aacctgaaac ataaaatgaa tgcaattgtt gttgttaact tgtttattgc   3720
agcttataat ggttacaaat aaagcaatag catcacaaat ttcacaaata aagcattttt   3780
ttcactgcat tctagttgtg gtttgtccaa actcatcaat gtatcttaag gcgtaaattg   3840
taagcgttaa tattttgtta aaattcgcgt taaatttttg ttaaatcagc tcatttttta   3900
accaataggc cgaaatcggc aaaatccctt ataaatcaaa agaatagacc gagatagggt   3960
tgagtgttgt tccagtttgg aacaagagtc cactattaaa gaacgtggac tccaacgtca   4020
aagggcgaaa aaccgtctat cagggcgatg gcccactacg tgaaccatca ccctaatcaa   4080
gtttttgggg gtcgaggtgc cgtaaagcac taaatcggaa ccctaaaggg agcccccgat   4140
ttagagcttg acggggaaag ccggcgaacg tggcgagaaa ggaagggaag aaagcgaaag   4200
gagcgggcgc tagggcgctg gcaagtgtag cggtcacgct gcgcgtaacc accacacccg   4260
ccgcgcttaa tgcgccgcta cagggcgcgt caggtggcac ttttcgggga aatgtgcgcg   4320
gaacccctat ttgtttattt ttctaaatac attcaaatat gtatccgctc atgagacaat   4380
aaccctgata aatgcttcaa taatattgaa aaaggaagag tcctgaggcg gaaagaacca   4440
gctgtggaat gtgtgtcagt tagggtgtgg aaagtcccca ggctccccag caggcagaag   4500
tatgcaaagc atgcatctca attagtcagc aaccaggtgt ggaaagtccc caggctcccc   4560
agcaggcaga agtatgcaaa gcatgcatct caattagtca gcaaccatag tcccgcccct   4620
aactccgccc atcccgcccc taactccgcc cagttccgcc cattctccgc cccatggctg   4680
actaattttt tttatttatg cagaggccga ggccgcctcg gcctctgagc tattccagaa   4740
gtagtgagga ggcttttttg gaggcctagg cttttgcaaa gatcgatcaa gagacaggat   4800
gaggatcgtt tcgcatgatt gaacaagatg gattgcacgc aggttctccg gccgcttggg   4860
tggagaggct attcggctat gactgggcac aacagacaat cggctgctct gatgccgccg   4920
tgttccggct gtcagcgcag gggcgcccgg ttctttttgt caagaccgac ctgtccggtg   4980
ccctgaatga actgcaagac gaggcagcgc ggctatcgtg gctggccacg acgggcgttc   5040
cttgcgcagc tgtgctcgac gttgtcactg aagcgggaag ggactggctg ctattgggcg   5100
aagtgccggg gcaggatctc ctgtcatctc accttgctcc tgccgagaaa gtatccatca   5160
tggctgatgc aatgcggcgg ctgcatacgc ttgatccggc tacctgccca ttcgaccacc   5220
```

-continued

```
aagcgaaaca tcgcatcgag cgagcacgta ctcggatgga agccggtctt gtcgatcagg   5280

atgatctgga cgaagagcat caggggctcg cgccagccga actgttcgcc aggctcaagg   5340

cgagcatgcc cgacggcgag gatctcgtcg tgacccatgg cgatgcctgc ttgccgaata   5400

tcatggtgga aaatggccgc ttttctggat tcatcgactg tggccggctg ggtgtggcgg   5460

accgctatca ggacatagcg ttggctaccc gtgatattgc tgaagagctt ggcggcgaat   5520

gggctgaccg cttcctcgtg ctttacggta tcgccgctcc cgattcgcag cgcatcgcct   5580

tctatcgcct tcttgacgag ttcttctgag cgggactctg gggttcgaaa tgaccgacca   5640

agcgacgccc aacctgccat cacgagattt cgattccacc gccgccttct atgaaaggtt   5700

gggcttcgga atcgttttcc gggacgccgg ctggatgatc ctccagcgcg gggatctcat   5760

gctggagttc ttcgcccacc ctagggggag gctaactgaa acacggaagg agacaatacc   5820

ggaaggaacc cgcgctatga cggcaataaa aagacagaat aaaacgcacg gtgttgggtc   5880

gtttgttcat aaacgcgggg ttcggtccca gggctggcac tctgtcgata ccccaccgag   5940

accccattgg ggccaatacg cccgcgtttc ttcctttttcc ccaccccacc ccccaagttc   6000

gggtgaaggc ccagggctcg cagccaacgt cggggcggca ggccctgcca tagcctcagg   6060

ttactcatat atactttaga ttgatttaaa acttcatttt taatttaaaa ggatctaggt   6120

gaagatcctt tttgataatc tcatgaccaa aatcccttaa cgtgagtttt cgttccactg   6180

agcgtcagac cccgtagaaa agatcaaagg atcttcttga gatccttttt ttctgcgcgt   6240

aatctgctgc ttgcaaacaa aaaaaccacc gctaccagcg gtggtttgtt tgccggatca   6300

agagctacca actctttttc cgaaggtaac tggcttcagc agagcgcaga taccaaatac   6360

tgtccttcta gtgtagccgt agttaggcca ccacttcaag aactctgtag caccgcctac   6420

atacctcgct ctgctaatcc tgttaccagt ggctgctgcc agtggcgata agtcgtgtct   6480

taccgggttg gactcaagac gatagttacc ggataaggcg cagcggtcgg gctgaacggg   6540

gggttcgtgc acacagccca gcttggagcg aacgacctac accgaactga gatacctaca   6600

gcgtgagcta tgagaaagcg ccacgcttcc cgaagggaga aaggcggaca ggtatccggt   6660

aagcggcagg gtcggaacag gagagcgcac gagggagctt ccagggggaa acgcctggta   6720

tctttatagt cctgtcgggt ttcgccacct ctgacttgag cgtcgatttt tgtgatgctc   6780

gtcagggggg cggagcctat ggaaaaacgc cagcaacgcg gcctttttac ggttcctggc   6840

cttttgctgg ccttttgctc acatgttctt tcctgcgtta tcccctgatt ctgtggataa   6900

ccgtattacc gccatgcat                                                 6919
```

```
<210> SEQ ID NO 30
<211> LENGTH: 979
<212> TYPE: PRT
<213> ORGANISM: Artificial Sequence
<220> FEATURE:
<223> OTHER INFORMATION: ASK1(h) YFP fusion protein sequence

<400> SEQUENCE: 30

Met Leu Ser Tyr Arg Asp Ile Gln Asp Tyr Asp Ser Ile Val Lys Leu
1               5                   10                  15

Val Glu Thr Leu Glu Lys Leu Pro Thr Phe Asp Leu Ala Ser His His
            20                  25                  30

His Val Lys Phe His Tyr Ala Phe Ala Leu Asn Arg Arg Asn Leu Pro
        35                  40                  45

Gly Asp Arg Ala Lys Ala Leu Asp Ile Met Ile Pro Met Val Gln Ser
    50                  55                  60
```

-continued

```
Glu Gly Gln Val Ala Ser Asp Met Tyr Cys Leu Val Gly Arg Ile Tyr
65                  70                  75                  80

Lys Asp Met Phe Leu Asp Ser Asn Phe Thr Asp Thr Glu Ser Arg Asp
                85                  90                  95

His Gly Ala Ser Trp Phe Lys Lys Ala Phe Glu Ser Glu Pro Thr Leu
            100                 105                 110

Gln Ser Gly Ile Asn Tyr Ala Val Leu Leu Leu Ala Ala Gly His Gln
        115                 120                 125

Phe Glu Ser Ser Phe Glu Leu Arg Lys Val Gly Val Lys Leu Ser Ser
    130                 135                 140

Leu Leu Gly Lys Lys Gly Asn Leu Glu Lys Leu Gln Ser Tyr Trp Glu
145                 150                 155                 160

Val Gly Phe Phe Leu Gly Ala Ser Val Leu Ala Asn Asp His Met Arg
                165                 170                 175

Val Ile Gln Ala Ser Glu Lys Leu Phe Lys Leu Lys Thr Pro Ala Trp
            180                 185                 190

Tyr Leu Lys Ser Ile Val Glu Thr Ile Leu Ile Tyr Lys His Phe Val
        195                 200                 205

Lys Leu Thr Thr Glu Gln Pro Val Ala Lys Gln Glu Leu Val Asp Phe
    210                 215                 220

Trp Met Asp Phe Leu Val Glu Ala Thr Lys Thr Asp Val Thr Val Val
225                 230                 235                 240

Arg Phe Pro Val Leu Ile Leu Glu Pro Thr Lys Ile Tyr Gln Pro Ser
                245                 250                 255

Tyr Leu Ser Ile Asn Asn Glu Val Glu Glu Lys Thr Ile Ser Ile Trp
            260                 265                 270

His Val Leu Pro Asp Asp Lys Lys Gly Ile His Glu Trp Asn Phe Ser
        275                 280                 285

Ala Ser Ser Val Arg Gly Val Ser Ile Ser Lys Phe Glu Glu Arg Cys
    290                 295                 300

Cys Phe Leu Tyr Val Leu His Asn Ser Asp Asp Phe Gln Ile Tyr Phe
305                 310                 315                 320

Cys Thr Glu Leu His Cys Lys Lys Phe Phe Glu Met Val Asn Thr Ile
                325                 330                 335

Thr Glu Glu Lys Gly Arg Ser Thr Glu Glu Gly Asp Cys Glu Ser Asp
            340                 345                 350

Leu Leu Glu Tyr Asp Tyr Glu Tyr Asp Glu Asn Gly Asp Arg Val Val
        355                 360                 365

Leu Gly Lys Gly Thr Tyr Gly Ile Val Tyr Ala Gly Arg Asp Leu Ser
    370                 375                 380

Asn Gln Val Arg Ile Ala Ile Lys Glu Ile Pro Glu Arg Asp Ser Arg
385                 390                 395                 400

Tyr Ser Gln Pro Leu His Glu Glu Ile Ala Leu His Lys His Leu Lys
                405                 410                 415

His Lys Asn Ile Val Gln Tyr Leu Gly Ser Phe Ser Glu Asn Gly Phe
            420                 425                 430

Ile Lys Ile Phe Met Glu Gln Val Pro Gly Gly Ser Leu Ser Ala Leu
        435                 440                 445

Leu Arg Ser Lys Trp Gly Pro Leu Lys Asp Asn Glu Gln Thr Ile Gly
    450                 455                 460

Phe Tyr Thr Lys Gln Ile Leu Glu Gly Leu Lys Tyr Leu His Asp Asn
465                 470                 475                 480
```

-continued

```
Gln Ile Val His Arg Asp Ile Lys Gly Asp Asn Val Leu Ile Asn Thr
                485                 490                 495

Tyr Ser Gly Val Leu Lys Ile Ser Asp Phe Gly Thr Ser Lys Arg Leu
            500                 505                 510

Ala Gly Ile Asn Pro Cys Thr Glu Thr Phe Thr Gly Thr Leu Gln Tyr
        515                 520                 525

Met Ala Pro Glu Ile Ile Asp Lys Gly Pro Arg Gly Tyr Gly Lys Ala
    530                 535                 540

Ala Asp Ile Trp Ser Leu Gly Cys Thr Ile Ile Glu Met Ala Thr Gly
545                 550                 555                 560

Lys Pro Pro Phe Tyr Glu Leu Gly Glu Pro Gln Ala Ala Met Phe Lys
                565                 570                 575

Val Gly Met Phe Lys Val His Pro Glu Ile Pro Glu Ser Met Ser Ala
            580                 585                 590

Glu Ala Lys Ala Phe Ile Leu Lys Cys Phe Glu Pro Asp Pro Asp Lys
        595                 600                 605

Arg Ala Cys Ala Asn Asp Leu Leu Val Asp Glu Phe Leu Lys Val Ser
    610                 615                 620

Ser Lys Lys Lys Lys Thr Gln Pro Lys Leu Ser Ala Leu Ser Ala Gly
625                 630                 635                 640

Ser Asn Glu Tyr Leu Arg Ser Ile Ser Leu Pro Val Pro Val Leu Val
                645                 650                 655

Glu Asp Thr Ser Ser Ser Ser Glu Tyr Gly Ser Val Ser Pro Asp Thr
            660                 665                 670

Glu Leu Lys Val Asp Pro Phe Ser Phe Lys Thr Arg Ala Lys Ser Cys
        675                 680                 685

Gly Glu Arg Asp Val Lys Gly Ile Arg Thr Leu Phe Leu Gly Ile Pro
    690                 695                 700

Asp Glu Asn Phe Glu Asp His Ser Ala Pro Pro Ser Pro Glu Glu Lys
705                 710                 715                 720

Asp Ser Gly Phe Phe Met Leu Arg Lys Asp Ser Glu Arg Arg Asp Pro
                725                 730                 735

Pro Val Ala Thr Met Val Ser Lys Gly Glu Glu Leu Phe Thr Gly Val
            740                 745                 750

Val Pro Ile Leu Val Glu Leu Asp Gly Asp Val Asn Gly His Lys Phe
        755                 760                 765

Ser Val Ser Gly Glu Gly Glu Gly Asp Ala Thr Tyr Gly Lys Leu Thr
    770                 775                 780

Leu Lys Phe Ile Cys Thr Thr Gly Lys Leu Pro Val Pro Trp Pro Thr
785                 790                 795                 800

Leu Val Thr Thr Phe Gly Tyr Gly Leu Gln Cys Phe Ala Arg Tyr Pro
                805                 810                 815

Asp His Met Lys Gln His Asp Phe Phe Lys Ser Ala Met Pro Glu Gly
            820                 825                 830

Tyr Val Gln Glu Arg Thr Ile Phe Phe Lys Asp Asp Gly Asn Tyr Lys
        835                 840                 845

Thr Arg Ala Glu Val Lys Phe Glu Gly Asp Thr Leu Val Asn Arg Ile
    850                 855                 860

Glu Leu Lys Gly Ile Asp Phe Lys Glu Asp Gly Asn Ile Leu Gly His
865                 870                 875                 880

Lys Leu Glu Tyr Asn Tyr Asn Ser His Asn Val Tyr Ile Met Ala Asp
                885                 890                 895

Lys Gln Lys Asn Gly Ile Lys Val Asn Phe Lys Ile Arg His Asn Ile
```

```
            900                 905                 910

Glu Asp Gly Ser Val Gln Leu Ala Asp His Tyr Gln Gln Asn Thr Pro
        915                 920                 925

Ile Gly Asp Gly Pro Val Leu Leu Pro Asp Asn His Tyr Leu Ser Tyr
    930                 935                 940

Gln Ser Ala Leu Ser Lys Asp Pro Asn Glu Lys Arg Asp His Met Val
945                 950                 955                 960

Leu Leu Glu Phe Val Thr Ala Ala Gly Ile Thr Leu Gly Met Asp Glu
                965                 970                 975

Leu Tyr Lys


<210> SEQ ID NO 31
<211> LENGTH: 7429
<212> TYPE: DNA
<213> ORGANISM: Artificial Sequence
<220> FEATURE:
<223> OTHER INFORMATION: construct Sequence containing ASK (i) cloned in
      pEYFP

<400> SEQUENCE: 31

tagttattaa tagtaatcaa ttacggggtc attagttcat agcccatata tggagttccg     60

cgttacataa cttacggtaa atggcccgcc tggctgaccg cccaacgacc cccgcccatt    120

gacgtcaata atgacgtatg ttcccatagt aacgccaata gggactttcc attgacgtca    180

atgggtggag tatttacggt aaactgccca cttggcagta catcaagtgt atcatatgcc    240

aagtacgccc cctattgacg tcaatgacgg taaatggccc gcctggcatt atgcccagta    300

catgacctta tgggactttc ctacttggca gtacatctac gtattagtca tcgctattac    360

catggtgatg cggttttggc agtacatcaa tgggcgtgga tagcggtttg actcacgggg    420

atttccaagt ctccacccca ttgacgtcaa tgggagtttg ttttggcacc aaaatcaacg    480

ggactttcca aaatgtcgta acaactccgc cccattgacg caaatgggcg gtaggcgtgt    540

acggtgggag gtctatataa gcagagctgg tttagtgaac cgtcagatcc gctagcgcta    600

ccggactcag atctcgagct caagcttcga attctgcagt cgacatgagc acggaggcgg    660

acgagggcat cactttctct gtgccaccct tcgccccctc gggcttctgc accatccccg    720

agggcggcat ctgcaggagg ggaggagcgg cggcggtggg cgagggcgag gagcaccagc    780

tgccaccgcc gccgccgggc agtttctgga acgtggagag cgccgctgcc cctggcatcg    840

gttgtccggc ggccacctcc tcgagcagtg ccacccgagg ccggggcagc tctgttggcg    900

ggggcagccg acggaccacg gtggcatatg tgatcaacga agcgagccaa gggcaactgg    960

tggtggccga gagcgaggcc ctgcagagct tgcgggaggc gtgcgagaca gtgggcgcca   1020

ccctggaaac cctgcatttt gggaaactcg actttggaga aaccaccgtg ctggaccgct   1080

tttacaatgc agatattgcg gtggtggaga tgagcgatgc cttccggcag ccgtccttgt   1140

tttaccacct tggggtgaga gaaagtttca gcatggccaa caacatcatc ctctactgtg   1200

atactaactc ggactctctg cagtcactga aggaaatcat ttgccagaag aatactatgt   1260

gcactgggaa ctacaccttt gttccttaca tgataactcc acataacaaa gtctactgct   1320

gtgacagcag cttcatgaag ggggttgacag agctcatgca accgaacttc gagctgcttc   1380

ttggacccat ctgcttacct cttgtggatc gttttattca acttttgaag gtggcacaag   1440

caagttctag ccagtacttc cgggaatcta tactcaatga catcaggaaa gctcgtaatt   1500

tatacactgg taaagaattg gcagctgagt tggcaagaat tcggcagcga gtagataata   1560
```

-continued

```
tcgaagtctt gacagcagat attgtcataa atctgttact ttcctacaga gatatccagg   1620
actatgattc tattgtgaag ctggtagaga ctttagaaaa actgccaacc tttgatttgg   1680
cctcccatca ccatgtgaag tttcattatg catttgcact gaataggaga aatctccctg   1740
gtgacagagc aaaagctctt gatattatga ttcccatggt gcaaagcgaa ggacaagttg   1800
cttcagatat gtattgccta gttggtcgaa tctacaaaga tatgtttttg gactctaatt   1860
tcacggacac tgaaagcaga gaccatggag cttcttggtt caaaaaggca tttgaatctg   1920
agccaacact acagtcagga attaattatg cggtcctcct cctggcagct ggacaccagt   1980
ttgaatcttc ctttgagctc cggaaagttg gggtgaagct aagtagtctt cttggtaaaa   2040
agggaaactt ggaaaaactc cagagctact gggaagttgg atttttctg ggggccagcg    2100
tcctagccaa tgaccacatg agagtcattc aagcatctga aaagcttttt aaactgaaga   2160
caccagcatg gtacctcaag tctattgtag agacaatttt aatatataag cattttgtga   2220
aactgaccac agaacagcct gtggccaagc aagaacttgt ggacttttgg atggatttcc   2280
tggtcgaggc cacaaagaca gatgttactg tggttaggtt tccagtatta atattagaac   2340
caaccaaaat ctatcaacct tcttatttgt ctatcaacaa tgaagttgag gaaaagacaa   2400
tctctatttg gcacgtgctt cctgatgaca agaaaggtat acatgagtgg aattttagtg   2460
cctcttctgt caggggagtg agtatttcta aatttgaaga aagatgctgc tttctttatg   2520
tgcttcacaa ttctgatgat ttccaaatct atttctgtac agaacttcat tgtaaaaagt   2580
tttttgagat ggtgaacacc attaccgaag agaaggggag aagcacagag gaaggagact   2640
gtgaaagtga cttgctggag tatgactatg aatatgatga aaatggtgac agagtcgttt   2700
taggaaaagg cacttatggg atagtctacg caggtcggga cttgagcaac caagtcagaa   2760
ttgctattaa ggaaatccca gagagagaca gcagatactc tcagcccctg catgaagaaa   2820
tagcattgca taaacacctg aagcacaaaa atattgtcca gtatctgggc tctttcagtg   2880
agaatggttt cattaaaatc ttcatggagc aggtccctgg aggaagtctt tctgctctcc   2940
ttcgttccaa atggggtcca ttaaaagaca atgagcaaac aattggcttt tatacaaagc   3000
aaatactgga aggattaaaa tatctccatg acaatcagat agttcaccgg gacataaagg   3060
gtgacaatgt gttgattaat acctacagtg gtgttctcaa gatctctgac ttcggaacat   3120
caaagaggct tgctggcata aacccctgta ctgaaacttt tactggtacc ctccagtata   3180
tggcaccaga aataatagat aaaggaccaa gaggctacgg aaaagcagca gacatctggt   3240
ctctgggctg tacaatcatt gaaatggcca caggaaaacc cccattttat gaactgggag   3300
aaccacaagc agctatgttc aaggtgggaa tgtttaaagt ccaccctgag atccgggatc   3360
caccggtcgc caccatggtg agcaagggcg aggagctgtt caccggggtg gtgcccatcc   3420
tggtcgagct ggacggcgac gtaaacggcc acaagttcag cgtgtccggc gagggcgagg   3480
gcgatgccac ctacggcaag ctgaccctga agttcatctg caccaccggc aagctgcccg   3540
tgccctggcc caccctcgtg accaccttcg gctacggcct gcagtgcttc gcccgctacc   3600
ccgaccacat gaagcagcac gacttcttca agtccgccat gcccgaaggc tacgtccagg   3660
agcgcaccat cttcttcaag gacgacggca actacaagac ccgcgccgag gtgaagttcg   3720
agggcgacac cctggtgaac cgcatcgagc tgaagggcat cgacttcaag gaggacggca   3780
acatcctggg gcacaagctg gagtacaact acaacagcca caacgtctat atcatggccg   3840
acaagcagaa gaacggcatc aaggtgaact tcaagatccg ccacaacatc gaggacggca   3900
gcgtgcagct cgccgaccac taccagcaga acacccccat cggcgacggc cccgtgctgc   3960
```

```
tgcccgacaa ccactacctg agctaccagt ccgccctgag caaagacccc aacgagaagc   4020
gcgatcacat ggtcctgctg gagttcgtga ccgccgccgg gatcactctc ggcatggacg   4080
agctgtacaa gtaaagcggc cgcgactcta gatcataatc agccatacca catttgtaga   4140
ggttttactt gctttaaaaa acctcccaca cctccccctg aacctgaaac ataaaatgaa   4200
tgcaattgtt gttgttaact tgtttattgc agcttataat ggttacaaat aaagcaatag   4260
catcacaaat ttcacaaata aagcattttt ttcactgcat tctagttgtg gtttgtccaa   4320
actcatcaat gtatcttaag gcgtaaattg taagcgttaa tattttgtta aaattcgcgt   4380
taaatttttg ttaaatcagc tcatttttta accaataggc cgaaatcggc aaaatccctt   4440
ataaatcaaa agaatagacc gagatagggt tgagtgttgt tccagtttgg aacaagagtc   4500
cactattaaa gaacgtggac tccaacgtca aagggcgaaa aaccgtctat cagggcgatg   4560
gcccactacg tgaaccatca ccctaatcaa gttttttggg gtcgaggtgc cgtaaagcac   4620
taaatcggaa ccctaaaggg agcccccgat ttagagcttg acggggaaag ccggcgaacg   4680
tggcgagaaa ggaagggaag aaagcgaaag gagcgggcgc tagggcgctg gcaagtgtag   4740
cggtcacgct gcgcgtaacc accacacccg ccgcgcttaa tgcgccgcta cagggcgcgt   4800
caggtggcac ttttcgggga aatgtgcgcg gaacccctat ttgtttattt ttctaaatac   4860
attcaaatat gtatccgctc atgagacaat aaccctgata aatgcttcaa taatattgaa   4920
aaaggaagag tcctgaggcg gaaagaacca gctgtggaat gtgtgtcagt tagggtgtgg   4980
aaagtcccca ggctccccag caggcagaag tatgcaaagc atgcatctca attagtcagc   5040
aaccaggtgt ggaaagtccc caggctcccc agcaggcaga agtatgcaaa gcatgcatct   5100
caattagtca gcaaccatag tcccgcccct aactccgccc atcccgcccc taactccgcc   5160
cagttccgcc cattctccgc cccatggctg actaattttt tttatttatg cagaggccga   5220
ggccgcctcg gcctctgagc tattccagaa gtagtgagga ggcttttttg gaggcctagg   5280
cttttgcaaa gatcgatcaa gagacaggat gaggatcgtt tcgcatgatt gaacaagatg   5340
gattgcacgc aggttctccg gccgcttggg tggagaggct attcggctat gactgggcac   5400
aacagacaat cggctgctct gatgccgccg tgttccggct gtcagcgcag gggcgcccgg   5460
ttctttttgt caagaccgac ctgtccggtg ccctgaatga actgcaagac gaggcagcgc   5520
ggctatcgtg gctggccacg acgggcgttc cttgcgcagc tgtgctcgac gttgtcactg   5580
aagcgggaag ggactggctg ctattgggcg aagtgccggg gcaggatctc ctgtcatctc   5640
accttgctcc tgccgagaaa gtatccatca tggctgatgc aatgcggcgg ctgcatacgc   5700
ttgatccggc tacctgccca ttcgaccacc aagcgaaaca tcgcatcgag cgagcacgta   5760
ctcggatgga agccggtctt gtcgatcagg atgatctgga cgaagagcat caggggctcg   5820
cgccagccga actgttcgcc aggctcaagg cgagcatgcc cgacggcgag gatctcgtcg   5880
tgacccatgg cgatgcctgc ttgccgaata tcatggtgga aaatggccgc ttttctggat   5940
tcatcgactg tggccggctg ggtgtggcgg accgctatca ggacatagcg ttggctaccc   6000
gtgatattgc tgaagagctt ggcggcgaat gggctgaccg cttcctcgtg ctttacggta   6060
tcgccgctcc cgattcgcag cgcatcgcct tctatcgcct tcttgacgag ttcttctgag   6120
cgggactctg gggttcgaaa tgaccgacca agcgacgccc aacctgccat cacgagattt   6180
cgattccacc gccgccttct atgaaaggtt gggcttcgga atcgttttcc gggacgccgg   6240
ctggatgatc ctccagcgcg gggatctcat gctggagttc ttcgcccacc ctagggggag   6300
```

gctaactgaa acacggaagg agacaatacc ggaaggaacc cgcgctatga cggcaataaa 6360
aagacagaat aaaacgcacg gtgttgggtc gtttgttcat aaacgcgggg ttcggtccca 6420
gggctggcac tctgtcgata ccccaccgag accccattgg ggccaatacg cccgcgtttc 6480
ttccttttcc ccaccccacc ccccaagttc gggtgaaggc ccagggctcg cagccaacgt 6540
cggggcggca ggccctgcca tagcctcagg ttactcatat atactttaga ttgatttaaa 6600
acttcatttt taatttaaaa ggatctaggt gaagatcctt tttgataatc tcatgaccaa 6660
aatcccttaa cgtgagtttt cgttccactg agcgtcagac cccgtagaaa agatcaaagg 6720
atcttcttga gatccttttt ttctgcgcgt aatctgctgc ttgcaaacaa aaaaaccacc 6780
gctaccagcg gtggtttgtt tgccggatca agagctacca actctttttc cgaaggtaac 6840
tggcttcagc agagcgcaga taccaaatac tgtccttcta gtgtagccgt agttaggcca 6900
ccacttcaag aactctgtag caccgcctac atacctcgct ctgctaatcc tgttaccagt 6960
ggctgctgcc agtggcgata agtcgtgtct taccgggttg gactcaagac gatagttacc 7020
ggataaggcg cagcggtcgg gctgaacggg gggttcgtgc acacagccca gcttggagcg 7080
aacgacctac accgaactga gatacctaca gcgtgagcta tgagaaagcg ccacgcttcc 7140
cgaagggaga aaggcggaca ggtatccggt aagcggcagg gtcggaacag gagagcgcac 7200
gagggagctt ccagggggaa acgcctggta tctttatagt cctgtcgggt ttcgccacct 7260
ctgacttgag cgtcgatttt tgtgatgctc gtcagggggg cggagcctat ggaaaaacgc 7320
cagcaacgcg gcctttttac ggttcctggc cttttgctgg ccttttgctc acatgttctt 7380
tcctgcgtta tcccctgatt ctgtggataa ccgtattacc gccatgcat 7429

<210> SEQ ID NO 32
<211> LENGTH: 1149
<212> TYPE: PRT
<213> ORGANISM: Artificial Sequence
<220> FEATURE:
<223> OTHER INFORMATION: ASK1(I) YFP fusion protein sequence

<400> SEQUENCE: 32

Met Ser Thr Glu Ala Asp Glu Gly Ile Thr Phe Ser Val Pro Pro Phe
1 5 10 15

Ala Pro Ser Gly Phe Cys Thr Ile Pro Glu Gly Gly Ile Cys Arg Arg
20 25 30

Gly Gly Ala Ala Ala Val Gly Glu Gly Glu Glu His Gln Leu Pro Pro
35 40 45

Pro Pro Pro Gly Ser Phe Trp Asn Val Glu Ser Ala Ala Ala Pro Gly
50 55 60

Ile Gly Cys Pro Ala Ala Thr Ser Ser Ser Ser Ala Thr Arg Gly Arg
65 70 75 80

Gly Ser Ser Val Gly Gly Gly Ser Arg Arg Thr Thr Val Ala Tyr Val
85 90 95

Ile Asn Glu Ala Ser Gln Gly Gln Leu Val Val Ala Glu Ser Glu Ala
100 105 110

Leu Gln Ser Leu Arg Glu Ala Cys Glu Thr Val Gly Ala Thr Leu Glu
115 120 125

Thr Leu His Phe Gly Lys Leu Asp Phe Gly Glu Thr Thr Val Leu Asp
130 135 140

Arg Phe Tyr Asn Ala Asp Ile Ala Val Val Glu Met Ser Asp Ala Phe
145 150 155 160

Arg Gln Pro Ser Leu Phe Tyr His Leu Gly Val Arg Glu Ser Phe Ser

-continued

```
                165                 170                 175

Met Ala Asn Asn Ile Ile Leu Tyr Cys Asp Thr Asn Ser Asp Ser Leu
            180                 185                 190

Gln Ser Leu Lys Glu Ile Ile Cys Gln Lys Asn Thr Met Cys Thr Gly
        195                 200                 205

Asn Tyr Thr Phe Val Pro Tyr Met Ile Thr Pro His Asn Lys Val Tyr
    210                 215                 220

Cys Cys Asp Ser Ser Phe Met Lys Gly Leu Thr Glu Leu Met Gln Pro
225                 230                 235                 240

Asn Phe Glu Leu Leu Leu Gly Pro Ile Cys Leu Pro Leu Val Asp Arg
                245                 250                 255

Phe Ile Gln Leu Leu Lys Val Ala Gln Ala Ser Ser Ser Gln Tyr Phe
            260                 265                 270

Arg Glu Ser Ile Leu Asn Asp Ile Arg Lys Ala Arg Asn Leu Tyr Thr
        275                 280                 285

Gly Lys Glu Leu Ala Ala Glu Leu Ala Arg Ile Arg Gln Arg Val Asp
    290                 295                 300

Asn Ile Glu Val Leu Thr Ala Asp Ile Val Ile Asn Leu Leu Leu Ser
305                 310                 315                 320

Tyr Arg Asp Ile Gln Asp Tyr Asp Ser Ile Val Lys Leu Val Glu Thr
                325                 330                 335

Leu Glu Lys Leu Pro Thr Phe Asp Leu Ala Ser His His His Val Lys
            340                 345                 350

Phe His Tyr Ala Phe Ala Leu Asn Arg Arg Asn Leu Pro Gly Asp Arg
        355                 360                 365

Ala Lys Ala Leu Asp Ile Met Ile Pro Met Val Gln Ser Glu Gly Gln
    370                 375                 380

Val Ala Ser Asp Met Tyr Cys Leu Val Gly Arg Ile Tyr Lys Asp Met
385                 390                 395                 400

Phe Leu Asp Ser Asn Phe Thr Asp Thr Glu Ser Arg Asp His Gly Ala
                405                 410                 415

Ser Trp Phe Lys Lys Ala Phe Glu Ser Glu Pro Thr Leu Gln Ser Gly
            420                 425                 430

Ile Asn Tyr Ala Val Leu Leu Leu Ala Ala Gly His Gln Phe Glu Ser
        435                 440                 445

Ser Phe Glu Leu Arg Lys Val Gly Val Lys Leu Ser Ser Leu Leu Gly
    450                 455                 460

Lys Lys Gly Asn Leu Glu Lys Leu Gln Ser Tyr Trp Glu Val Gly Phe
465                 470                 475                 480

Phe Leu Gly Ala Ser Val Leu Ala Asn Asp His Met Arg Val Ile Gln
                485                 490                 495

Ala Ser Glu Lys Leu Phe Lys Leu Lys Thr Pro Ala Trp Tyr Leu Lys
            500                 505                 510

Ser Ile Val Glu Thr Ile Leu Ile Tyr Lys His Phe Val Lys Leu Thr
        515                 520                 525

Thr Glu Gln Pro Val Ala Lys Gln Glu Leu Val Asp Phe Trp Met Asp
    530                 535                 540

Phe Leu Val Glu Ala Thr Lys Thr Asp Val Thr Val Val Arg Phe Pro
545                 550                 555                 560

Val Leu Ile Leu Glu Pro Thr Lys Ile Tyr Gln Pro Ser Tyr Leu Ser
                565                 570                 575

Ile Asn Asn Glu Val Glu Glu Lys Thr Ile Ser Ile Trp His Val Leu
            580                 585                 590
```

-continued

```
Pro Asp Asp Lys Lys Gly Ile His Glu Trp Asn Phe Ser Ala Ser Ser
        595                 600                 605

Val Arg Gly Val Ser Ile Ser Lys Phe Glu Glu Arg Cys Cys Phe Leu
    610                 615                 620

Tyr Val Leu His Asn Ser Asp Asp Phe Gln Ile Tyr Phe Cys Thr Glu
625                 630                 635                 640

Leu His Cys Lys Lys Phe Phe Glu Met Val Asn Thr Ile Thr Glu Glu
                645                 650                 655

Lys Gly Arg Ser Thr Glu Glu Gly Asp Cys Glu Ser Asp Leu Leu Glu
            660                 665                 670

Tyr Asp Tyr Glu Tyr Asp Glu Asn Gly Asp Arg Val Val Leu Gly Lys
        675                 680                 685

Gly Thr Tyr Gly Ile Val Tyr Ala Gly Arg Asp Leu Ser Asn Gln Val
    690                 695                 700

Arg Ile Ala Ile Lys Glu Ile Pro Glu Arg Asp Ser Arg Tyr Ser Gln
705                 710                 715                 720

Pro Leu His Glu Glu Ile Ala Leu His Lys His Leu Lys His Lys Asn
                725                 730                 735

Ile Val Gln Tyr Leu Gly Ser Phe Ser Glu Asn Gly Phe Ile Lys Ile
            740                 745                 750

Phe Met Glu Gln Val Pro Gly Gly Ser Leu Ser Ala Leu Leu Arg Ser
        755                 760                 765

Lys Trp Gly Pro Leu Lys Asp Asn Glu Gln Thr Ile Gly Phe Tyr Thr
    770                 775                 780

Lys Gln Ile Leu Glu Gly Leu Lys Tyr Leu His Asp Asn Gln Ile Val
785                 790                 795                 800

His Arg Asp Ile Lys Gly Asp Asn Val Leu Ile Asn Thr Tyr Ser Gly
                805                 810                 815

Val Leu Lys Ile Ser Asp Phe Gly Thr Ser Lys Arg Leu Ala Gly Ile
            820                 825                 830

Asn Pro Cys Thr Glu Thr Phe Thr Gly Thr Leu Gln Tyr Met Ala Pro
        835                 840                 845

Glu Ile Ile Asp Lys Gly Pro Arg Gly Tyr Gly Lys Ala Ala Asp Ile
    850                 855                 860

Trp Ser Leu Gly Cys Thr Ile Ile Glu Met Ala Thr Gly Lys Pro Pro
865                 870                 875                 880

Phe Tyr Glu Leu Gly Glu Pro Gln Ala Ala Met Phe Lys Val Gly Met
                885                 890                 895

Phe Lys Val His Pro Glu Ile Arg Asp Pro Pro Val Ala Thr Met Val
            900                 905                 910

Ser Lys Gly Glu Glu Leu Phe Thr Gly Val Val Pro Ile Leu Val Glu
        915                 920                 925

Leu Asp Gly Asp Val Asn Gly His Lys Phe Ser Val Ser Gly Glu Gly
    930                 935                 940

Glu Gly Asp Ala Thr Tyr Gly Lys Leu Thr Leu Lys Phe Ile Cys Thr
945                 950                 955                 960

Thr Gly Lys Leu Pro Val Pro Trp Pro Thr Leu Val Thr Thr Phe Gly
                965                 970                 975

Tyr Gly Leu Gln Cys Phe Ala Arg Tyr Pro Asp His Met Lys Gln His
            980                 985                 990

Asp Phe Phe Lys Ser Ala Met Pro  Glu Gly Tyr Val Gln  Glu Arg Thr
        995                 1000                 1005
```

-continued

```
Ile Phe  Phe Lys Asp Asp Gly  Asn Tyr Lys Thr Arg  Ala Glu Val
    1010                 1015                 1020

Lys Phe  Glu Gly Asp Thr Leu  Val Asn Arg Ile Glu  Leu Lys Gly
    1025                 1030                 1035

Ile Asp  Phe Lys Glu Asp Gly  Asn Ile Leu Gly His  Lys Leu Glu
    1040                 1045                 1050

Tyr Asn  Tyr Asn Ser His Asn  Val Tyr Ile Met Ala  Asp Lys Gln
    1055                 1060                 1065

Lys Asn  Gly Ile Lys Val Asn  Phe Lys Ile Arg His  Asn Ile Glu
    1070                 1075                 1080

Asp Gly  Ser Val Gln Leu Ala  Asp His Tyr Gln Gln  Asn Thr Pro
    1085                 1090                 1095

Ile Gly  Asp Gly Pro Val Leu  Leu Pro Asp Asn His  Tyr Leu Ser
    1100                 1105                 1110

Tyr Gln  Ser Ala Leu Ser Lys  Asp Pro Asn Glu Lys  Arg Asp His
    1115                 1120                 1125

Met Val  Leu Leu Glu Phe Val  Thr Ala Ala Gly Ile  Thr Leu Gly
    1130                 1135                 1140

Met Asp  Glu Leu Tyr Lys
    1145
```

<210> SEQ ID NO 33
<211> LENGTH: 6478
<212> TYPE: DNA
<213> ORGANISM: Artificial Sequence
<220> FEATURE:
<223> OTHER INFORMATION: construct Sequence containing ASK (J) cloned in pEYFP

<400> SEQUENCE: 33

```
tagttattaa tagtaatcaa ttacggggtc attagttcat agcccatata tggagttccg     60

cgttacataa cttacggtaa atggcccgcc tggctgaccg cccaacgacc cccgcccatt    120

gacgtcaata atgacgtatg ttcccatagt aacgccaata gggactttcc attgacgtca    180

atgggtggag tatttacggt aaactgccca cttggcagta catcaagtgt atcatatgcc    240

aagtacgccc cctattgacg tcaatgacgg taaatggccc gcctggcatt atgcccagta    300

catgacctta tgggactttc ctacttggca gtacatctac gtattagtca tcgctattac    360

catggtgatg cggttttggc agtacatcaa tgggcgtgga tagcggtttg actcacgggg    420

atttccaagt ctccacccca ttgacgtcaa tgggagtttg ttttggcacc aaaatcaacg    480

ggactttcca aaatgtcgta acaactccgc cccattgacg caaatgggcg gtaggcgtgt    540

acggtgggag gtctatataa gcagagctgg tttagtgaac cgtcagatcc gctagcgcta    600

ccggactcag atctcgagct caagcttcga attctgcagt cgacatgctt tcctacagag    660

atatccagga ctatgattct attgtgaagc tggtagagac tttagaaaaa ctgccaacct    720

ttgatttggc ctcccatcac catgtgaagt ttcattatgc atttgcactg aataggagaa    780

atctccctgg tgacagagca aaagctcttg atattatgat tcccatggtg caaagcgaag    840

gacaagttgc ttcagatatg tattgcctag ttggtcgaat ctacaaagat atgtttttgg    900

actctaattt cacggacact gaaagcagag accatggagc ttcttggttc aaaaaggcat    960

ttgaatctga gccaacacta cagtcaggaa ttaattatgc ggtcctcctc ctggcagctg   1020

gacaccagtt tgaatcttcc tttgagctcc ggaaagttgg ggtgaagcta agtagtcttc   1080

ttggtaaaaa gggaaacttg gaaaaactcc agagctactg ggaagttgga tttttctgg   1140
```

-continued

```
gggccagcgt cctagccaat gaccacatga gagtcattca agcatctgaa aagcttttta   1200
aactgaagac accagcatgg tacctcaagt ctattgtaga gacaatttta atatataagc   1260
attttgtgaa actgaccaca gaacagcctg tggccaagca agaacttgtg gacttttgga   1320
tggatttcct ggtcgaggcc acaaagacag atgttactgt ggttaggttt ccagtattaa   1380
tattagaacc aaccaaaatc tatcaacctt cttatttgtc tatcaacaat gaagttgagg   1440
aaaagacaat ctctatttgg cacgtgcttc ctgatgacaa gaaaggtata catgagtgga   1500
attttagtgc ctcttctgtc aggggagtga gtatttctaa atttgaagaa agatgctgct   1560
ttctttatgt gcttcacaat tctgatgatt tccaaatcta tttctgtaca gaacttcatt   1620
gtaaaaagtt ttttgagatg gtgaacacca ttaccgaaga gaaggggaga agcacagagg   1680
aaggagactg tgaaagtgac ttgctggagt atgactatga atatgatgaa aatggtgaca   1740
gagtcgtttt aggaaaaggc acttatggga tagtctacgc aggtcgggac ttgagcaacc   1800
aagtcagaat tgctattaag gaaatcccag agagagacag cagatactct cagcccctgc   1860
atgaagaaat agcattgcat aaacacctga agcacaaaaa tattgtccag tatctgggct   1920
ctttcagtga gaatggtttc attaaaatct tcatggagca ggtccctgga ggaagtcttt   1980
ctgctctcct tcgttccaaa tggggtccat taaaagacaa tgagcaaaca attggctttt   2040
atacaaagca aatactggaa ggattaaaat atctccatga caatcagata gttcaccggg   2100
acataaaggg tgacaatgtg ttgattaata cctacagtgg tgttctcaag atctctgact   2160
tcggaacatc aaagaggctt gctggcataa acccctgtac tgaaactttt actggtaccc   2220
tccagtatat ggcaccagaa ataatagata aaggaccaag aggctacgga aaagcagcag   2280
acatctggtc tctgggctgt acaatcattg aaatggccac aggaaaaccc ccattttatg   2340
aactgggaga accacaagca gctatgttca aggtgggaat gtttaaagtc caccctgaga   2400
tccgggatcc accggtcgcc accatggtga gcaagggcga ggagctgttc accggggtgg   2460
tgcccatcct ggtcgagctg gacggcgacg taaacggcca caagttcagc gtgtccggcg   2520
agggcgaggg cgatgccacc tacggcaagc tgaccctgaa gttcatctgc accaccggca   2580
agctgcccgt gccctggccc accctcgtga ccaccttcgg ctacggcctg cagtgcttcg   2640
cccgctaccc cgaccacatg aagcagcacg acttcttcaa gtccgccatg cccgaaggct   2700
acgtccagga gcgcaccatc ttcttcaagg acgacggcaa ctacaagacc cgcgccgagg   2760
tgaagttcga gggcgacacc ctggtgaacc gcatcgagct gaagggcatc gacttcaagg   2820
aggacggcaa catcctgggg cacaagctgg agtacaacta caacagccac aacgtctata   2880
tcatggccga caagcagaag aacggcatca aggtgaactt caagatccgc cacaacatcg   2940
aggacggcag cgtgcagctc gccgaccact accagcagaa cacccccatc ggcgacggcc   3000
ccgtgctgct gcccgacaac cactacctga gctaccagtc cgccctgagc aaagacccca   3060
acgagaagcg cgatcacatg gtcctgctgg agttcgtgac cgccgccggg atcactctcg   3120
gcatggacga gctgtacaag taaagcggcc gcgactctag atcataatca gccataccac   3180
atttgtagag gttttacttg ctttaaaaaa cctcccacac ctccccctga acctgaaaca   3240
taaaatgaat gcaattgttg ttgttaactt gtttattgca gcttataatg gttacaaata   3300
aagcaatagc atcacaaatt tcacaaataa agcatttttt tcactgcatt ctagttgtgg   3360
tttgtccaaa ctcatcaatg tatcttaagg cgtaaattgt aagcgttaat attttgttaa   3420
aattcgcgtt aaatttttgt taaatcagct cattttttaa ccaataggcc gaaatcggca   3480
aaatccctta taaatcaaaa gaatagaccg agatagggtt gagtgttgtt ccagtttgga   3540
```

```
acaagagtcc actattaaag aacgtggact ccaacgtcaa agggcgaaaa accgtctatc   3600
agggcgatgg cccactacgt gaaccatcac cctaatcaag ttttttgggg tcgaggtgcc   3660
gtaaagcact aaatcggaac cctaaaggga gcccccgatt tagagcttga cggggaaagc   3720
cggcgaacgt ggcgagaaag gaagggaaga aagcgaaagg agcgggcgct agggcgctgg   3780
caagtgtagc ggtcacgctg cgcgtaacca ccacacccgc cgcgcttaat gcgccgctac   3840
agggcgcgtc aggtggcact tttcggggaa atgtgcgcgg aacccctatt tgtttatttt   3900
tctaaataca ttcaaatatg tatccgctca tgagacaata accctgataa atgcttcaat   3960
aatattgaaa aaggaagagt cctgaggcgg aaagaaccag ctgtggaatg tgtgtcagtt   4020
agggtgtgga aagtccccag gctccccagc aggcagaagt atgcaaagca tgcatctcaa   4080
ttagtcagca accaggtgtg gaaagtcccc aggctcccca gcaggcagaa gtatgcaaag   4140
catgcatctc aattagtcag caaccatagt cccgccccta actccgccca tcccgcccct   4200
aactccgccc agttccgccc attctccgcc ccatggctga ctaatttttt ttatttatgc   4260
agaggccgag gccgcctcgg cctctgagct attccagaag tagtgaggag gcttttttgg   4320
aggcctaggc ttttgcaaag atcgatcaag agacaggatg aggatcgttt cgcatgattg   4380
aacaagatgg attgcacgca ggttctccgg ccgcttgggt ggagaggcta ttcggctatg   4440
actgggcaca acagacaatc ggctgctctg atgccgccgt gttccggctg tcagcgcagg   4500
ggcgcccggt tctttttgtc aagaccgacc tgtccggtgc cctgaatgaa ctgcaagacg   4560
aggcagcgcg gctatcgtgg ctggccacga cgggcgttcc ttgcgcagct gtgctcgacg   4620
ttgtcactga agcgggaagg gactggctgc tattgggcga agtgccgggg caggatctcc   4680
tgtcatctca ccttgctcct gccgagaaag tatccatcat ggctgatgca atgcggcggc   4740
tgcatacgct tgatccggct acctgcccat tcgaccacca agcgaaacat cgcatcgagc   4800
gagcacgtac tcggatggaa gccggtcttg tcgatcagga tgatctggac gaagagcatc   4860
aggggctcgc gccagccgaa ctgttcgcca ggctcaaggc gagcatgccc gacggcgagg   4920
atctcgtcgt gacccatggc gatgcctgct tgccgaatat catggtggaa aatggccgct   4980
tttctggatt catcgactgt ggccggctgg gtgtggcgga ccgctatcag gacatagcgt   5040
tggctacccg tgatattgct gaagagcttg gcggcgaatg ggctgaccgc ttcctcgtgc   5100
tttacggtat cgccgctccc gattcgcagc gcatcgcctt ctatcgcctt cttgacgagt   5160
tcttctgagc gggactctgg ggttcgaaat gaccgaccaa gcgacgccca acctgccatc   5220
acgagatttc gattccaccg ccgccttcta tgaaaggttg ggcttcggaa tcgttttccg   5280
ggacgccggc tggatgatcc tccagcgcgg ggatctcatg ctggagttct tcgcccaccc   5340
taggggagg ctaactgaaa cacggaagga gacaataccg gaaggaaccc gcgctatgac   5400
ggcaataaaa agacagaata aaacgcacgg tgttgggtcg tttgttcata aacgcggggt   5460
tcggtcccag ggctggcact ctgtcgatac cccaccgaga ccccattggg gccaatacgc   5520
ccgcgtttct tccttttccc caccccaccc cccaagttcg ggtgaaggcc cagggctcgc   5580
agccaacgtc ggggcggcag gccctgccat agcctcaggt tactcatata tactttagat   5640
tgatttaaaa cttcattttt aatttaaaag gatctaggtg aagatccttt ttgataatct   5700
catgaccaaa atcccttaac gtgagttttc gttccactga gcgtcagacc ccgtagaaaa   5760
gatcaaagga tcttcttgag atcctttttt tctgcgcgta atctgctgct tgcaaacaaa   5820
aaaaccaccg ctaccagcgg tggtttgttt gccggatcaa gagctaccaa ctctttttcc   5880
```

gaaggtaact ggcttcagca gagcgcagat accaaatact gtccttctag tgtagccgta 5940
gttaggccac cacttcaaga actctgtagc accgcctaca tacctcgctc tgctaatcct 6000
gttaccagtg gctgctgcca gtggcgataa gtcgtgtctt accgggttgg actcaagacg 6060
atagttaccg gataaggcgc agcggtcggg ctgaacgggg ggttcgtgca cacagcccag 6120
cttggagcga acgacctaca ccgaactgag atacctacag cgtgagctat gagaaagcgc 6180
cacgcttccc gaagggagaa aggcggacag gtatccggta agcggcaggg tcggaacagg 6240
agagcgcacg agggagcttc cagggggaaa cgcctggtat ctttatagtc ctgtcgggtt 6300
tcgccacctc tgacttgagc gtcgattttt gtgatgctcg tcaggggggc ggagcctatg 6360
gaaaaacgcc agcaacgcgg cctttttacg gttcctggcc ttttgctggc cttttgctca 6420
catgttcttt cctgcgttat cccctgattc tgtggataac cgtattaccg ccatgcat 6478

<210> SEQ ID NO 34
<211> LENGTH: 832
<212> TYPE: PRT
<213> ORGANISM: Artificial Sequence
<220> FEATURE:
<223> OTHER INFORMATION: ASK1(j) YFP fusion protein sequence

<400> SEQUENCE: 34

```
Met Leu Ser Tyr Arg Asp Ile Gln Asp Tyr Asp Ser Ile Val Lys Leu
1               5                   10                  15

Val Glu Thr Leu Glu Lys Leu Pro Thr Phe Asp Leu Ala Ser His His
            20                  25                  30

His Val Lys Phe His Tyr Ala Phe Ala Leu Asn Arg Arg Asn Leu Pro
        35                  40                  45

Gly Asp Arg Ala Lys Ala Leu Asp Ile Met Ile Pro Met Val Gln Ser
    50                  55                  60

Glu Gly Gln Val Ala Ser Asp Met Tyr Cys Leu Val Gly Arg Ile Tyr
65                  70                  75                  80

Lys Asp Met Phe Leu Asp Ser Asn Phe Thr Asp Thr Glu Ser Arg Asp
                85                  90                  95

His Gly Ala Ser Trp Phe Lys Lys Ala Phe Glu Ser Glu Pro Thr Leu
            100                 105                 110

Gln Ser Gly Ile Asn Tyr Ala Val Leu Leu Leu Ala Ala Gly His Gln
        115                 120                 125

Phe Glu Ser Ser Phe Glu Leu Arg Lys Val Gly Val Lys Leu Ser Ser
    130                 135                 140

Leu Leu Gly Lys Lys Gly Asn Leu Glu Lys Leu Gln Ser Tyr Trp Glu
145                 150                 155                 160

Val Gly Phe Phe Leu Gly Ala Ser Val Leu Ala Asn Asp His Met Arg
                165                 170                 175

Val Ile Gln Ala Ser Glu Lys Leu Phe Lys Leu Lys Thr Pro Ala Trp
            180                 185                 190

Tyr Leu Lys Ser Ile Val Glu Thr Ile Leu Ile Tyr Lys His Phe Val
        195                 200                 205

Lys Leu Thr Thr Glu Gln Pro Val Ala Lys Gln Glu Leu Val Asp Phe
    210                 215                 220

Trp Met Asp Phe Leu Val Glu Ala Thr Lys Thr Asp Val Thr Val Val
225                 230                 235                 240

Arg Phe Pro Val Leu Ile Leu Glu Pro Thr Lys Ile Tyr Gln Pro Ser
                245                 250                 255

Tyr Leu Ser Ile Asn Asn Glu Val Glu Glu Lys Thr Ile Ser Ile Trp
```

-continued

```
            260                 265                 270

His Val Leu Pro Asp Asp Lys Lys Gly Ile His Glu Trp Asn Phe Ser
        275                 280                 285

Ala Ser Ser Val Arg Gly Val Ser Ile Ser Lys Phe Glu Glu Arg Cys
    290                 295                 300

Cys Phe Leu Tyr Val Leu His Asn Ser Asp Asp Phe Gln Ile Tyr Phe
305                 310                 315                 320

Cys Thr Glu Leu His Cys Lys Lys Phe Phe Glu Met Val Asn Thr Ile
                325                 330                 335

Thr Glu Glu Lys Gly Arg Ser Thr Glu Glu Gly Asp Cys Glu Ser Asp
            340                 345                 350

Leu Leu Glu Tyr Asp Tyr Glu Tyr Asp Glu Asn Gly Asp Arg Val Val
        355                 360                 365

Leu Gly Lys Gly Thr Tyr Gly Ile Val Tyr Ala Gly Arg Asp Leu Ser
    370                 375                 380

Asn Gln Val Arg Ile Ala Ile Lys Glu Ile Pro Glu Arg Asp Ser Arg
385                 390                 395                 400

Tyr Ser Gln Pro Leu His Glu Glu Ile Ala Leu His Lys His Leu Lys
                405                 410                 415

His Lys Asn Ile Val Gln Tyr Leu Gly Ser Phe Ser Glu Asn Gly Phe
            420                 425                 430

Ile Lys Ile Phe Met Glu Gln Val Pro Gly Gly Ser Leu Ser Ala Leu
        435                 440                 445

Leu Arg Ser Lys Trp Gly Pro Leu Lys Asp Asn Glu Gln Thr Ile Gly
    450                 455                 460

Phe Tyr Thr Lys Gln Ile Leu Glu Gly Leu Lys Tyr Leu His Asp Asn
465                 470                 475                 480

Gln Ile Val His Arg Asp Ile Lys Gly Asp Asn Val Leu Ile Asn Thr
                485                 490                 495

Tyr Ser Gly Val Leu Lys Ile Ser Asp Phe Gly Thr Ser Lys Arg Leu
            500                 505                 510

Ala Gly Ile Asn Pro Cys Thr Glu Thr Phe Thr Gly Thr Leu Gln Tyr
        515                 520                 525

Met Ala Pro Glu Ile Ile Asp Lys Gly Pro Arg Gly Tyr Gly Lys Ala
    530                 535                 540

Ala Asp Ile Trp Ser Leu Gly Cys Thr Ile Ile Glu Met Ala Thr Gly
545                 550                 555                 560

Lys Pro Pro Phe Tyr Glu Leu Gly Glu Pro Gln Ala Ala Met Phe Lys
                565                 570                 575

Val Gly Met Phe Lys Val His Pro Glu Ile Arg Asp Pro Pro Val Ala
            580                 585                 590

Thr Met Val Ser Lys Gly Glu Glu Leu Phe Thr Gly Val Val Pro Ile
        595                 600                 605

Leu Val Glu Leu Asp Gly Asp Val Asn Gly His Lys Phe Ser Val Ser
    610                 615                 620

Gly Glu Gly Glu Gly Asp Ala Thr Tyr Gly Lys Leu Thr Leu Lys Phe
625                 630                 635                 640

Ile Cys Thr Thr Gly Lys Leu Pro Val Pro Trp Pro Thr Leu Val Thr
                645                 650                 655

Thr Phe Gly Tyr Gly Leu Gln Cys Phe Ala Arg Tyr Pro Asp His Met
            660                 665                 670

Lys Gln His Asp Phe Phe Lys Ser Ala Met Pro Glu Gly Tyr Val Gln
        675                 680                 685
```

-continued

```
Glu Arg Thr Ile Phe Phe Lys Asp Asp Gly Asn Tyr Lys Thr Arg Ala
    690                 695                 700

Glu Val Lys Phe Glu Gly Asp Thr Leu Val Asn Arg Ile Glu Leu Lys
705                 710                 715                 720

Gly Ile Asp Phe Lys Glu Asp Gly Asn Ile Leu Gly His Lys Leu Glu
                725                 730                 735

Tyr Asn Tyr Asn Ser His Asn Val Tyr Ile Met Ala Asp Lys Gln Lys
            740                 745                 750

Asn Gly Ile Lys Val Asn Phe Lys Ile Arg His Asn Ile Glu Asp Gly
        755                 760                 765

Ser Val Gln Leu Ala Asp His Tyr Gln Gln Asn Thr Pro Ile Gly Asp
    770                 775                 780

Gly Pro Val Leu Leu Pro Asp Asn His Tyr Leu Ser Tyr Gln Ser Ala
785                 790                 795                 800

Leu Ser Lys Asp Pro Asn Glu Lys Arg Asp His Met Val Leu Leu Glu
                805                 810                 815

Phe Val Thr Ala Ala Gly Ile Thr Leu Gly Met Asp Glu Leu Tyr Lys
            820                 825                 830


<210> SEQ ID NO 35
<211> LENGTH: 30
<212> TYPE: DNA
<213> ORGANISM: Artificial Sequence
<220> FEATURE:
<223> OTHER INFORMATION: Forward Primer N1: HIV-1 nef gene cloned in
      VP16pcDNA+pACT

<400> SEQUENCE: 35

catggatccg tggagcactt acaagcagca                                        30


<210> SEQ ID NO 36
<211> LENGTH: 31
<212> TYPE: DNA
<213> ORGANISM: Artificial Sequence
<220> FEATURE:
<223> OTHER INFORMATION: Reverse Primer N1: HIV-1 nef gene cloned in
      VP16pcDNA+pACT

<400> SEQUENCE: 36

catggatcct cagcagtctt tgtaatactc c                                      31


<210> SEQ ID NO 37
<211> LENGTH: 33
<212> TYPE: DNA
<213> ORGANISM: Artificial Sequence
<220> FEATURE:
<223> OTHER INFORMATION: Forward Primer 1: ASK1(a) gene cloned in pBIND

<400> SEQUENCE: 37

agcggatccg tacggaggcg gacgagggca tca                                    33


<210> SEQ ID NO 38
<211> LENGTH: 28
<212> TYPE: DNA
<213> ORGANISM: Artificial Sequence
<220> FEATURE:
<223> OTHER INFORMATION: Reverse Primer 1: ASK1(a) gene cloned in pBIND

<400> SEQUENCE: 38

agcgtctaga caaatcaaag gttggcag                                          28
```

<210> SEQ ID NO 39
<211> LENGTH: 32
<212> TYPE: DNA
<213> ORGANISM: Artificial Sequence
<220> FEATURE:
<223> OTHER INFORMATION: Forward Primer 2: ASK1(b) gene cloned in pBIND

<400> SEQUENCE: 39
agcggatccg ttcctacaga gatatccagg ac 32

<210> SEQ ID NO 40
<211> LENGTH: 30
<212> TYPE: DNA
<213> ORGANISM: Artificial Sequence
<220> FEATURE:
<223> OTHER INFORMATION: Reverse Primer 2: ASK1(b) gene cloned in pBIND

<400> SEQUENCE: 40
agcgtctaga caagtcactt tcacagtctc 30

<210> SEQ ID NO 41
<211> LENGTH: 30
<212> TYPE: DNA
<213> ORGANISM: Artificial Sequence
<220> FEATURE:
<223> OTHER INFORMATION: Forward Primer 3: ASK1(c) gene cloned in pBIND

<400> SEQUENCE: 41
agcggatccg ttcttctgtc aggggagtga 30

<210> SEQ ID NO 42
<211> LENGTH: 28
<212> TYPE: DNA
<213> ORGANISM: Artificial Sequence
<220> FEATURE:
<223> OTHER INFORMATION: Reverse Primer 3: ASK1(c) gene cloned in pBIND

<400> SEQUENCE: 42
agcgtctaga tgggatctca gggtggac 28

<210> SEQ ID NO 43
<211> LENGTH: 30
<212> TYPE: DNA
<213> ORGANISM: Artificial Sequence
<220> FEATURE:
<223> OTHER INFORMATION: Forward Primer 4: ASK1(d) gene cloned in pBIND

<400> SEQUENCE: 43
agcggatccg tgcagcagac atctggtctc 30

<210> SEQ ID NO 44
<211> LENGTH: 29
<212> TYPE: DNA
<213> ORGANISM: Artificial Sequence
<220> FEATURE:
<223> OTHER INFORMATION: Reverse Primer 3420: ASK1(d) gene cloned in pBIND

<400> SEQUENCE: 44
agcgtctaga actctcagat gcaaggctg 29

<210> SEQ ID NO 45
<211> LENGTH: 33
<212> TYPE: DNA
<213> ORGANISM: Artificial Sequence
<220> FEATURE:
<223> OTHER INFORMATION: Forward Primer 4: ASK1(e) gene cloned in pBIND

<400> SEQUENCE: 45
agcggatccg tgacagtatc attcggaagg cgg 33

<210> SEQ ID NO 46
<211> LENGTH: 31
<212> TYPE: DNA
<213> ORGANISM: Artificial Sequence
<220> FEATURE:
<223> OTHER INFORMATION: Reverse Primer 4: ASK1(e) gene cloned in pBIND

<400> SEQUENCE: 46
agcgtctaga gtcaatgata gccttccaca g 31

<210> SEQ ID NO 47
<211> LENGTH: 33
<212> TYPE: DNA
<213> ORGANISM: Artificial Sequence
<220> FEATURE:
<223> OTHER INFORMATION: Forward Primer 5: ASK1(f) gene cloned in pBIND

<400> SEQUENCE: 47
agcggatccg tacggaggcg gacgagggca tca 33

<210> SEQ ID NO 48
<211> LENGTH: 30
<212> TYPE: DNA
<213> ORGANISM: Artificial Sequence
<220> FEATURE:
<223> OTHER INFORMATION: Reverse Primer 5: ASK1(f) gene cloned in pBIND

<400> SEQUENCE: 48
agcgtctaga tcgcctctca ctgtccttcc 30

<210> SEQ ID NO 49
<211> LENGTH: 33
<212> TYPE: DNA
<213> ORGANISM: Artificial Sequence
<220> FEATURE:
<223> OTHER INFORMATION: Forward Primer 1: ASK1(g) gene cloned in pBIND

<400> SEQUENCE: 49
agcggatccg tacggaggcg gacgagggca tca 33

<210> SEQ ID NO 50
<211> LENGTH: 29
<212> TYPE: DNA
<213> ORGANISM: Artificial Sequence
<220> FEATURE:
<223> OTHER INFORMATION: Reverse Primer 3420: ASK1(g) gene cloned in pBIND

<400> SEQUENCE: 50
agcgtctaga actctcagat gcaaggctg 29

<210> SEQ ID NO 51
<211> LENGTH: 32
<212> TYPE: DNA
<213> ORGANISM: Artificial Sequence
<220> FEATURE:
<223> OTHER INFORMATION: Forward Primer 2: ASK1(h) gene cloned in pBIND

<400> SEQUENCE: 51
agcggatccg ttcctacaga gatatccagg ac 32

```
<210> SEQ ID NO 52
<211> LENGTH: 29
<212> TYPE: DNA
<213> ORGANISM: Artificial Sequence
<220> FEATURE:
<223> OTHER INFORMATION: Reverse Primer 3420: ASK1(h) gene cloned in
      pBIND

<400> SEQUENCE: 52

agcgtctaga actctcagat gcaaggctg                                    29


<210> SEQ ID NO 53
<211> LENGTH: 33
<212> TYPE: DNA
<213> ORGANISM: Artificial Sequence
<220> FEATURE:
<223> OTHER INFORMATION: Forward Primer 1: ASK1(i) gene cloned in pBIND

<400> SEQUENCE: 53

agcggatccg tacggaggcg gacgagggca tca                               33


<210> SEQ ID NO 54
<211> LENGTH: 28
<212> TYPE: DNA
<213> ORGANISM: Artificial Sequence
<220> FEATURE:
<223> OTHER INFORMATION: Reverse Primer 3: ASK1(i) gene cloned in pBIND

<400> SEQUENCE: 54

agcgtctaga tgggatctca gggtggac                                     28


<210> SEQ ID NO 55
<211> LENGTH: 32
<212> TYPE: DNA
<213> ORGANISM: Artificial Sequence
<220> FEATURE:
<223> OTHER INFORMATION: Forward Primer 2: ASK1(J) gene cloned in pBIND

<400> SEQUENCE: 55

agcggatccg ttcctacaga gatatccagg ac                                32


<210> SEQ ID NO 56
<211> LENGTH: 28
<212> TYPE: DNA
<213> ORGANISM: Artificial Sequence
<220> FEATURE:
<223> OTHER INFORMATION: Reverse Primer 3: ASK1(J) gene cloned in pBIND

<400> SEQUENCE: 56

agcgtctaga tgggatctca gggtggac                                     28


<210> SEQ ID NO 57
<211> LENGTH: 30
<212> TYPE: DNA
<213> ORGANISM: Artificial Sequence
<220> FEATURE:
<223> OTHER INFORMATION: Forward Primer 1: HIV-1 nef gene cloned in
      pEYFP-N1

<400> SEQUENCE: 57

agcaagctta tggggggcaa gtggtcaaaa                                   30


<210> SEQ ID NO 58
<211> LENGTH: 30
<212> TYPE: DNA
<213> ORGANISM: Artificial Sequence
<220> FEATURE:
```

-continued

<223> OTHER INFORMATION: Reverse Primer 1: HIV-1 nef gene cloned in pEYFP-N1

<400> SEQUENCE: 58
agcgtcgacg cgcagtcttt gtaaactccg 30

<210> SEQ ID NO 59
<211> LENGTH: 30
<212> TYPE: DNA
<213> ORGANISM: Artificial Sequence
<220> FEATURE:
<223> OTHER INFORMATION: Forward Primer 2: ASK1(g) cloned in pEYFP-N1

<400> SEQUENCE: 59
gtcgaatgag cacggaggcg acgagggcat 30

<210> SEQ ID NO 60
<211> LENGTH: 33
<212> TYPE: DNA
<213> ORGANISM: Artificial Sequence
<220> FEATURE:
<223> OTHER INFORMATION: Reverse Primer 2: ASK1(g) cloned in pEYFP-N1

<400> SEQUENCE: 60
ggatcccgcc tctcactgtc cttcctcagc atg 33

<210> SEQ ID NO 61
<211> LENGTH: 40
<212> TYPE: DNA
<213> ORGANISM: Artificial Sequence
<220> FEATURE:
<223> OTHER INFORMATION: Forward Primer 3: ASK1(h) cloned in pEYFP-N1

<400> SEQUENCE: 61
cgagcgtcga catgtcctac agagatatcc aggactatga 40

<210> SEQ ID NO 62
<211> LENGTH: 33
<212> TYPE: DNA
<213> ORGANISM: Artificial Sequence
<220> FEATURE:
<223> OTHER INFORMATION: Reverse Primer 3: ASK1(h) cloned in pEYFP-N1

<400> SEQUENCE: 62
ggatcccgcc tctcactgtc cttcctcagc atg 33

<210> SEQ ID NO 63
<211> LENGTH: 31
<212> TYPE: DNA
<213> ORGANISM: Artificial Sequence
<220> FEATURE:
<223> OTHER INFORMATION: Forward Primer 4: ASK1(i) cloned in pEYFP-N1

<400> SEQUENCE: 63
gtcgaatgag cacggaggcg gacgagggca t 31

<210> SEQ ID NO 64
<211> LENGTH: 31
<212> TYPE: DNA
<213> ORGANISM: Artificial Sequence
<220> FEATURE:
<223> OTHER INFORMATION: Reverse Primer 4: ASK1(i) cloned in pEYFP-N1

<400> SEQUENCE: 64
agcggatcct ctgggatctc agggtggact t 31

<210> SEQ ID NO 65
<211> LENGTH: 40
<212> TYPE: DNA
<213> ORGANISM: Artificial Sequence
<220> FEATURE:
<223> OTHER INFORMATION: Forward Primer 5: ASK1(J) cloned in pEYFP-N1

<400> SEQUENCE: 65
cgagcgtcga catgtcctac agagatatcc aggactatga 40

<210> SEQ ID NO 66
<211> LENGTH: 31
<212> TYPE: DNA
<213> ORGANISM: Artificial Sequence
<220> FEATURE:
<223> OTHER INFORMATION: Reverse Primer 5: ASK1(J) cloned in pEYFP-N1

<400> SEQUENCE: 66
agcggatcct ctgggatctc agggtggact t 31

<210> SEQ ID NO 67
<211> LENGTH: 9
<212> TYPE: PRT
<213> ORGANISM: Artificial Sequence
<220> FEATURE:
<223> OTHER INFORMATION: Peptide 1: Inhibitor reversing Nef-ASK1 effect

<400> SEQUENCE: 67

Thr Pro Gly Pro Gly Val Arg Tyr Pro
1 5

<210> SEQ ID NO 68
<211> LENGTH: 8
<212> TYPE: PRT
<213> ORGANISM: Artificial Sequence
<220> FEATURE:
<223> OTHER INFORMATION: Peptide 2: Inhibitor reversing Nef-ASK1 effect

<400> SEQUENCE: 68

Gly Glu Asn Asn Cys Leu Leu His
1 5

<210> SEQ ID NO 69
<211> LENGTH: 8
<212> TYPE: PRT
<213> ORGANISM: Artificial Sequence
<220> FEATURE:
<223> OTHER INFORMATION: Peptide 3: Inhibitor reversing Nef-ASK1 effect

<400> SEQUENCE: 69

Asp Glu Val Gly Glu Ala Asn Asn
1 5

<210> SEQ ID NO 70
<211> LENGTH: 8
<212> TYPE: PRT
<213> ORGANISM: Artificial Sequence
<220> FEATURE:
<223> OTHER INFORMATION: Peptide 4: Inhibitor reversing Nef-ASK1 effect

<400> SEQUENCE: 70

Leu His Gly Met Glu Asp Pro Glu
1 5

<210> SEQ ID NO 71
<211> LENGTH: 10

```
<212> TYPE: PRT
<213> ORGANISM: Artificial Sequence
<220> FEATURE:
<223> OTHER INFORMATION: Peptide 5: Inhibitor reversing Nef-ASK1 effect

<400> SEQUENCE: 71

Pro Val Arg Pro Gln Val Pro Leu Arg Pro
1               5                   10
```